(12) United States Patent
Whitaker

(10) Patent No.: US 12,589,175 B1
(45) Date of Patent: Mar. 31, 2026

(54) SYSTEMS AND METHODS FOR CHEMICAL DISINFECTION

(71) Applicant: PURioLABS, LLC, Dallas, TX (US)

(72) Inventor: Mike Whitaker, Plano, TX (US)

(73) Assignee: PURioLABS, LLC, Dallas, TX (US)

( * ) Notice: Subject to any disclaimer, the term of this patent is extended or adjusted under 35 U.S.C. 154(b) by 878 days.

(21) Appl. No.: 17/693,254

(22) Filed: Mar. 11, 2022

(51) Int. Cl.
| | |
|---|---|
| *A61L 2/22* | (2006.01) |
| *A61L 2/04* | (2006.01) |
| *A61L 2/10* | (2006.01) |
| *A61L 2/26* | (2006.01) |

(52) U.S. Cl.
CPC .................. *A61L 2/22* (2013.01); *A61L 2/04* (2013.01); *A61L 2/10* (2013.01); *A61L 2/26* (2013.01); *A61L 2202/11* (2013.01); *A61L 2202/122* (2013.01); *A61L 2202/15* (2013.01); *A61L 2202/16* (2013.01)

(58) Field of Classification Search
CPC .... A61L 9/00–22; A61L 2/00–28; A61L 2/10; A61L 2/22
See application file for complete search history.

(56) References Cited

U.S. PATENT DOCUMENTS

| | | | |
|---|---|---|---|
| 9,162,001 | B2 | 10/2015 | Sunkara et al. |
| 9,433,694 | B1 | 9/2016 | Hsu |
| 10,716,871 | B1 | 7/2020 | Ricciardi et al. |
| 2019/0314535 | A1* | 10/2019 | Golkowski ............... A61L 2/24 |
| 2019/0321500 | A1 | 10/2019 | Anderson et al. |
| 2021/0361814 | A1* | 11/2021 | Gordon ..................... A61L 9/14 |
| 2022/0016285 | A1* | 1/2022 | Werfel ................. B65G 47/248 |
| 2022/0042692 | A1* | 2/2022 | Bone-Winkel ............ A61L 2/18 |

FOREIGN PATENT DOCUMENTS

| | | | | |
|---|---|---|---|---|
| CN | 111166902 | A | 5/2020 | |
| CN | 111375076 | A * | 7/2020 | ............... A61F 9/02 |
| CN | 211027204 | U | 7/2020 | |
| CN | 211301256 | U | 8/2020 | |
| CN | 212490884 | U * | 2/2021 | |
| WO | WO-2021178764 | A1 * | 9/2021 | ............. G06F 3/044 |
| WO | WO-2022040258 | A1 * | 2/2022 | ......... A41D 13/0002 |

OTHER PUBLICATIONS

CN 111375076 A; machine translation (Year: 2020).*

(Continued)

*Primary Examiner* — Kevin Joyner
(74) *Attorney, Agent, or Firm* — Foley & Lardner LLP

(57) ABSTRACT

A method of disinfection of an object, the method including securing an infected object to a moveable carrousel within a chamber; exposing the infected object to a disinfection cycle, the disinfection cycle comprising: exposing the infected object to an atomized liquid disinfectant fog comprising a disinfectant; exposing the infected object to ultraviolet illumination from an ultraviolet illumination source before, during, after, or any thereof exposing the object to the atomized liquid disinfectant fog to disinfect the object; during the disinfection cycle changing an orientation of the infected object with respect to the atomized liquid disinfectant fog and the ultraviolet illumination source; and removing the object from the chamber.

19 Claims, 45 Drawing Sheets

(56) References Cited

OTHER PUBLICATIONS

CN 211301256 U; Machine Translation (Year: 2020).*

CN212490884U; Machine Translation (Year: 2021).*

STERIS Corporation; "Pro-Lite Sterilization Tray"; Document #10300689 (Rev A); https://ww1.steris.com/onbDocs/V433/1/928807. pdf; 2017; 2 pages.

STERIS Corporation; "Sterile Processing Department: Optimize Your Investment: PRO-LITE Sterilization Trays"; Document #M9278EN.2019-03, Rev.B; https://ww1.steris.com/onbDocs/V448/ 0/1864485.pdf; Mar. 2019; 2 pages.

STERIS; "PRO-LITE Sterilization Trays"; https://www.steris.com/ healthcare/products/v-pro-sterilizers/pro-lite-sterilization-trays; Mar. 1, 2021; 2 pages.

STERIS; "SPD and OR Solutions: Driving Innovation. Delivering Throughput"; Document #M4176EN.2021.09 Rev. E; https://ww1. steris.com/onbDocs/V496/0/3762330.pdf; Sep. 2021; 5 pages.

STERIS; "Sterile Processing Department: Consumables for V-Pro Low Temperature Sterilization Systems"; Document #M10425EN. 2020-01, Rev. A; https://ww1.steris.com/onbDocs/V468/0/3145489. pdf; Jan. 2020; 6 pages.

* cited by examiner

Fig. 1

HORIZONTAL PLANE

HORIZONTAL PLANE

Fig. 10E

| START | | |
|---|---|---|
| | UV-C | <TIME> |
| | HEAT | <TEMP>, <TIME> |
| | VAPOR | <TIME> |
| | COOL-DOWN | <TEMP>, <TIME> |
| END | | |

Fig. 10F

| SENSOR | CONDITION |
|---|---|
| TEMPERATURE | Controls the heat and cooling cycles |
| HUMIDITY | Controls the vapor, heat and cooling cycles |
| UV-C INTENSITY | Controls the UV-C cycle and bulb status monitor |
| CAROUSEL MOTION | Controls the 360 degree movement status |
| DOOR CLOSED | Controls the safety of enclosure exterior |

Fig. 10G

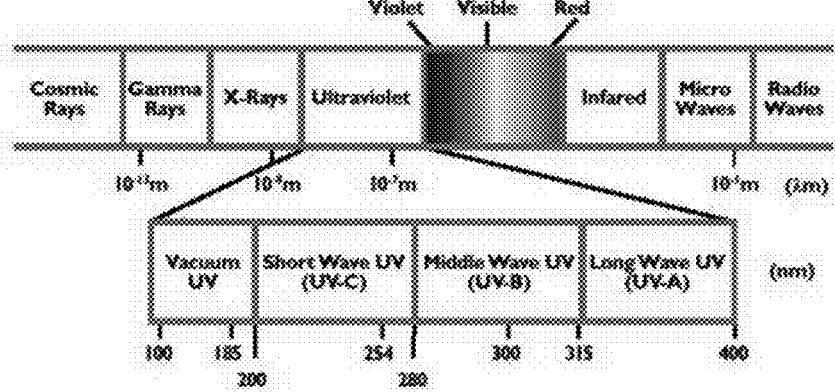

SYSTEMS AND METHODS FOR CHEMICAL DISINFECTION

TECHNOLOGY

The present technology is generally related to disinfection of an infected object. More specifically, it is related to the dual use of chemical disinfection and photolytic disinfection to disinfect or sterilize an infected object.

SUMMARY

In one aspect, a method of disinfection of an infected object includes placing an object that is infected within a chamber; and exposing the object to a disinfection cycle, the disinfection cycle comprising: exposing the infected object to an atomized liquid disinfectant fog comprising a disinfectant; moving the object on a carrousel through the atomized liquid disinfectant fog; and exposing the infected object to ultraviolet illumination before, during, after, or any thereof exposing the object to the atomized liquid disinfectant fog to disinfect the object; removing the disinfected object from the chamber. In some embodiments, the atomized liquid disinfectant fog is formed by the pressurized spraying of a water-based liquid disinfectant solution into the chamber. In any such embodiments, at removal of the disinfected object from the chamber, no disinfectant remains within the chamber. In any such embodiments, the disinfectant comprises hydrogen peroxide, methylene blue, riboflavin, or a mixture of any two or more thereof. In any of the above embodiments, during exposing of the infected object to the atomized liquid disinfectant fog, the ultraviolet illumination may be pulsed on and off.

In another aspect, a method of disinfection of an object includes securing an infected object to a moveable carrousel within a chamber; exposing the infected object to a disinfection cycle, the disinfection cycle comprising: exposing the infected object to an atomized liquid disinfectant fog comprising a disinfectant; exposing the infected object to ultraviolet illumination from an ultraviolet illumination source before, during, after, or any thereof exposing the object to the atomized liquid disinfectant fog to disinfect the object; during the disinfection cycle changing an orientation of the infected object with respect to the atomized liquid disinfectant fog and the ultraviolet illumination source; and removing the object from the chamber. In any of the above embodiments, the atomized liquid disinfectant fog is formed by the pressurized spraying of a water-based liquid disinfectant solution into the chamber. In any of the above embodiments, the atomized liquid disinfectant fog comprises droplets that are about 10 μm to about 100 μm in diameter. In any of the above embodiments, wherein at removal of the disinfected object from the chamber, no disinfectant remains within the chamber. In any of the above embodiments, the disinfectant comprises hydrogen peroxide, methylene blue, riboflavin, or a mixture of any two or more thereof. In any of the above embodiments, the disinfectant comprises hydrogen peroxide. In any of the above embodiments, the method may further include heating the chamber to a temperature from about 25° C. to about 70° C. In any of the above embodiments, a duration of the disinfection cycle is from about 1 minute to about 2 hours. In any of the above embodiments, the method may include illuminating the chamber with visible light, infrared light, a plurality of light wavelengths other than ultraviolet light, or a combination thereof from one or more light sources concurrently with or separately from the illumination with ultraviolet light. In any of the above embodiments, during the disinfection cycle, the ultraviolet light source, or one or more light sources of other wavelengths may be pulsed on and off.

In another aspect, a method of disinfection of an infected object includes placing an infected object within a chamber; and exposing the object to a disinfection cycle, the disinfection cycle comprising, in order: exposing the chamber to rapid airflow for duration of the cycle; exposing the object and chamber to UVC; exposing the object and chamber to a sensitizer; exposing the object and chamber to heat; optionally re-exposing the object and chamber to UVC; and cooling.

The present disclosure relates to medical and personal protective equipment disinfection systems and methods. More particularly, the disclosure relates to a new and improved item disinfection cabinet and method, method for making, distributing, using, and system thereof. Rendering various living contaminants such as viruses and bacteria inert to prevent transmission to other objects and people involves applying a disinfection method to an item. Prior art cases involve a single disinfection method unevenly applied to each item in costly, time-consuming, and impractical manners with unknown effectiveness. The disclosed cabinet provides affordable, convenient, and flexible multi-modal disinfection methods and results. The cabinet includes a portable industrial-grade sealed enclosure for the loading of items needing disinfection with one or more access doors whereby multiple and different disinfection methods are available sequentially or concurrently in a disinfection treatment plan that is selected for its effectiveness per the items and their materials and the targeted contaminants. All disinfection methods are more effective due to the moving orientation between item and disinfection source. Items are presented for treatment via time-saving, quick-change mounting brackets designed purposely to secure and present each item type uniquely. The cabinet enables a room partition separation discipline for "dirty" vs. "clean" item loading and unloading through separate access doors. The cabinet uses computer controlled hardware and software to operate, monitor and set testing and treatment cycles. As such, the general purpose is to provide a new and improved disinfection device and method that has all the advantages of the prior art and none of the disadvantages.

A disinfection treatment plan prescription can be based upon [contaminant×materials×disinfection method×duration]. Extending the duration, or the potency of the disinfection agents and times can surpass mere disinfection and provide for sterilization of objects. As used herein, sterilization is the removal of all microbes or bioburden on the object selected for sterilization/disinfection.

A disinfection cabinet includes: a transportable cabinet frame having a horizontally disposed base, at least one vertically disposed bounding wall, a horizontally disposed top; at least one rotating framework for holding and presenting items for disinfection within the cabinet, the rotating framework configured to rotate about a vertical axis and having plural attachment points; at least two different types of item holders configured for attachment to the attachment points, each of the two different types of item holders configured for holding a different type of item to be disinfected; and at least one disinfecting light source positioned within the cabinet.

The cabinet can further include: at least one heat source configured to heat the interior of the cabinet; and at least one atomized liquid delivery source configured to deliver a disinfecting atomized liquid within the cabinet. The atomized liquid delivery source can be configured to regulate humidity and chemical saturation level within the cabinet.

The cabinet can further include: at least two access doors mounted to the cabinet frame and providing access to an interior of the cabinet through two separate access door openings, wherein each of the access door openings is positioned on an opposite side of the cabinet frame. The cabinet can further include: at least one means for circulating air in the interior of the cabinet. An air source can be configured to provide a supply of air to or remove air from the interior of the cabinet.

The cabinet can further include: a control system configured to control and regulate application of multiple disinfection methods in accordance with a customizable treatment plan. The customizable treatment plan can be based upon the type or composition of items to be disinfected.

The cabinet can further include: for at least one of the at least one framework, at least one guide feature extending vertically for at least a majority of a height of the framework, the guide feature extending along a parallel to an axis of rotation of the framework so as to nudge items on the rotating carousel into intended positions within a predefined circumference around the axis of rotation as the framework rotates. The framework can include one or more vertically disposed outer members having the one or more attachment points, and wherein at least one item holder attached to one of vertically disposed outer members is positioned with a centerline that is angled between an intersection of a first plane tangent to a circumference of rotation of the vertically disposed outer member and a second plane extending along the axis of rotation of the framework as well as the vertically disposed outer member.

The cabinet can further include: a drive mechanism configured to rotate the rotating framework, wherein the drive mechanism is configured to permit slippage of rotation of the framework in case of blockage or manual movement of the framework during loading or unloading.

A method for disinfecting items includes: opening a first access door providing internal access to a transportable disinfection cabinet through a first opening in the cabinet; loading through the first opening a batch of different items onto at least two different types of item holders, each of the two different types of item holders configured for holding a different type of item to be disinfected, each of the items holders being attached to an attachment point on a rotating framework within the cabinet; closing the first access door after loading the batch of items; causing the cabinet to perform a disinfection process on contents of the cabinet, wherein the disinfection process includes: rotating the framework on a vertical axis of rotation within an interior of the cabinet, and exposing the items to a disinfecting light source positioned within the cabinet; in response to an indication from the cabinet that the disinfection process is complete, opening a second access door providing internal access to the cabinet through a second opening in the cabinet positioned on an opposite side of the cabinet from the first opening; and removing the batch of items from the framework through the second opening.

The disinfection process can further include: exposing the items to air movement and circulation within the cabinet, operating a heat source configured to heat the interior of the cabinet, and operating a atomized liquid delivery source configured to deliver a disinfecting atomized liquid to the interior of the cabinet. The disinfecting atomized liquid can include water vapor, wherein the water atomized liquid raises a humidity level in the cabinet.

The disinfection process can be driven by a control system configured to control and regulate application of multiple disinfection mechanisms in accordance with a customizable treatment plan. The control system can be configured to receive data from one or more sensors within the cabinet to sense: motion of items within the cabinet, and operation of one or more disinfection methods, wherein the control system is configured to control the treatment plan in response to data received from the one or more sensors. The customizable treatment plan can be based upon the type or composition of items to be disinfected.

The method can further include: at least one guide feature of the cabinet nudging items on the rotating carousel into intended positions within a predefined circumference around the axis of rotation as the framework rotates.

The framework can include one or more vertically disposed outer members having the attachment points, and wherein at least one item holder attached to one of vertically disposed outer members is positioned with a centerline that is angled between an intersection of a first plane tangent to a circumference of rotation of the vertically disposed outer member and a second plane extending along the axis of rotation of the framework as well as the vertically disposed outer member. The items can include personal protective equipment.

The invention is capable of other embodiments and of being carried out in various ways. Alternative exemplary embodiments relate to other features and combinations of features as may be recited herein.

BRIEF DESCRIPTION OF THE FIGURES

The disclosure will become more fully understood from the following detailed description, taken in conjunction with the accompanying figures, wherein like reference numerals refer to like elements, in which:

FIG. 1 illustrates a high perspective view of the external surfaces and working components and important features of the cabinet.

FIG. 10E illustrates pre-set or variable treatment plans that are a combination of disinfection methods, either in serial or overlapping order, with adjusted thresholds and duration FIG. 10F illustrates use of sensors to assure the needed environmental factors are reached and maintained to assure treatment efficacy and operator safety.

FIG. 10G illustrates the range of UV light in the electromagnetic spectrum.

FIG. 20 is a front view of a universal bracket base, according to an example embodiment.

FIG. 23 is a side view of a universal bracket base, according to an example embodiment.

DETAILED DESCRIPTION

Figure 2:
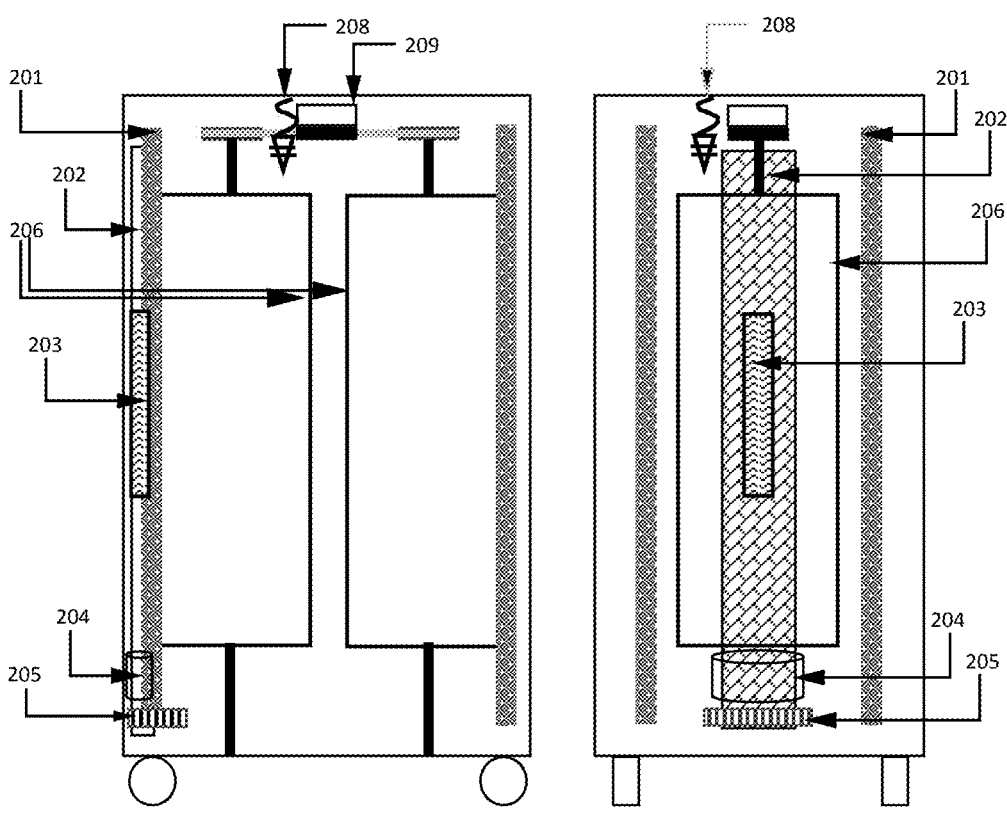
FIG. 2 illustrates a high perspective view of the internal space and working components and item movement and light circulation of the cabinet, including the item movement multi-exposure embodiment.
Figure 2:
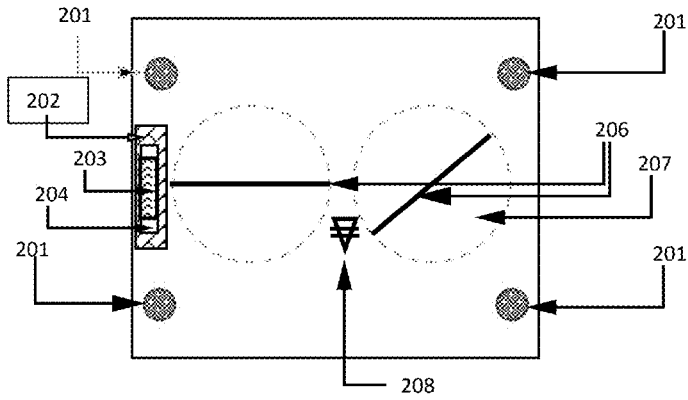

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Described herein is a disinfection system that combines ultraviolet (UV) illumination of a contaminated surface with a chemical disinfectant. It is through the combination of the UV illumination and the chemical disinfectant that high levels of disinfection may be rapidly and evenly achieved for all object surfaces, with no residual chemical disinfectant remaining or in need of disposal or further treatment. More specifically, the chemical disinfectant is an atomized (i.e. micro-fine droplets) water-based solution containing the disinfectant. This disinfectant may have the additional capability of being a sensitizer capable of photodynamic therapy, whereby the disinfectant emits molecular radicals or elemental ions that further perform disinfecting. Hydrogen peroxide is an example of a disinfectant that can also be a sensitizer. Water-based solutions containing methylene blue and riboflavin are illustrative sensitizers that provide disinfecting action in the presence of UV light. A chamber is configured for holding various objects that may require disinfection. Upon exposure of the objects to both the UV illumination and the atomized liquid disinfectant, the targeted microbe's outer layers are weakened and the anatomical structure or the genetic reproductive structure of the microbe is damaged or destroyed.

As used herein, the term "disinfection" can be defined to different degrees. High-level disinfection (HLD) is the destruction of all viruses, vegetative bacteria, fungi, mycobacterium, and some, but not all, bacterial spores. HLD is operationally defined as the ability to kill $10^6$ mycobacteria (a six-log reduction). Intermediate-level disinfection is the destruction of all myco-bacteria, vegetative bacteria, fungal spores, and some nonlipid viruses, but not bacterial spores. Low-level disinfection is a process that can kill most bacteria (except mycobacteria or bacterial spores), most viruses (except some nonlipid viruses), and some fungi. Compare this to chemical sterilization, which is a process that can kill all living bioburden (100%). The system provided for herein, can achieve a full range of disinfection and chemical sterilization-based upon the treatment plan, duration, and potency of disinfectants. The technology is particularly applicable to properly prepared (cleaned, rinsed, and dried) non-critical medical devices and supplies in a wide variety of healthcare settings. In some embodiments, where soiling of the object is sufficient such that the thickness or coating of the object would inhibit action by the methods described herein, it may be advisable that prior to placing a soiled object within the chamber it is manually cleaned.

During the disinfection process/cycles, the outer layer of a microbe is microbe may be weakened by exposure to dry air compared to moist air. Hence, the methods described herein, in some embodiments, being with an airflow of dry air prior to and/or following the other UV and atomized liquid treatments. Further, because larger volumes of air impact the outer layer of the microbes more, the system is configured in some embodiment to move hundreds of cubic feet of air per minute within the chamber.

The UV-C Light and atomized liquid disinfectant disinfection cycles operate at low pressure and temperature, and are suitable for processing medical devices without leaving residues. The disinfected devices are ready for use at the completion of the cycle, with no cool down or aeration period is required following completion of the cycle.

The UV light that is used in this system is preferably UV-C light (UVC) having a wavelength of about 100 nm to about 280 nm. The UVC light operates broadly within this range, however, in some embodiments, the UVC light that is used is from about 240 nm to about 280 nm, about 250 to about 260 nm, or it may be about 254 nm. It is understood that UVC inactivates microorganisms by triggering the formation of specific thymine or cytosine dimers in DNA and uracil dimers in RNA, which causes inactivation of microbes by causing mutations and/or cell death and failure to reproduce.

As noted above, the hydrogen peroxide ($H_2O_2$) is an example of a possible diluted water-based disinfectant used in the processes described herein in an atomized form, i.e. as a fine atomized liquid or fog. Used by itself as a disinfectant, $H_2O_2$ provides for germicidal effects, even at low concentrations. However, as a sensitizer for photodynamic therapy, under purposefully-timed direct light, $H_2O_2$ forms hydroxyl radicals that are even more destructive toward microbes and other infectious agents. Thus, it may be said that under photon stimulation, $H_2O_2$ is a sensitizer that, when activated to form hydroxyl radicals, performs photodynamic therapy attacking membrane lipids, DNA, and other essential cell components. Catalase, produced by aerobic organisms and facultative anaerobes that possess cytochrome systems, can protect cells from metabolically produced hydrogen peroxide by degrading hydrogen peroxide to water and oxygen. This defense is overwhelmed by the layered treatments used for disinfection in the system described herein. Other sensitizers can serve the same function as $H_2O_2$. In the system herein, only minute amounts of atomized liquid disinfectant are required to achieve the disinfection threshold desired. Additionally, water-based moisture atop a surface has the ability to bend germicidal light around corners and into crevices, enabling more effective disinfection.

In the system, a disinfection cabinet is provided, the cabinet including a movable substrate holder, a liquid atomizer, a UV source, and a chemical disinfectant source. When in use, atomized liquid disinfectant may be generated as a fluid droplet by passing through the atomizer under pressure, while the inside of the cabinet is at or near ambient temperature and pressure. The fluid droplets may be from about 10 μm to about 100 μm in diameter and forming a fog within the disinfection cabinet. In some embodiments, the fluid droplets are from about 30 μm to about 70 μm, from about 40 μm to about 60 μm, or from about 50 μm to about 60 μm in diameter. Dispersal of the fog throughout the cabinet may be achieved by motion of the substrate holder or constant airflow through the system, ensuring coverage of all surfaces, including infected substrates, by the atomized liquid disinfectant within the cabinet.

Before, during or after the dispersal of the atomized liquid disinfectant into the chamber, UV illumination and/or photon therapy from any light wavelength may be initiated in purposeful timings and pulsing patterns to achieve maximum UVC disinfection simultaneous with maximum atomized liquid disinfectant disinfection and possible additional sensitizer photo-activation. When initiated prior to the introduction of the atomized liquid disinfectant into the chamber, the UV illumination may start the disinfection process as some microbes and infectious agents are weakened and destroyed by UV illumination alone. When initiated during or after introduction of the atomized liquid disinfectant, the UV illumination works with the atomized liquid disinfectant to provide a simultaneous compounded disinfecting benefit. Further, if the atomized liquid disinfectant is also capable as a sensitizer for photodynamic therapy, additional disinfection power is achieved via generated hydroxyl radicals or singlet oxygen or other electron-unstable elements or molecules that can attack the targeted microbes within the cabinet. The generation of such oxidative species may be by illumination of the $H_2O_2$ either prior to or after contact with the surface. However, it is noted that the amount of atomized liquid disinfectant used in a given disinfection cycle is sufficient to not only combine with UV illumination to disinfect, but it too is entirely converted to water or non-harmful residual material as part of the system design. As an example of one possible liquid disinfectant solution, for the amount of $H_2O_2$ used, the length of the cycle and amount of light, heat and air purposely ordered and are such that no amount of $H_2O_2$ remains after completion of the cycle, assuring the safety of objects and cabinet interior.

To adapt to different starting points for relative humidity (Rh) (e.g. Summer Rh is higher than winter Rh, on average), the treatment cycles have dual minimum thresholds that must be met by the $H_2O_2$ process, whereby a minimum volume of $H_2O_2$ disinfectant liquid must be dispersed within the treatment area and a minimum Rh % must be reached. This dual logic assures: 1) enough $H_2O_2$ is employed in higher humidity conditions as if only Rh % is used as the control, the upper Rh limit would be reached quickly; and 2) additional $H_2O_2$ is employed in low humidity conditions as the dry air will absorb a portion of the needed $H_2O_2$ rather than being applied directly to the treatment area surfaces. The $H_2O_2$ process is terminated just short of the saturation point at a given Rh.

In one aspect, a method of disinfection of an infected object includes placing an object that is infected within a chamber; and exposing the object to a disinfection cycle. Each disinfection cycle may include one or more steps as described below. In one step, the cycle may include exposing the infected object to an atomized liquid disinfectant fog. In another step, the cycle may include exposing the infect object to ultraviolet illumination before, during, after, or any thereof exposing the object to the atomized liquid disinfectant fog to disinfect the object. As a final step, the disinfected object may be removed from the chamber. In some embodiments, the atomized liquid disinfectant is in the form of a fog or fog that is formed by the pressurized atomized liquid of a hydrogen peroxide solution into the chamber. Accordingly, the chamber may include one or more atomized liquid nozzles for delivering the hydrogen peroxide to the chamber. The atomized liquid disinfectant fog may include droplets that are about 10 μm to about 100 μm in diameter. As noted above, upon finishing of the cycle and opening of the chamber to remove the disinfected object, no hydrogen peroxide remains within the chamber, thereby eliminating exposure of individuals or operators of the system to such species.

The atomized liquid disinfectant fog may be formed from an aqueous solution of from 1 to 30 vol % hydrogen peroxide. This includes aqueous solutions that are from about 3 to about 10 vol % hydrogen peroxide. In some embodiments, the hydrogen peroxide solution is about 6 vol % hydrogen peroxide. The specific amount of hydrogen peroxide may vary from a few milliliters dispersed as the fog on up, such that the volume is able to be degraded in a timely manner by the UV illumination and is appropriate for the size of the chamber. Where other sensitizers such as methylene blue or riboflavin are used, the aqueous or solvent solution of the material may contain from about 0.1 to 10 wt % of the sensitizer. Accordingly, in some embodiments, the chamber has a volume from about 10 ft³ to about 40 ft³, and the ratio of volume of the aqueous solution (from about 1 wt % to about 30 wt %; or at about 6 wt %) to the volume of the chamber is from about 0.5 ml/ft³ to about 1.5 mL/ft³. In other embodiments, the chamber has a volume of about 10 ft³ to about 40 ft³, and the ratio of the volume of the equivalent disinfectant at 100% concentration to the volume of the chamber is from 0 to 0.15 mL/ft³.

| Total Fluid (F) | Ratio Fluid/ft³ | Total Sensitizer | Ratio Sensitizer/ft³ |
|---|---|---|---|
| <45 ml | 0.5 ml-1.5 ml | <3 ml | <.16 ml @ 100% |

In some embodiments, the methods include moving the object on a carrousel through the atomized liquid disinfectant fog. In other embodiments, or in addition to the movement through the atomized liquid disinfectant fog, the method may also include moving the object on a carrousel during exposure to the ultraviolet illumination. The movable carrousel is further described below in relation to the chamber.

In some embodiments, the methods include heating the chamber to a temperature from about 25° C. to about 70° C. In other embodiments, the disinfection cycle is timed from about 1 minute to about 2 hours, about 5 minutes to about 15 minutes, or from about 10 minutes to about 20 minutes, or from about 15 minutes to about 40 minutes.

In some embodiments, the methods further include exposing the chamber with ultraviolet, visible, or infrared light-of individual colors of light and their respective wavelengths contained (e.g. red, white, blue, green, etc.) either concurrently with or separately from the illumination with ultraviolet light. Such embodiments may assist in killing bioburden or microbes that may be susceptible to illumination at such other wavelengths, in addition to the ultraviolet light. Such embodiments may assist in the photoactivation of any sensitizer contained in the atomized liquid disinfectant. Such embodiments may assist in the degradation of any remaining distributed atomized liquid disinfectant. In some embodiments, no hydrogen peroxide can be detected in the chamber after completion of the disinfection cycle.

As noted above, airflow may be helpful in both disinfecting and drying of the chamber. Accordingly, the disinfection cycle may further include, either before during or after, exposure of the object to the atomized liquid disinfectant fog, exposing the chamber and object to airflow rates of 50 ft³/minute or more. This may include from about 100 ft³/min to about 1,000 ft³/min, or from about 1000 ft³ to about 10,000 ft³/min. When used as an initial step, the airflow exposure can assist in dislodging microbes from the surface of the infected object, and when used at the end of the cycle, the airflow exposure can assist in drying of the chamber. When used after distribution of atomized liquid disinfectant, the airflow can push the disinfectant into material layers, crevices, and hard-to-reach spaces.

As explained further below with regard to the cabinet features, airflow can be maintained throughout the chamber to enhance positive item surface airflow effects on disinfection. Air circulation aids in moving organisms from surfaces to airborne status, making them more vulnerable to chemical and physical disinfection processes. Evenly distributed airflow moves low-pressure atomized liquid disinfectant on all sides of items contained in the unit and allows penetration of sensitizer into fibers and crevices of porous items. Additionally, airflow within the cabinet assists with drying the chamber and disinfected items when the disinfection cycle is complete.

The cabinet may also have a heat source for preconditioning of microbes by expanding, drying, and agitating the outer protective surfaces of the organism and increasing the speed of chemical reactions. Heat also is used for drying and removing humidity at the end of the cycle. Heat may also be used to further degrade any atomized liquid disinfectant remaining within the cabinet prior to the treated object being removed from the cabinet.

In the following description, references are made to various embodiments in accordance with which the disclosed subject matter can be practiced. Some embodiments may be described using the expressions one/an/another embodiment or the like, multiple instances of which do not necessarily refer to the same embodiment. Particular features, structures or characteristics associated with such instances can be combined in any suitable manner in various embodiments unless otherwise noted. By way of example, this disclosure may set out a set or list of a number of options or possibilities for an embodiment, and in such case, this disclosure specifically contemplates all clearly feasible combinations and/or permutations of items in the set or list.

Figure 1:
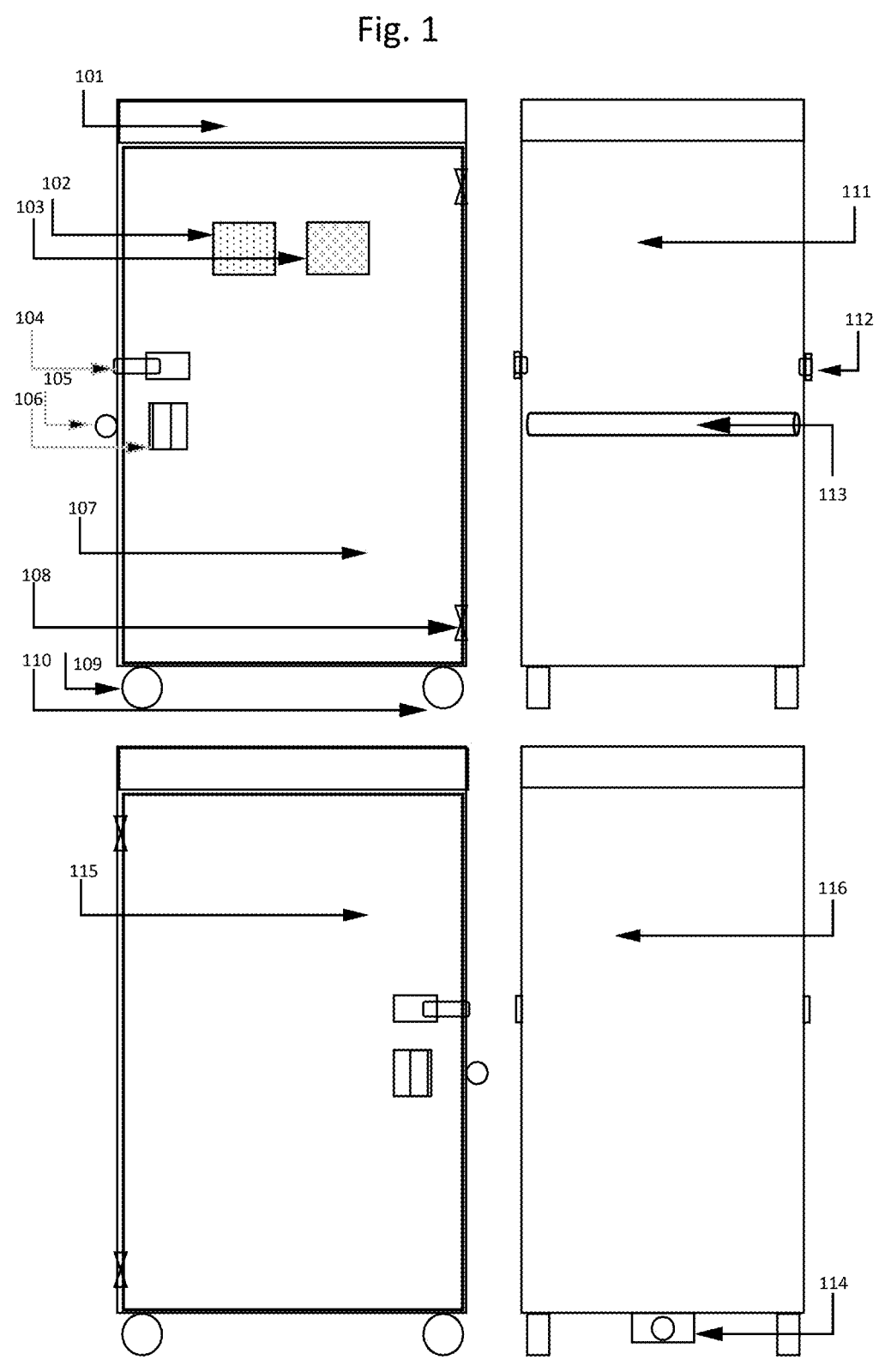

FIG. 1 illustrates a view of the external surfaces and working components and important features of a disinfection cabinet. The cabinet contains all electronics and drive and pump and actuating components in the area 101, which can be separate from the interior of the cabinet to protect possible sensitive components from the harshness of disinfection methods, whereby access to area 101 can be via a separate access door from above. For the same purposes, area 101 could be located on any other side of the cabinet. A right side access door 107 the cabinet can include a see-through safety window 102 and operator control panel/screen 103. Alternatively, a see-through window 102 could be located on any surface of the cabinet and operator control panel/screen 103 could be located on any surface of the cabinet. Security latch 104, 112 that applies locked and sealed pressure to the door enclosure can be centrally located along the vertical dimension. One or more security latches can be used for the same purposes. Each access door offers a pull-handle 106, located centrally on the vertical dimension. One or more door handles can be used for door opening. Door hinge 108 allows the door to swing open and contains the wiring necessary for door components whereby the threaded wiring between cabinet and door is not visible to the operator when door is open or closed. One or more door hinges could be utilized in other locations for one or more access doors. For portability ease, the cabinet can incorporate a push/pull handlebar 105, 113 and swivel wheels 109 and fixed wheels 110 to allow a single person to easily maneuver the cabinet and steer from the handle side 111 of the cabinet. Alternatively, one or more handles can be used to grip and maneuver the cabinet and can be located elsewhere on the cabinet exterior. A left side access door 115 can feature components common to the right side access door. The wall-side of the cabinet 116 can be designed to be placed against a wall to allow for a natural separation between operating sides and openings. The cabinet can be configured to have no protruding cords or parts that can catch during transport or operation and power inlet 114 is ready to accept a common 120$v$ power connection and is located where any connected power cord will not interfere with operator movement or create a tripping hazard.

FIG. 2 illustrates a view of the interior surfaces, working components and important features of the cabinet. Disinfection Method 1 (light) can be positioned in a manner that provides multi-bulb and multi-angle access 201. Disinfection Method 2 (heat) can be delivered from heating element 203 and transported by air duct 202. Disinfection Method 3 (air) can be propelled by a fan or blower 204 providing a means for moving air, pushing or pulling air within the enclosure. The fan or blower 204 can move air through a HEPA filter 205 located either interior or exterior of the cabinet. The fan or blower can be located either interior or exterior of the cabinet. Disinfection Method 4 (vapor) can be delivered from a fogging release unit 208 and dispersed throughout the interior via circulating air propelled by fan or blower 204. The delivered atomized liquid can include, for example, hydrogen peroxide, other disinfectant, other sensitizer, water, solvent, drying agent, fragrance, or a combination thereof. The fogging release unit 208, accordingly can be used to increase the humidity within the cabinet to a desired or target level for disinfection purposes.

The above multiple disinfection methods are part of the simultaneous and serial multi-disinfection method embodiment. The application of the above disinfection methods upon items contained in the cabinet during a treatment cycle has those items transported on or within a framework 206, the item movement multi-exposure embodiment, as one or more frames move on their center points in the complete 360° carrousel movement area 207, driven by power movement 209, providing uniform treatment application. Alternatively, the item could be stationary and the disinfection method can be moved around the item to accomplish the above embodiment. Alternatively, the item can be moved upon a conveyor or carriage for presentation to various disinfection methods. Alternatively, the movement of items can achieve a partial or full exposure of the item as the direction and total movement of the item can be different than above. In the item movement multi-exposure embodiment, due to increased exposure of all facets of an item to various treatments the efficacy of all disinfection methods is enhanced and the time required to achieve a disinfected state is lowered respectively. One embodiment provides a new and improved item disinfection system and method that provides maximum possible item exposure to all disinfection methods and treatments by changing the position between item and disinfection method whereby simultaneous exposure is possible to each item, on all facets/sides of the item (see FIGS. 10A-D).

Figure 3:
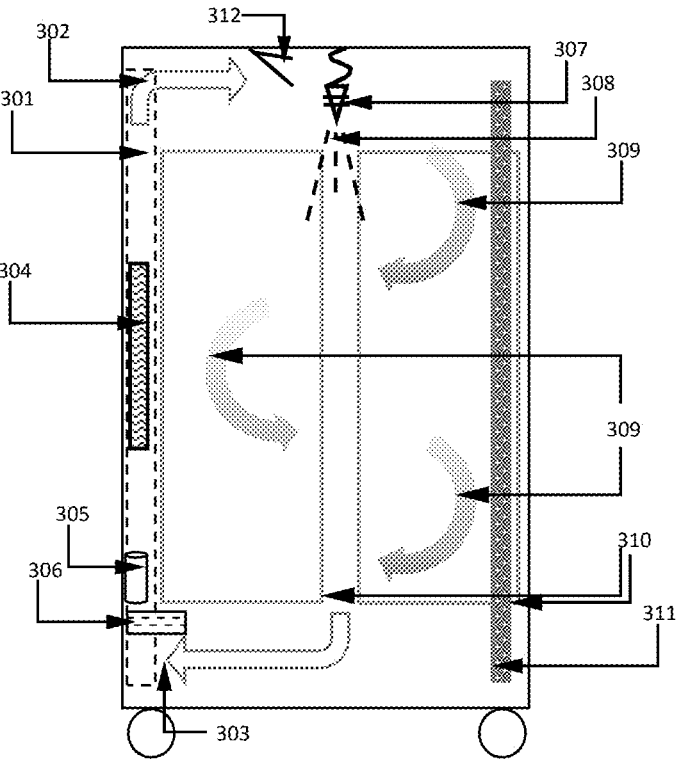
FIG. 3 illustrates a high perspective view of the internal space and the light, air, heat and atomized liquid circulation throughout the cabinet as part of the simultaneous and serial multi-disinfection method embodiment.

FIG. 3 illustrates the simultaneous and serial multi-disinfection method embodiment whereby internal space and the air, heat and atomized liquid circulation throughout the cabinet as air enters the duct 301 at location 303, travels through the air filter 306, through the fan or blower assembly 305, through heating element 304, and exits duct 301 at location 302, and is exposed to one or more light sources 311. Disinfection Method 1 (light 311), Disinfection Method 2 (heat 304), Disinfection Method 3 (air 305) and Disinfection Method 4 (atomized liquid 307, 308) are effective due to enveloping all interior cabinet air and exposed surfaces and materials of items contained in the cabinet during a treatment cycle as the airflow is circulated and tumbled 309 from top to bottom of cabinet as item presentation framework in the form of a carrousel 310 moves the items within the treatment area. Airflow can be guided for balance and best distribution of atomized liquid and air using the airflow guide 312 to selectively deflect portions of the airflow in different directions within the enclosure. The simultaneous and serial multi-disinfection method embodiment can offer two or more disinfection methods that can include ultra-violet light, heating, cooling, air pressure, air movement, and vaporized liquids with or without chemical components, laser light, and more-all of which can be customized as part of any treatment plan based upon the items and materials to be disinfected. The amount, level, intensity, saturation, duration of any disinfection method is adjustable as needed for maximum efficacy of any treatment of any item. The above embodiments can achieve a closed system of air and item movement whereby no air is added or subtracted from the enclosure and requiring no external vents outside the enclosure. Alternatively, the above embodiments can be operated similarly if the fan or blower 204 is moving air sourced from outside the enclosure into the enclosure and moving the air in the enclosure outside the enclosure.

One embodiment provides a new and improved item disinfection system and method that can combine two or more disinfection methods in a manner that customizes a disinfection treatment plan (based upon items to be treated or contaminants targeted) and executes that plan via controls of the hardware. The objective involves a multi-method attack upon contaminants within the same treatment cycle whereby thoroughness is enhanced by employing multiple disinfection methods simultaneously or in a series within the same cycle. For example, sensitive electronic devices may be treated with UV-C and heat but no atomized liquid. In another example, sensitive plastic materials may be treated with UV-C and atomized liquid but no Heat. Additionally, the duration of any disinfection method is part of customized disinfection treatment plan. For example, some materials cannot tolerate long UV-C exposure and so the duration of UV-C can be shortened and other disinfection methods extended.

Figure 4:
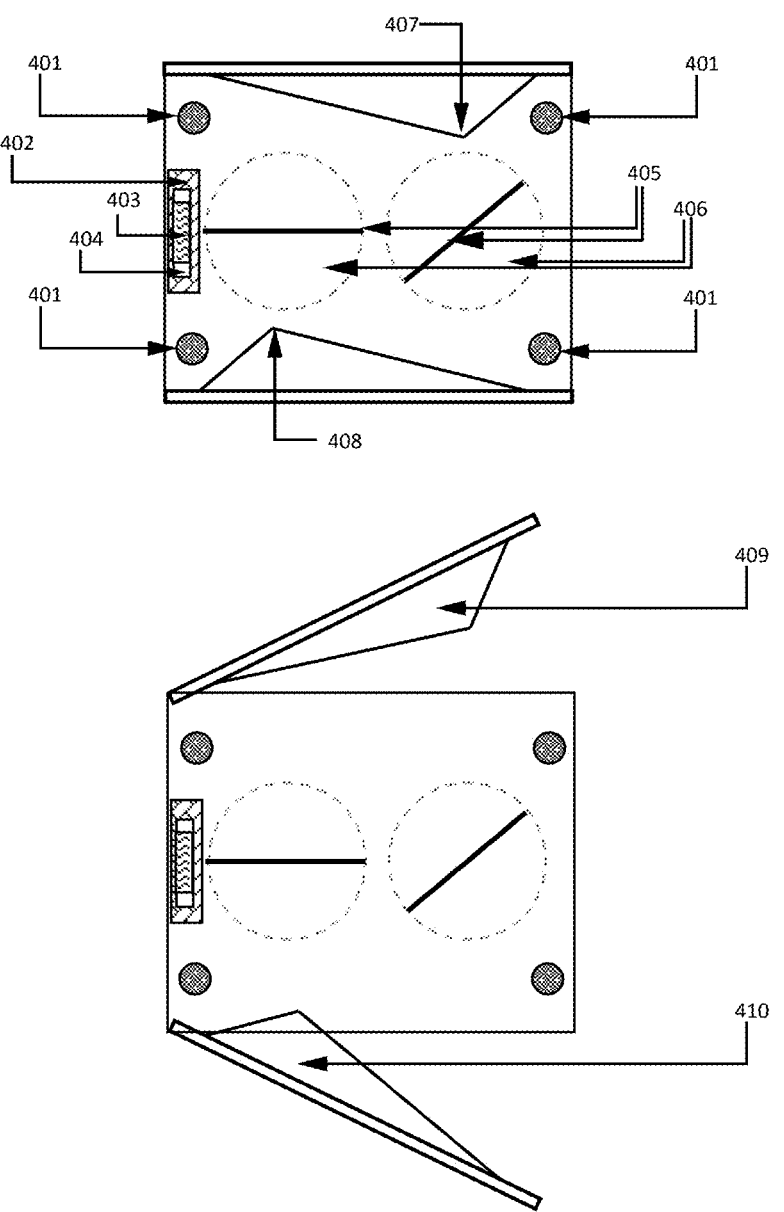
FIG. 4 illustrates a high perspective view of the internal space and the cabinet's item physical guide embodiment and interior space saving embodiment.

FIG. 4 illustrates the cabinet's internal space using item physical guides to save interior space in accordance with one embodiment. Disinfection Method 1 (light) can be positioned in a manner that provides multi-bulb and multi-angle access 401. Disinfection Method 2 (heat) can be delivered from heating element 403 and transported by air duct 402. Disinfection Method 3 (air) can be propelled by a fan or blower 404 providing a means for moving air, pushing or pulling air within the enclosure. As the framework carrousels 405 move at their center point 360° within carrousel movement area 406, items contained within the carrousel could potentially shift whereby all or a portion of any item could extend beyond the carrousel movement area 406 and if so, item physical guide point 407, 408 is positioned to nudge the item toward carrousel movement area 406 and preventing the item from leaving the carrousel movement area 406 where the item would be prevented from receiving or would prevent other items from receiving full treatment by chosen disinfection methods. The triangular form 409, 410 on the interior of the cabinet provides the physical guide points 407, 408 and the triangular form 409, 410 occupies significant interior area that would otherwise be open and require more disinfection efforts if triangular forms 409, 410 did not exist. Physical guide points could protrude from another interior surface of the cabinet to correct the position of any item as a means to the item physical guide embodiment. Interior panels could protrude from one or more surfaces to occupy space as a means to the interior space saving embodiment. The item physical guides provide a new and improved item disinfection system and method that has built-in physical guide material on the interior of the enclosure or door assembly whereby any item that becomes misaligned with its intended position as it rotates is nudged toward its original intended position so that it remains in place for exposure as well as it does not affect any other item or the cabinet's mechanisms. Alternatively, the item can be moved upon a conveyor or carriage and a similar physical guide can be positioned to assure the item remains in its intended position throughout the treatment cycle.

Figure 5:
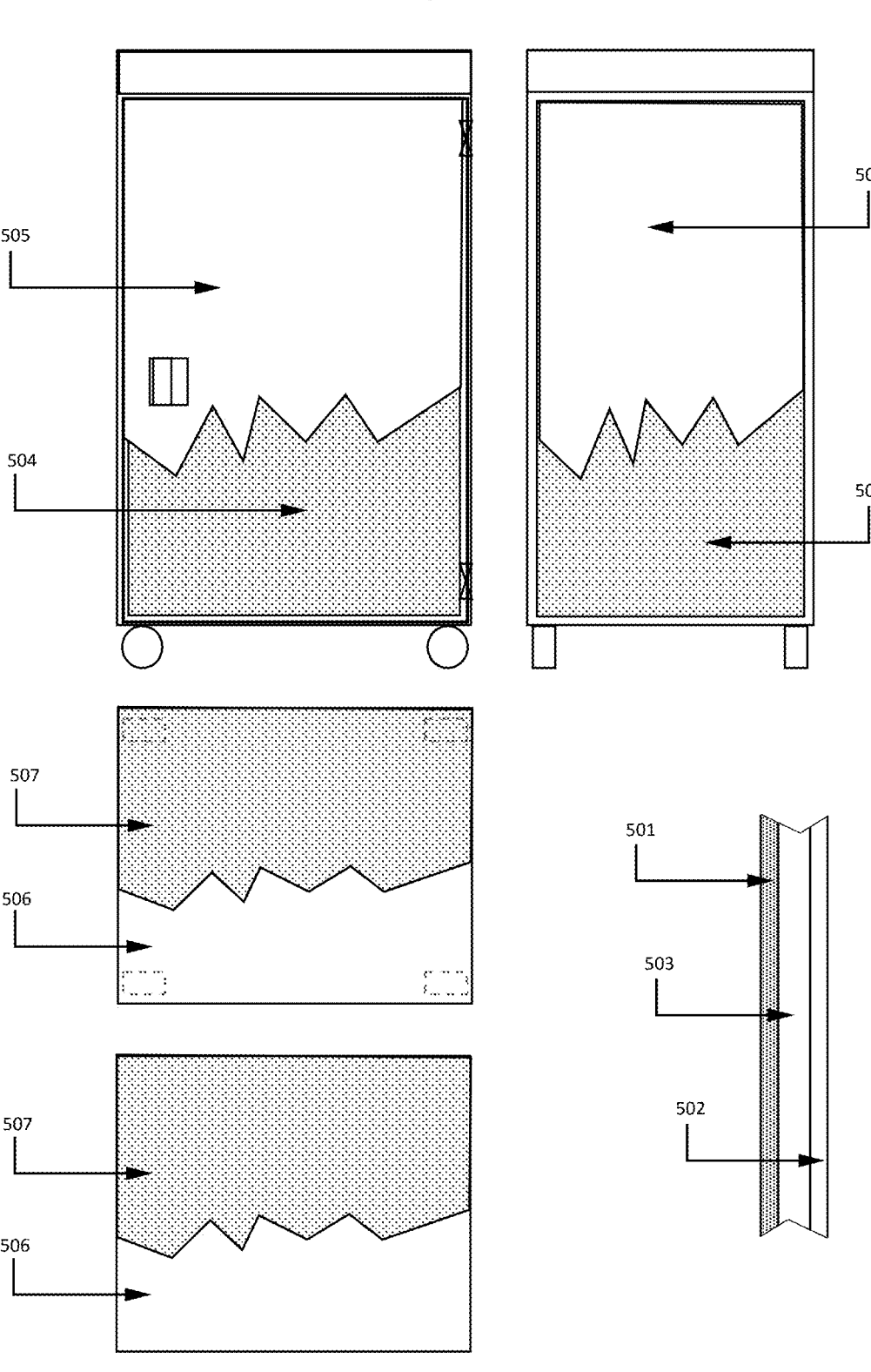
FIG. 5 illustrates a high perspective view of the cabinet's multi-layered frame whereby all facets of the cabinet have at least two layers and a space between those layers, allowing for all wiring and connectivity to be embedded between those layers and also providing insulation and heat dissipation between the interior and exterior of the cabinet.

FIG. 5 illustrates a multi-layered frame whereby any or all facets of the cabinet can have at least two layers, inner layer 501, outer layer 502, and a space between those layers 503, allowing for all wiring and connectivity to be embedded between those layers and also providing insulation and heat dissipation between the interior and exterior of the cabinet. In one embodiment, all sides of the cabinet have inner layer 504 and outer layer 505 and the top and bottom sides of the cabinet have inner layer 507 and outer layer 506.

Figure 6:
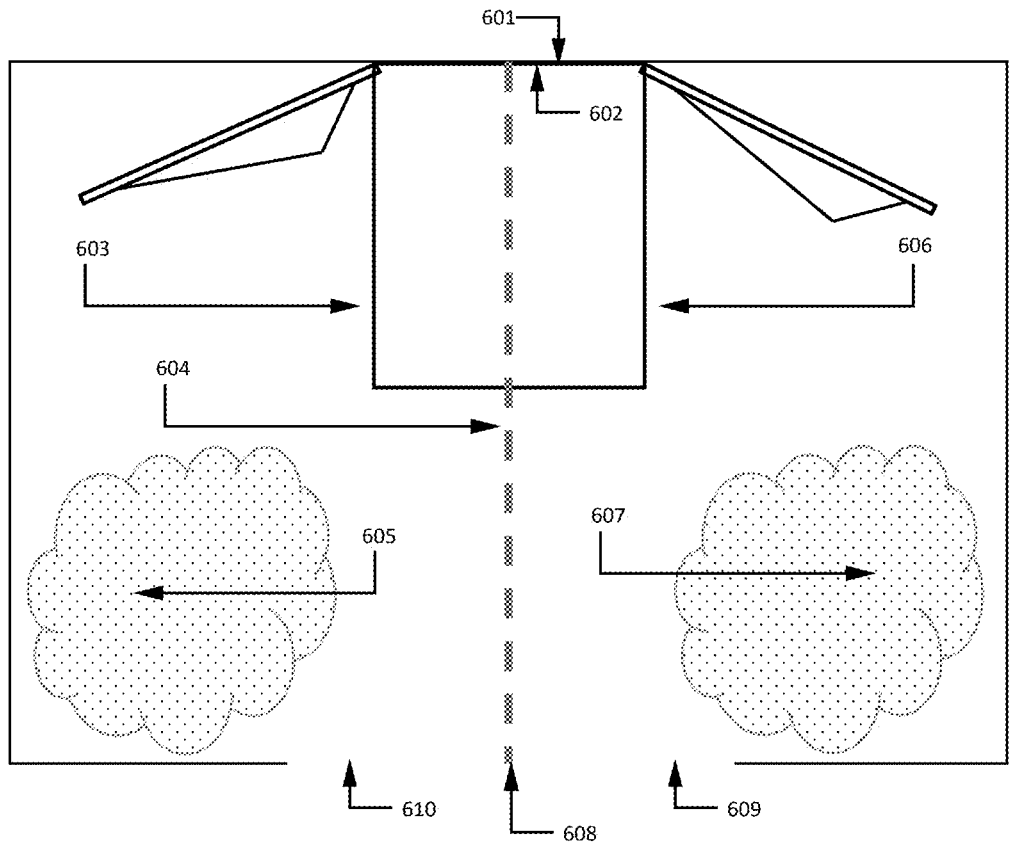
FIG. 6 illustrates a high perspective view of the cabinet as part of the room partition embodiment whereby the cabinet's multiple doors and cabinet combined with a drape or curtain or wall allows for separate work spaces, one for contaminated and one for disinfected.

FIG. 6 illustrates the cabinet positioned as part of a room partition where a side of the cabinet 602 is placed against a wall 601 with operator loading side 606 opposite non-operator unloading side 603, separated by a temporary or fixed partition or wall 608, allowing for separated work areas, "dirty" loading area 607, "clean" unloading area 605, separated loading doorway from unloading doorway 609 from unloading entrance 610. An operator can organize the inbound and outbound items for treatment based upon the ability for the cabinet and its design elements to be part of the room partition embodiment. Alternatively, the "dirty" loading vs. "clean" unloading access doors and their associated loading/unloading areas could be located differently than illustrated. Alternatively, the cabinet can be positioned to be part of a room partition in the middle, left or right location, as part of the room partition embodiment. This embodiment essentially includes a new and improved physical discipline in the disinfection process whereby the cabinet can have more than one access door, one or more doors for "dirty" items and one or more doors for "clean" items, allowing the operator to partition their cycle schedule and loading/unloading discipline with re-contamination risk lowered extensively. The embodiment allows for a 1st operator and 2nd operator, each operator working on separate side of the cabinet so a physical barrier 604 can be erected around the cabinet (e.g. drape) so that the room is separated in half, dirty vs. clean (see FIG. 6).

Figure 7:
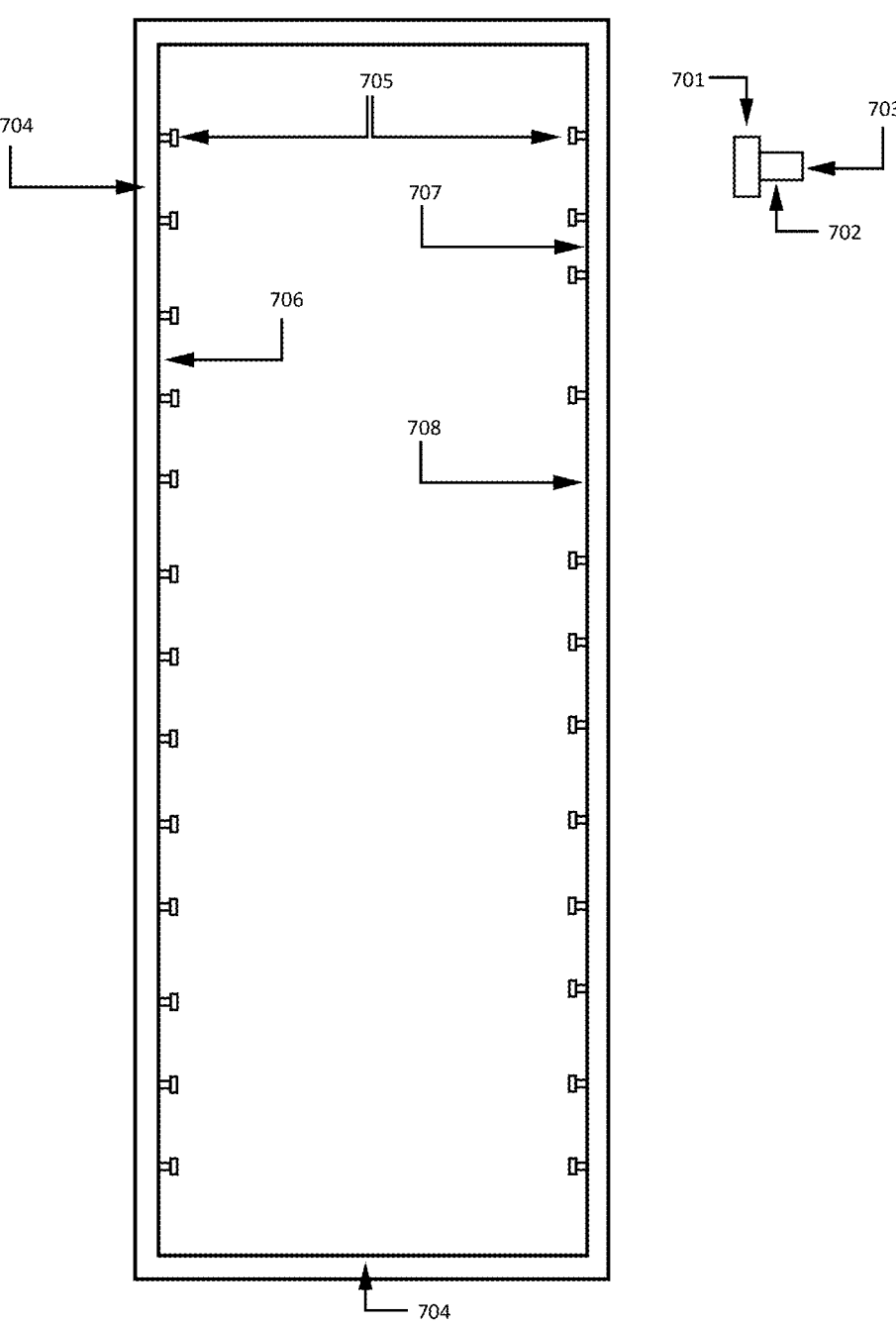
FIG. 7 illustrates a high perspective view of the item presentation framework embodiment of the cabinet whereby item mounting attachment points are located on the framework and item mounting brackets can be attached at one or more item mounting attachment points.

FIG. 7 illustrates the item presentation framework and attachment embodiment of the cabinet whereby item mounting attachment points 705 are located on the framework 704 in accordance with one embodiment. Item mounting attachment points can be constructed of an edge 703 adjacent to the framework 704, an extension 702 from the framework that attaches to an anchoring point 701 whereby the anchoring point 701 has a physical attribute that provides anchoring leverage for any object with a reciprocating receiving attribute. Item mounting attachment points 705 can be spaced 706, 707, 708 along the framework or surface plane of the item presentation framework in an arrangement that provides flexible placement of item mounting attachments or the items themselves. Alternatively, the item presentation framework could be a different shape or dimensions while accomplishing the same mounting result for item mounting attachments, as an example, the item presentation framework could be a cylinder and item mounting attachment points can be holes and/or pegs positioned on and/or throughout the surface of the cylinder and selective physical guides can maintain the item's intended position. Alternatively, item mounting attachment points can be achieved for attachment using different attachment methods, including clips, magnets, brackets, notches, and any other means of attaching an item or item mounting bracket to the item presentation framework. For example, the item mounting attachment points 705 can be a protruding member that is detachably coupled with the framework 704, such as shank-style fasteners (i.e., bolts, screws, pins, etc.). The protruding member can be received by an opening or aperture of a bracket, as is shown in detail below with reference to FIGS. 21 and 22. Put another way, the aforementioned mounting attachment points 705 can be a male member, while the bracket can be a female member (i.e., an opening or aperture configured to receive the male mounting attachment point 705). In another example, the mounting attachment points 705 can define apertures or openings that are configured to receive a protrusion, protruding member, shaft, shank, projection, etc. of a bracket, as is discussed below with reference to FIG. 23. In such examples, the mounting attachment point 705 can be a female member that is configured to receive a male protrusion, protruding member, shaft, shank, projection, etc. of bracket. In some examples, the mounting attachment point 705 can comprise an aperture that is configured to receive a fastener (e.g., screw, rivet, pin, etc.), where the fastener is configured to be received by an opening or aperture defined by a bracket. In another embodiment, the mounting attachment point 705 can include an adhesive (e.g., sticky, adherent, epoxy, glue, etc.) element that can be configured to adhere to a bracket. In yet another example, the bracket can include an adhesive (e.g., glue, resin, epoxy, bonding agent, etc.) element that is configured to adhere to a mounting attachment point 705 or to the framework 704 generally.

The item presentation framework and attachment embodiment enables rapid loading and unloading of items within the enclosure via quick-connect item mounting adapters attached to the framework. Unique mounting adapters are provided as part of one embodiment to easily fit specific categories of items without any adaptation or tie-downs or added fixtures, saving the operator loading and unloading time and allowing for a custom mix of items per the needs of the operator. Improved treatment efficacy can be achieved via the item mounting adapters as they are customized to serve each category of item and achieve maximum surface area presentation from all sides of the item which therefore achieves maximum treatment exposure on all sides of the item, thereby lowering cycle times and increasing treatment effectiveness. The movement method and the power applied to the carrousel host framework can allow for 100% slippage if movement is blocked or if manual movement is desired by the operator when loading the enclosure and the carrousel assembly may be rotated to face the operator for loading and unloading purposes.

Figure 8:
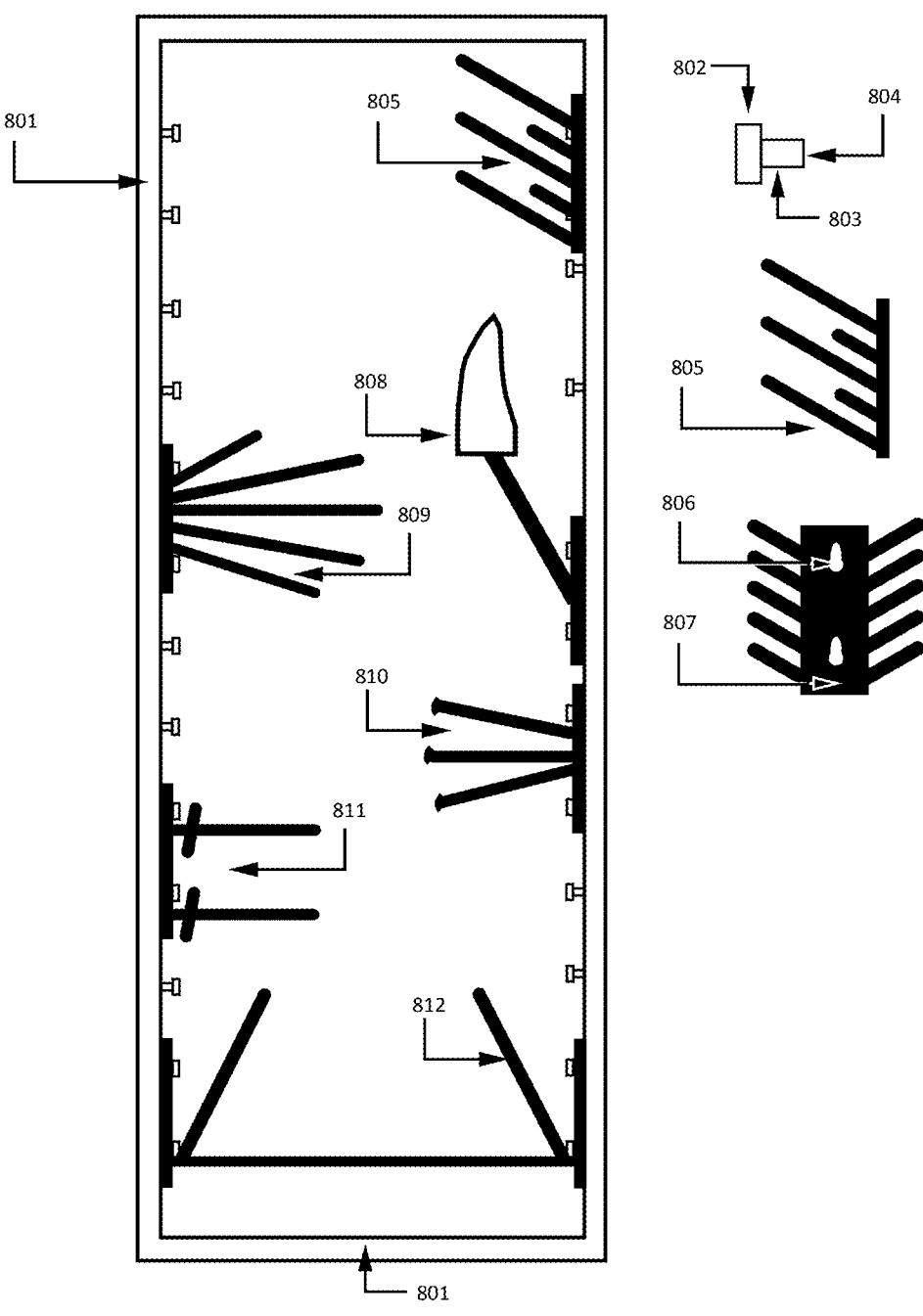
FIG. 8 illustrates a high perspective view of the many possible item mounting brackets variably arranged and attached to the framework as item presentation framework embodiment of the cabinet.

FIG. 8 illustrates possible item mounting brackets 805 that can be used with an item presentation framework, variably arranged and attached to the item presentation framework 801 with the item mounting attachment points 802, 803, 804 as located variably throughout the framework 801. Item mounting brackets 805 can be specifically designed for specific items found in the institution work or user environment. For example, a bracket 805 can be configured to support face shields, such as bracket 812. In another example, a bracket 805 can be configured to support eyeglasses or goggles, such as bracket 811. In another embodiment, a bracket 805 can be configured to support paper or cloth facemasks or gloves, such as bracket 809. Furthermore, a bracket 805 can be configured to support shoes, such as bracket 808. In yet another embodiment, a bracket 805 can be configured to support a phone, a wallet, keys, rings, and/or various other objects. For any item mounting bracket 805, the item mounting bracket 805 can include a coupling member 806, such as an aperture or opening as shown in FIG. 8, that may be located within a mounting base 807. Via the coupling member 806, the item mounting bracket slides, snaps, affixes, attaches, couples, etc. to the mounting attachment points 802, 803, 804 of the item presentation framework 801.

One embodiment provides a new and improved item disinfection system and method which employs an item hosting framework with convenient "quick change" item adapter system via universal coupling members 806 and item mounting attachment points 802, 803, 804 so that various brackets 805 can be employed for the desired disinfection cycle. The operator of the cabinet may wish to employ a mix of brackets 805 for a variety of items or a concentration of a specific brackets 805 can be coupled to the item presentation framework 801 (e.g. a batch of masks and face shields). One embodiment provides a new and improved item disinfection system and method which employs the "quick change" item adapter system via universal attachment points whereby the item adapters quickly snap into place and have a small protruding locking pin mechanism to prevent unintentional detachment.

The aforementioned mounting attachment points 802, 803, 804 may correspond to a variety of brackets 805. More specifically, one or more brackets 805 can be configured to couple with one or more of the mounting attachment points 802, 803, 804. In some embodiments, the mounting attachment points 802, 803, 804 are male members that correspond with female coupling members of the brackets 805 (e.g., the female members may be or include apertures 806). In other embodiments not shown in FIG. 8, the mounting attachment points 802, 803, 804 are female members that correspond with male coupling members of the brackets 805 (i.e., protrusions, protruding members, pins, shafts, projections, etc.). Each of the mounting attachment points 802, 803, 804 may be spaced a distance apart from an adjacent mounting attachment point 802, 803, 804. In order to correspond with the mounting attachment points 802, 803, 804, each of the male or female coupling members (e.g., aperture 806) of the brackets 805 can also be spaced apart from an adjacent coupling member 806 at the same distance. In some embodiments, the brackets 805 may include a single coupling member 806 configured to couple with one mounting attachment point 802, 803, 804. In other embodiments, the brackets 805 may include two coupling members 806 configured to couple with two mounting attachment points 802, 803, 804. In yet other embodiments, the brackets 805 may include three coupling members configured to couple with three mounting attachment points. In various embodiments including brackets 805 having multiple coupling members 806, the coupling members 806 may correspond to adjacent mounting attachment points 802, 803, 804. In other embodiments including brackets 805 having multiple coupling members 806, the coupling members 806 may correspond to mounting attachment points 802, 803, 804 that are not adjacent.

As noted above, the brackets 805 can be specifically configured for use with certain items. For example, the brackets 805 may be designed to support a particular object in a particular manner to ensure or attempt to ensure that the object is adequately exposed to UV light, a vaporized chemical solution, circulating air, etc. within the cabinet during a disinfection or sterilization operation. In some embodiments, a particular object may be supported by a plurality of brackets 805 rather than a single bracket 805, which may be necessary for large, heavy, or bulky objects. The variety of objects that can be supported by brackets 805 is highly configurable and related to various industries. For example, the brackets 805 can be configured to support medical devices, personal protective equipment, physical therapy or chiropractic equipment, electronics, sporting equipment, clothing garments and accessories, eye protection equipment, and equipment regarding various other miscellaneous categories. Even more specifically, brackets 805 can be configured to support a mobile device (e.g., cell phone, tablet computer, walkie-talkie, etc.), a length of wire (for medical equipment or otherwise), a lead vest used for x-ray examinations, shoes, a facemask, a computer keyboard, laboratory or sporting goggles, gloves, eyeglasses or sunglasses, a sports ball (e.g., basketball, medicine ball, volleyball, etc.), a foam ball, a dumbbell, a foam roller, a massage device (e.g., massage gun), and so on. Furthermore, brackets 805 may be configured for general use, such as a basket for miscellaneous items, a hook for hanging items, or otherwise. Various bracket configurations are shown in FIGS. 25A-43B, which may in some embodiments, be used in place of or in addition to brackets 805.

Thus, as alluded to above, the brackets 805 can be specifically designed for a particular object or object category. As such, the brackets 805 can be configured to support an object in a manner that maximizes the surface area of the object that is exposed to an atomized disinfectant, heat treatment, circulating air, UV light photodynamic therapy, mechanical wiping or brushing, a combination thereof, etc. within the cabinet during a disinfection and/or sterilization operation. More specifically, the bracket 805 can be configured in a manner that minimizes or substantially minimizes the number of touchpoints required to support the object. The bracket 805 can be configured in a manner that prevents or substantially prevents the bracket itself from reducing disinfectant and/or sterilization exposure on the object. For example, the bracket 805 can include a plurality of small, slender support members (as opposed to thick, bulky, large, etc. support members) configured to support and/or hold the object within the cabinet, where the slender members do not substantially obstruct atomized chemical droplets from contacting the supported object. In another embodiment, the brackets 805 can be configured to support the object in a manner that maximizes disinfectant and/or sterilization exposure on a portion of the object on which disinfection or sterilization is particularly important or necessary based on how the object is ordinarily used or what portions of the object are most likely to be exposed to bacteria, microbes, pathogens, etc. (e.g., the screen of a phone, the handle of a dumbbell, etc.).

In certain examples, a bracket 805 may be configured to support a heavy object, such as a medicine ball, portable massage device, dumbbell, kettlebell, or otherwise. Accordingly, a bracket configured to support heavy objects can include a plurality of coupling members (e.g., apertures 806) in order to increase the structural integrity of the bracket 805 when supporting a heavy object. Moreover, such brackets can be configured to provide structural integrity by, for example, having a larger cross-sectional shape than other brackets.

Brackets 805 may include visual indicators to describe their intended function (e.g., signage that indicates an intended object to support). In one embodiment, the brackets 805 are color-coded. For example, brackets 805 associated with physical therapy can be one color (e.g., green), while brackets associated with eye protection can be another color (e.g., red). Brackets 805 associated with electronics can be a third color (e.g., blue), while brackets 805 associated with personal protective equipment can be a fourth color (e.g., yellow). Brackets 805 associated with garments (e.g., shoes) can be a fifth color (e.g., white), while brackets 805 associated with miscellaneous items can be a sixth color (e.g., black). When the brackets 805 are color-coded, an operator is less likely to install an incorrect bracket in the cabinet. Accordingly, it is more likely that the correct bracket 805 will be used so that disinfection and/or sterilization efficacy is maintained at a desirable level.

Figure 9:
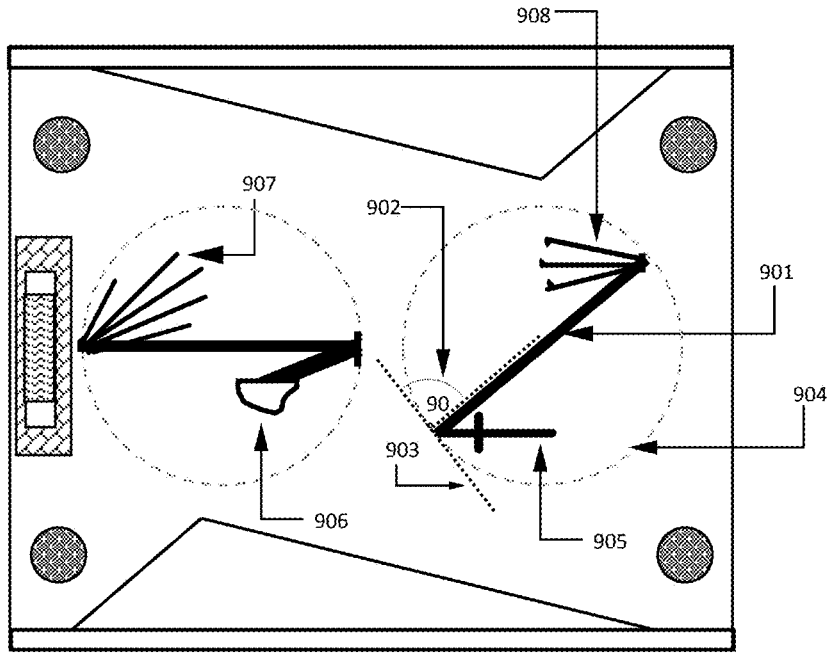
FIG. 9 illustrates a high perspective view of the internal space and item presentation to disinfection methods using the mounting bracket offset embodiment of the cabinet.

FIG. 9 illustrates the internal cabinet space and item presentation to all disinfection methods using an offset mounting bracket whereby the item presentation framework 901 moves within the carrousel movement area 904 and one or more item mounting attachments 905, 906, 907, 908 are attached to the item presentation framework 901. The attachment can be mounted with its centerline at an interior "offset angle" between 0° and 90° from parallel to the item presentation framework (shown as angle 902). The attachment can alternatively be mounted at an angle between 0° and 90° from a perpendicular line 903 whereby the item mounting attachments remain inside the carrousel movement area 904 yet are faced openly at an offset angle. When offset, items opposite each other on the item presentation framework are presented in opposing offset angles so that they do not obscure any disinfection method presentation and do not physically collide when mounted and dismounted. This can make mounting and dismounting items easier in and around the item presentation framework such that mounting or dismounting an item doesn't disturb another adjacent item. To further illustrate, within any framework or base of attachment, items mounted directly adjacent or directly opposed will force contact with one another during the mounting or dismounting effort, causing items to unintendedly touch or dismount or displace. One embodiment minimizes the opportunity for items to occlude, touch or displace each other at any time.

While FIG. 9 shows brackets mounted to two carrousels, other embodiments of the cabinet can include one carrousel or more than two carrousels. For example, the cabinet shown and described with reference to FIGS. 11-17 can include a single carrousel having a plurality of vertical columns, shafts, or posts coupled to a plurality of wings extending radially outward from a center point. In these embodiments, brackets can be mounted to the carrousel at an offset at a predefined angle (e.g., approximately 20°, approximately 30°, etc.) relative to the vertical columns, shafts, posts, etc. of the carrousel. For example, the brackets may be offset from parallel or substantially parallel to the item presentation framework 901 described above. According to an exemplary embodiment, the brackets may be offset a predefined amount (e.g., 20° plus-or-minus) 5° in a particular direction relative to the a wing of the carrousel of FIG. 11 or relative to the item presentation framework 901, as described above. The brackets may be each be offset in the same direction relative to the item presentation framework 901 (or the wing of the carrousel), such as in a clockwise direction or a counterclockwise direction, in order to further prevent any obstruction or obfuscation of one object by an object on an opposing side of the item presentation framework 901. Preventing obstruction or obfuscation further serves to bolster sterilization and/or disinfection efficacy. In other embodiments having a single carrousel, the brackets can be offset at an angle of more or less than the predefined amount (e.g., approximately) 20°.

In various embodiments, a plurality of different brackets can couple with mounting attachment points of the item presentation framework 901. In some embodiments, the mounting attachment points can comprise apertures configured to receive a male end of a bracket, as is shown and described below with reference to FIG. 23. In other embodiments, the mounting attachment points can comprise protrusions, such as fasteners (e.g., screws, bolts, hooks that are coupled with the item presentation framework 901, as is described below with reference to FIGS. 20-22. In some embodiments, each bracket may comprise a universal bracket base that can be coupled with the item presentation framework 901, while various bracket attachments configured to support a particular object are coupled with the universal bracket base (and therefore coupled with the item presentation framework 901).

Further disclosed herein is an item disinfection system and methods for making, distributing, and using the system with further embodiments.

In accordance with one embodiment, a cabinet can include a new and improved physical enclosure which is portable by one person, can be powered by a single conventional wall outlet or equivalent, self-contained as a closed system, can be operated indoors, can be operated with average personnel with little training, is quiet in operation, and has easy operator access to the enclosure interior.

In one embodiment, sensors, software and lights and screen displays serve as the control mechanisms of one embodiment to allow the operator to use, monitor, and troubleshoot the cabinet thereby assuring a safe and effective execution of the selected disinfection treatment plan.

In one embodiment, the system can be of a durable and reliable construction and may be easily and efficiently manufactured and marketed.

In one embodiment, the system can be made portable so that it can be located nearest the source of contaminants, can be optionally movable by only one person, can be configured to fit through any standard doorway, can be configured to be rolled upon wheels for easier transport, and can be configured to weigh less than 250 pounds.

One embodiment provides a new and improved item disinfection system and method that is constructed of high-grade institution-grade materials such as stainless steel, has no exposed wires, with all drive and control components located outside the disinfection area but located within the cabinet container.

One embodiment provides a new and improved item disinfection system and method that is efficient in the labor required to transport, load, and unload items for treatment as well as efficient in the time required to complete a treatment plan/cycle (generally in 15 minutes or less).

One embodiment provides a new and improved item disinfection system and method whereby the cabinet's software controls indicate the system's status whereby the operator can easily understand the status as "dirty/ready for cycle", "clean/ready to unload" with safety monitoring and messaging if a door is opened prematurely, the "dirty" door is opened before the "clean" door post-cycle, or if both "dirty" and "clean" doors are opened at the same time (these are contaminating events).

Figure 10A:
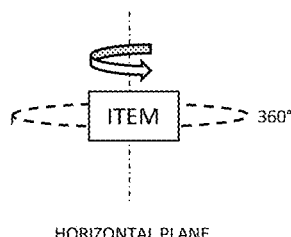
FIGS. 10A-D illustrate exposure to all disinfection methods and treatments by changing the position between item and disinfection method.
Figure 10B:
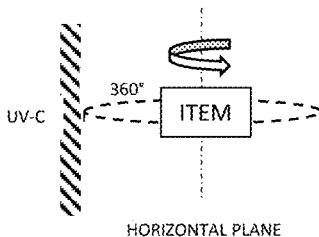
Figure 10C:
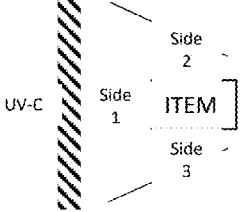
Figure 10D:
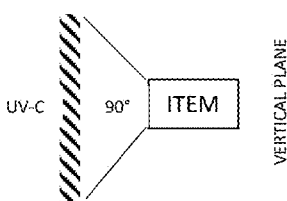

One embodiment provides a new and improved item disinfection system and method that provides 100% light-of-sight UV-C exposure by utilizing one or more UV-C sources whereby we position the item and light exposure to achieve via the item or treatment movement embodiment a 360 degree exposure on the horizontal plane that accomplishes a full exposure to all sides and surfaces of the item within a full range of movement (see FIGS. 10*b*, 10*c*).

One embodiment provides a new and improved item disinfection system and method that provides UV-C disinfection method from broad angles with a light-of-sight angle not less than 90 degrees up to 180 degrees in the vertical plane for any point of exposure facing the UV-C source, irrespective of item position within the enclosure. Further, this item presentation to the light achieves UV-C exposure to not less than 3 sides/surfaces of the item in the same instance (see FIG. 10D).

One embodiment provides a new and improved item disinfection system and method that provides a heat disinfection method whereby varying temperatures are achieve inside the enclosure for various durations to render various living contaminants inert or dead. The cabinet monitors interior temperatures to achieve a known surface temperature of the exposed items. Based upon item material sensitivities, the temperature may be increased and time decreased or temperature may be decreased and duration increased. The cabinet can reach temperatures up to 160° F. within 40 minutes or less. The addition of the rotating carrousel embodiment makes distribution of heat treatments among all items very uniform.

One embodiment provides a new and improved item disinfection system and method that provides air pressure and airflow disinfection enhancement method whereby the cabinet will maximize air pressure within the enclosure in order to increase the harshness of the environment upon living contaminants. The addition of the heat embodiment makes internal air especially effective in disinfection. The addition of the rotating carrousel embodiment makes distribution of air among all items very uniform.

One embodiment provides a new and improved item disinfection system and method that introduces and circulates a vaporized fog throughout the interior enclosure, coating all surfaces of contained items for the purpose of disinfection or freshening of appearance or smell. The amount of vaporized liquid and duration of application is controlled per the treatment plan. The liquid is a water-based chemical solution. The addition of the rotating carrousel embodiment makes distribution of atomized liquid treatments among all items very uniform.

One embodiment provides a new and improved item disinfection system and method that provides humidity disinfection enhancement method whereby the cabinet's liquid vaporization capability will increase humidity within the enclosure in order increase the harshness of the environment upon living contaminants more sensitive to heat+humidity combination. The cabinet can have the ability to apply heat+airflow+low humidity combination for maximum disinfection of one category of contaminants while separately applying heat+airflow+high humidity combination for maximum disinfection of another category of contaminants. The addition of the rotating carrousel embodiment makes distribution of heat and air and humidity treatments among all items very uniform.

One embodiment provides a new and improved item disinfection system and method that provides airflow drying enhancement method whereby the cabinet will move high volume of air across the surface of all contained items to facilitate drying of moist items and surfaces. The addition of the heat embodiment makes air more effective in moisture evaporation from item surfaces. The addition of the rotating carrousel embodiment makes distribution of air among all items very uniform.

One embodiment provides a new and improved disinfection system and method that allows pre-set or variable treatment plans that are a combination of disinfection methods, either in serial or overlapping order, with adjusted thresholds and duration (see FIG. 10E).

One embodiment provides a new and improved item disinfection system and method that has multiple sensors that serve to control the operating environment before, during, and following a treatment cycle. Use of these sensors assures the needed environmental factors are reached and maintained to assure treatment efficacy and operator safety. If any sensor indicates an incorrect status or no status, the system will not operate (see FIG. 10F).

Figure 11:
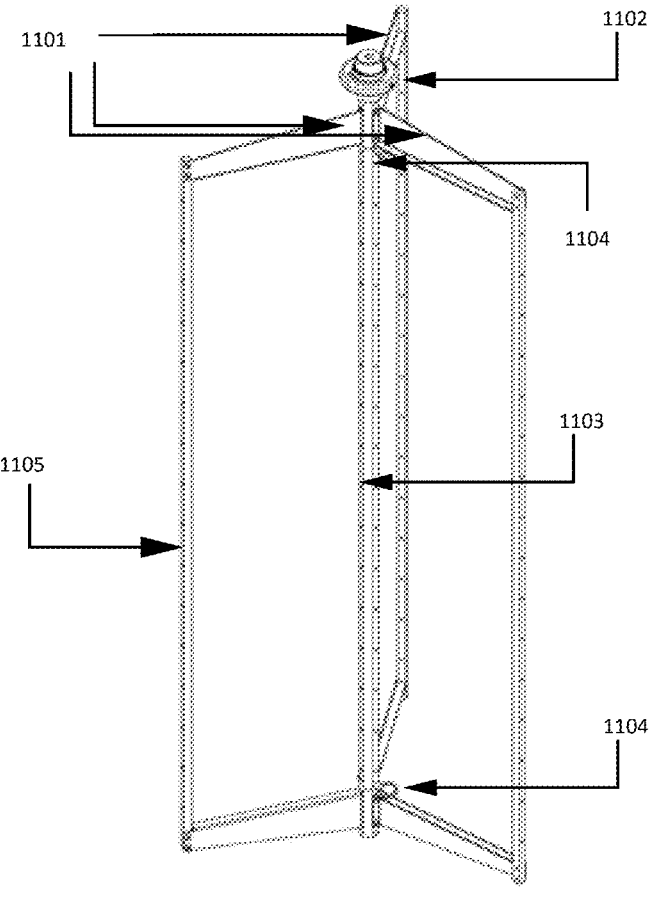
FIG. 11 illustrates a multi-wing carrousel embodiment whereby the carrousel is driven from the drive clutch.

FIG. 11 illustrates a multi-wing carrousel embodiment whereby the carrousel is driven from the drive clutch 102 that rotates the carrousel and allows for adjustable safety slippage, multiple wings 1101 connect to wing frames 1105 that provide maximum use of interior cabinet space around the center shaft 1103 which is removable to create a large interior carrousel space by removing the latch rings 1104. The multi-wing carrousel may be of unitary construction or an assembly of components coupled together. The components may include rod or beam members coupled together via one or more fasteners (e.g., screws, rivets, etc.) with or without adhesive, for example. According to an exemplary embodiment, the multi-wing carrousel can have three wings 1101. In other embodiments, the multi-wing carrousel can have fewer or more than three wings 1101. Each of the wings 1101 can be coupled to a wing frame 1105, which can be formed as a shaft, beam, post, etc. More specifically, each of the wing frames 1105 can be members that extend vertically or substantially vertical (perpendicular or substantially perpendicular relative to a horizontal plane) when installed within the cabinet and connect a top member of each wing 1101 to a bottom member of the same wing 1101. Furthermore, each of the wing frames 1105 can include a plurality of bracket mounting means (e.g., item mounting attachment points 802, 803, 804) configured to couple with a bracket for supporting an item within the cabinet, particularly during a sterilization and/or disinfection cycle. In some embodiments, one or more of the wing frames 1105 can include a plurality of apertures configured to receive a male end of a bracket, as is described below in detail with reference to FIG. 23. In another embodiment, one or more of the wing frames 1105 can include a plurality of protrusions configured to be received by an aperture of a bracket, as is described in detail below with reference to FIGS. 20-22. In such embodiments, the protrusion can be a fastener (e.g., screw, bolt, etc.) that is fastened to the wing frame 1105.

As noted above, a center post 1103 of the multi-wing carrousel assembly can be removable. More specifically, the center post 1103 can be configured to detachably couple with the multi-wing carrousel assembly at a top end and a bottom end, where each of the top end and the bottom end are coupled to the multi-wing carrousel assembly via some coupling means, shown as a latch ring 1104. In the example shown, the latch rings 1104 can be removed from the top end and the bottom end of the center post 1103, thereby decoupling the center post 1103 from the multi-wing carrousel assembly. In operation, apertures at the top and bottom of the center post 1103 may align with apertures at the top and bottom of the carrousel. When aligned, latch rings (e.g., pins, rods, etc.) may be inserted through the apertures to couple the center post 1103 to the assembly. In other embodiments, the center post 1103 can be coupled with the multi-wing carrousel assembly via some other means (e.g., spring-loaded pins, threading the center post 1103 into a nut coupled with the multi-wing carrousel assembly, etc.). In an exemplary embodiment, when the center post 1103 is removed, the multi-wing carrousel assembly can be configured to support one or more large, bulky, and/or heavy items via one or more of the wing frames 1105. In some embodiments, a large, bulky, and/or heavy item can be supported by multiple brackets coupled with a wing frame 1105. In another embodiment, a large, bulky, and/or heavy item can be supported by a plurality of brackets couple with a plurality of wing frames 1105 (e.g., a first bracket coupled with a first wing frame 1105 and a second bracket coupled with a second wing frame 1105), as is shown and described below with reference to FIG. 24.

Figure 12:
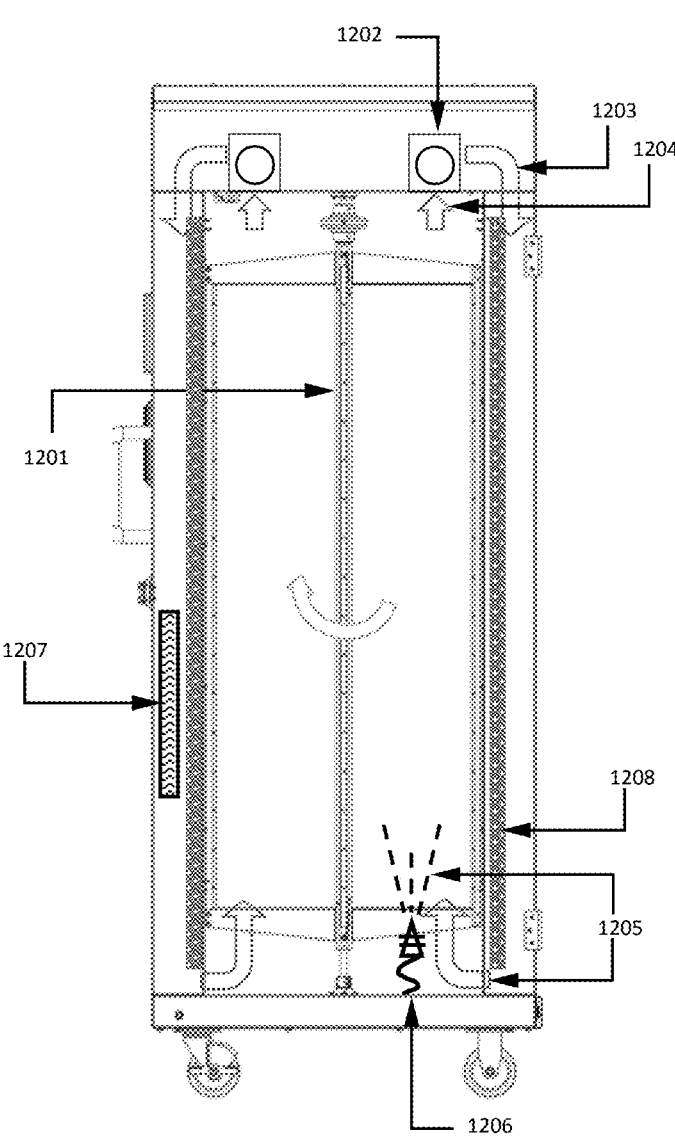
FIG. 12 illustrates a cross sectional elevation view of a four-corner embodiment where the rotating carrousel is surrounded by germicidal light sources.

FIG. 12 illustrates a cross sectional elevation view of a four-corner embodiment where the rotating carrousel 1201 is surrounded by germicidal light sources 1208 as interior air is ingested 1204 into a fan 1202 outside the interior space and air is moved into the nearest corner duct 1203 moving downward to the cabinet bottom, passing by heater 1207 and re-entering the cabinet 1205 whereby the air can force interior microbes and atomized liquid 1206 vertically while the carrousel is moving items horizontally. The resulting airflow 1205 1204 passes all along the warm surface of the germicidal light component 1208, providing a cooling effect upon the light.

Figure 13:
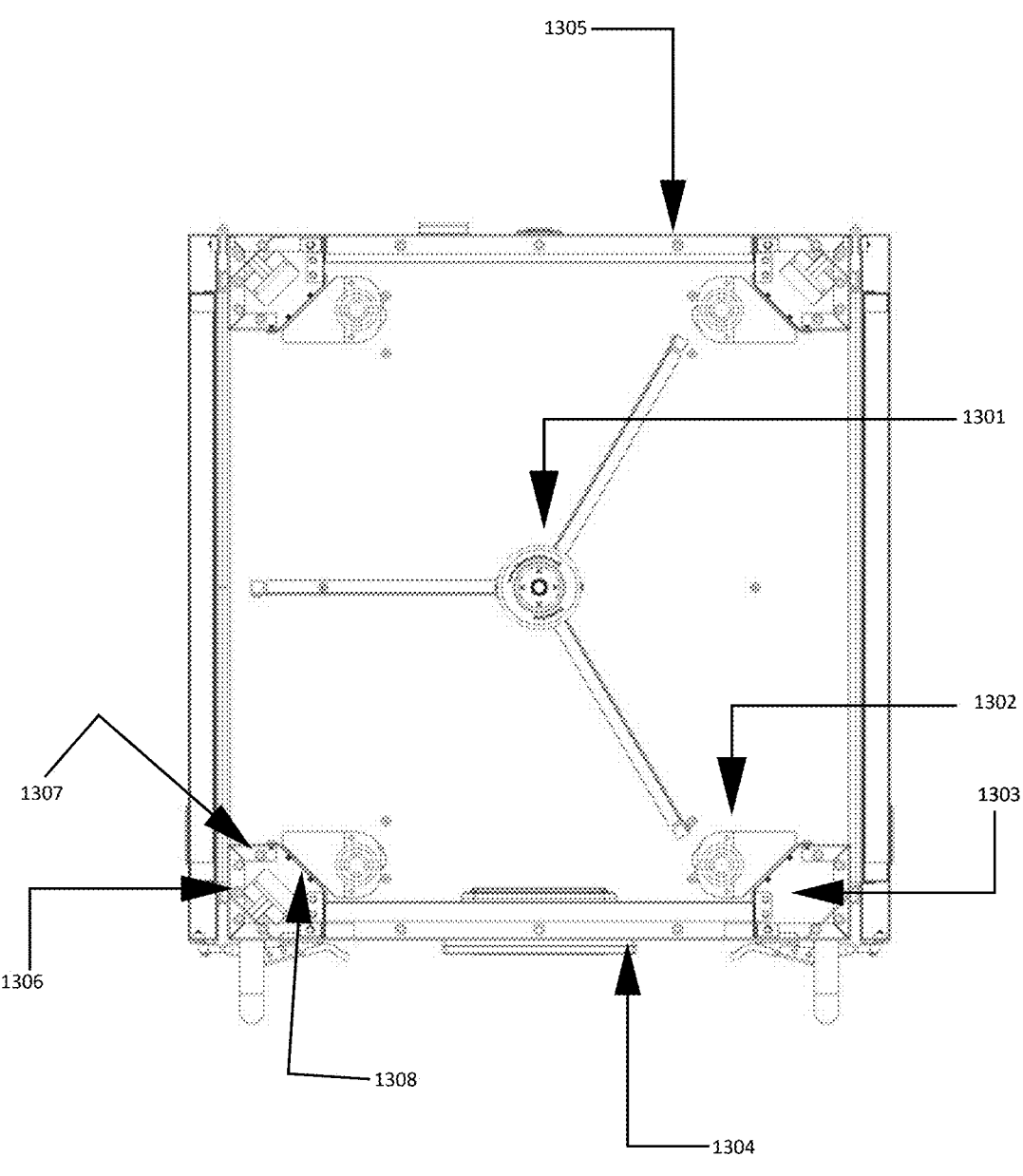
FIG. 13 illustrates a cross sectional overhead view of a four-corner embodiment where the rotating carrousel is surrounded by germicidal light sources.

FIG. 13 illustrates a cross sectional overhead view of a four-corner embodiment where the rotating carrousel 1301 is surrounded by germicidal light sources 1302 as interior air is moved into the nearest corner duct 1303 moving downward to the cabinet bottom. The corner duct 1303 can be formed in part by a front wall 1304 and/or rear wall 1305 of the cabinet, according to one embodiment. The front wall 1304 may be proximate a viewing window and handles of the cabinet, while the rear wall 1305 may be proximate a power switch and power outlet, according to one embodiment. More specifically, the front wall and the rear wall of the cabinet can comprise a C-shaped cross section whereby two ends of the front wall and rear wall curl in-wards towards an interior space or volume of the cabinet. More specifically, the front wall can include a first section 1304 and the rear wall can include a first rear section 1305. Each of the first section 1304 and the second section 1305 can include a second section 1306 extending substantially perpendicularly to the first section 1304 or 1305 (and substantially parallel to side panels or doors), and a third section extending from the second section 1306 parallel to the first section 1304, 1305. A cover or panel 1308 may be coupled with the an interior surface of the first section 1304, 1305 and the third section, thereby enclosing forming the corner duct 1303 within a portion of the first section 1304, 1305, the second section 1306, and the third section 1307. According to an exemplary embodiment, the corner duct 1303 can remain enclosed (i.e., separated from the interior or exterior of the cabinet) when a side door of the cabinet is opened. The second section 1306 and the third section 1307 may also be coupled to a top and a bottom of the cabinet to provide structural support, according to one embodiment. As discussed in further detail below with reference to FIG. 16, the corner ducts 1303 can also facilitate the circulation of air (or another fluid, as desired) throughout the cabinet, whether in connection with a disinfection or sterilization cycle or otherwise. For example, the corner ducts 1303 can facilitate the movement of air from a bottom of the cabinet to a top of the cabinet or vice versa.

Figure 14:
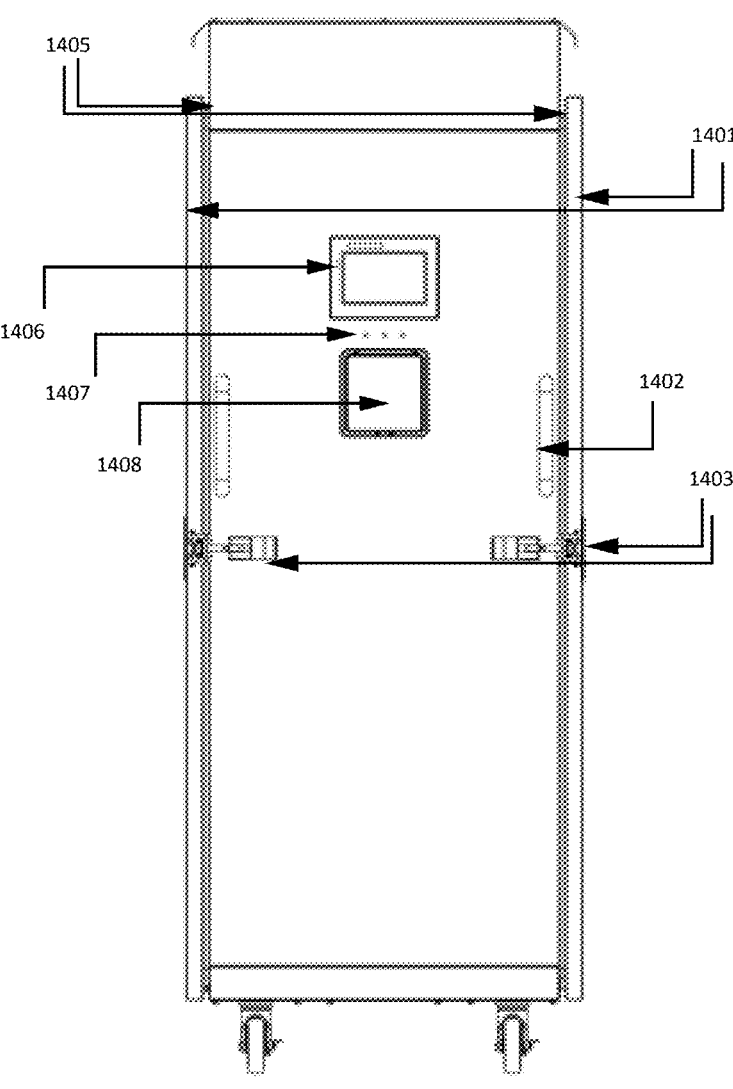
FIG. 14 illustrates a side view of a multiple access door embodiment whereby doors are located on opposite sides of the cabinet.

FIG. 14 illustrates a side view of a multiple access door embodiment whereby doors 1401 are located on opposite sides of the cabinet with a steering handle 1402 on each side, each door with a manual lock 1403. A further safety door embodiment provides an automated lock 1405 on any access door 1401. The front-facing status embodiment allows for complete machine status to be visible from the front plane 1409 containing a computer screen HMI 1406, status indicator lights 1407 and viewing window 1408 and manual door locks 1403.

Figure 15:
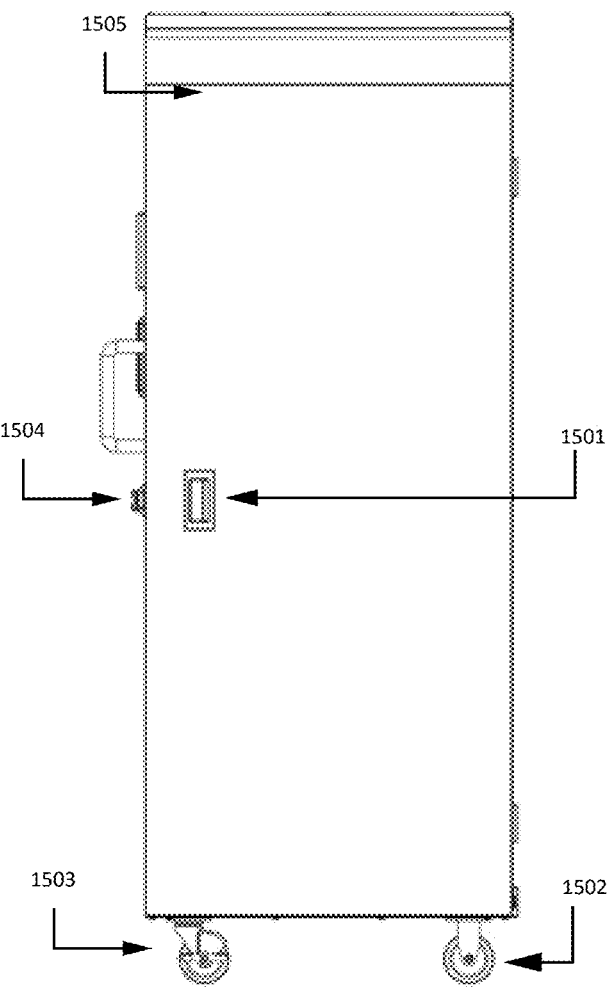
FIG. 15 shows an embodiment including a door with pull handle.

FIG. 15 shows an embodiment including a door with pull handle 1501, manual door lock 1504, automated door lock 1505, fixed wheel 1502 and steerable, lockable wheel 1503. The automated door lock 1505 can be an electromagnetic door lock positioned between the door of the cabinet and an internal structure, such as a frame of the cabinet. The automatic lock can be configured to lock the side door in response to an indication that a disinfection and/or sterilization cycle is occurring or is scheduled to occur within a predetermined amount of time. When the door is locked, the automatic lock 1505 can substantially prevent access to an interior of the cabinet until the disinfection or sterilization cycle is complete, according to one embodiment. In another embodiment, the automatic door lock 1505 can be unlocked in response to an operator command (e.g., manual override command). The automatic locks 1505 can therefore bolster the efficacy of the device by ensuring that access to the cabinet interior is not or is substantially not allowed in certain circumstances, even if an operator forgets to lock the manual lock 1504.

Figure 16:
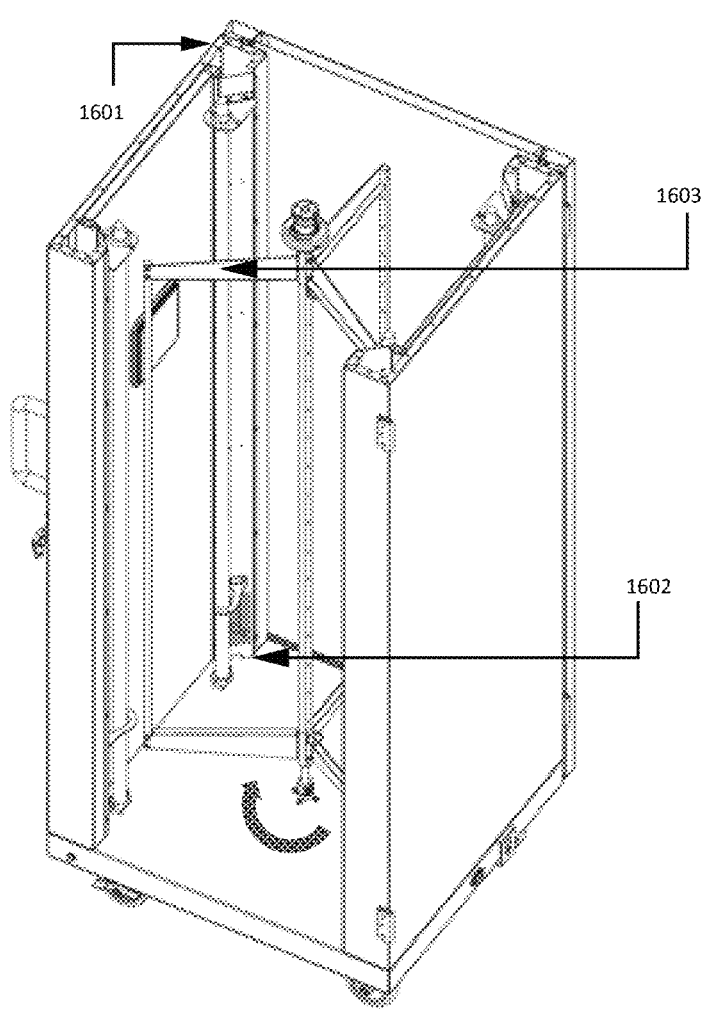
FIG. 16 illustrates a perspective cut away view of a four-corner embodiment where the cabinet's structural frame is also an air duct.

FIG. 16 illustrates a perspective cut away view of a four-corner embodiment where the cabinet's structural frame is also an air duct. More specifically, structural elements (i.e., the first section 1304, 1305, the second section 1306, and the third section 1307 shown in FIG. 13) at each corner of the cabinet's interior can be a duct for moving or circulating air throughout the cabinet interior. The duct can include a top member 1601 and a bottom member 1602. According to an exemplary embodiment, the duct extends as part of the cabinet frame the full or nearly the full length of the interior cabinet space, providing controlled airflow from top of duct 1601 to bottom of duct 1602. In another embodiment, the duct provides controlled airflow from the bottom of the duct 1602 to the top of the duct 1601. As carrousel 1603 rotates within the cabinet interior, the airflow can be moved, directed, or otherwise guided vertically from bottom to top, from top to bottom, or otherwise. In various embodiments, the duct can circulate hot, cold, room, or another desired temperature air (for example, a heater may be used to heat the air prior to circulation, a heat exchanger may be used to cool the air prior to circulation, etc.) throughout the cabinet in connection with a disinfection or sterilization cycle. The duct can also include a plurality of perforations, apertures, vents, or openings between the top of the duct 1601 and the bottom of the duct 1602 to allow air to circulate between the top 1601 and the bottom 1602. In some embodiments, the ducts can be fluidly coupled to one or more blower motors, fans, or other devices configured to generate airflow. Such devices can be fluidly coupled to the duct in a location proximate to the top 1601, proximate to the bottom 1602, or otherwise. In addition to facilitating air circulation within the cabinet, the duct as herein described can also provide structural support and rigidity for the cabinet itself. For example, the duct may be coupled to one or more adjacent walls (e.g., a front wall, back wall, bottom wall, top wall) and can act as an additional structural member within the cabinet to bolster structural rigidity thereof.

Figure 17:
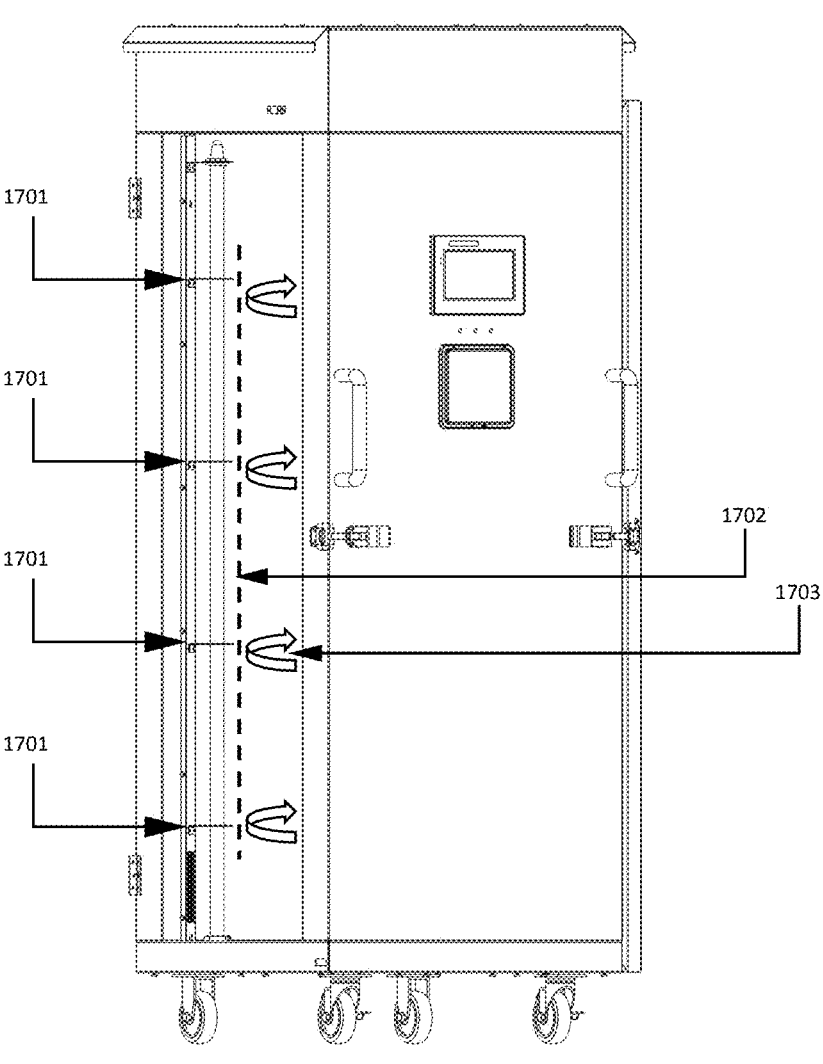
FIG. 17 illustrates an embodiment of the cabinet's internal space using item physical guides.

FIG. 17 illustrates an embodiment of the cabinet's internal space using item physical guides. As the framework carrousel moves at its center point 360° within carrousel movement area 1703 items contained within the carrousel could potentially shift outside of intended movement range 1702 whereby all or a portion of any item could extend beyond the carrousel movement area 1703 and if so, item physical guide points 1701 are positioned to protrude and nudge the item toward carrousel movement area 1703 and prevent the item from leaving the carrousel movement area 1703 where the item would be prevented from receiving or would prevent other items from receiving full treatment by chosen disinfection methods. The item physical guides provide a new and improved item disinfection system and method that has built-in physical guide material on the interior of the enclosure or door assembly whereby any item that becomes misaligned with its intended position as it rotates is nudged toward its original intended position so that it remains in place for exposure as well as it does not affect any other item or the cabinet's mechanisms. Alternatively, the item can be moved upon a conveyor or carriage and a similar physical guide can be positioned to assure the item remains in its intended position throughout the treatment cycle.

Figure 18:
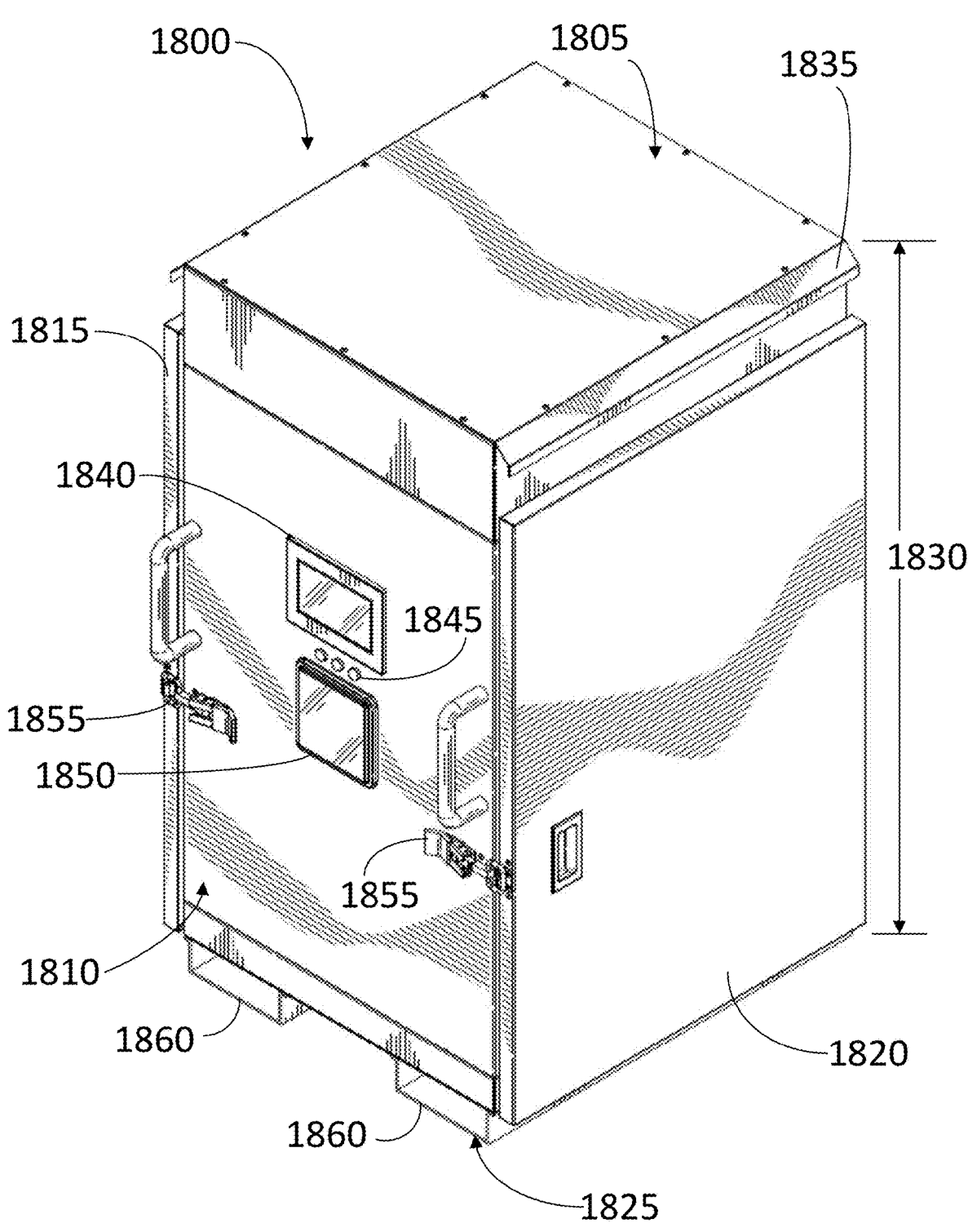
FIG. 18 is a perspective view of a disinfection and/or sterilization cabinet, according to an example embodiment.

Referring now to FIG. 18, a disinfection cabinet 1800 is shown according to another embodiment. The disinfection cabinet 1800 can include a top portion or member 1805, a front portion or member 1810, a first side door 1815 coupled to a rear portion or member, a second side door 1820 coupled to the rear portion or member, and a bottom portion or member 1825. The cabinet 1800 can include a height 1830 that spans from the top 1805 to the bottom 1825.

According to an exemplary embodiment, the height 1830 of the cabinet is less than a height of a cabinet of the embodiment shown in FIGS. 12-17. The cabinet 1800 can be configured for use on a desktop, table, countertop, or other surface that is elevated from a ground surface, for example. Because the cabinet 1800 can be used on an elevated surface, the cabinet 1800 can have a shortened height (relative to other cabinet embodiments) so that the top 1805 of the cabinet does not or likely does not interfere with a ceiling of a room or building where the cabinet 1800 is used, for example. Although the cabinet 1800 may have a shorter height 1830 than other cabinet embodiments, the interior of the cabinet can be similar to other cabinet embodiments in many respects. For example, the cabinet 1800 can include a rotating carrousel structure configured to receive one or more brackets for supporting objects during a disinfection or sterilization operation.

The top 1805 of the cabinet 1800 can further include a guard or shield 1835. The guard or shield 1835 can be configured to prevent rain or other materials (e.g., debris, dust, etc.) from entering or likely entering the top 1805 of the cabinet 1800 and interfering with electronics or mechanical devices housed within the top 1805 and associated with operation of the cabinet 1800. Beneficially, the cabinet 1800 may be disposed in outdoor environments with the electronics of the cabinet substantially shielded from various environmental conditions (e.g., rain, etc.). In some embodiments, the cabinet 1800 can be used in military environments where exposure to elements (i.e., debris, dust, vibrations, etc.) may be prevalent. Accordingly the guard or shield 1835 can protect the cabinet 1800 from certain elements to ensure the cabinet 1800 operates at a desired efficacy level.

The front portion or member 1810 can include a display device 1840, one or more indicators 1845, and can define a viewing window 1850. In one example, the display device 1840 can include or be a touch screen device that is configured to receive an input from a user related to the operation of the cabinet 1800 and/or provide one or more graphical user interfaces. More specifically, a user may initiate a disinfection or sterilization cycle, stop the initiated cycle, monitor progress of the initiated cycle, and/or modify a disinfection or sterilization cycle of the cabinet 1800 as discussed above. The display device 1840 may also display a current status of a disinfection or sterilization cycle, such as an amount of time remaining for the cycle, a current stage of the cycle, etc. The indicators 1845 are configured to provide a visual and/or audible indication of a current status of the cabinet 1800, the objects within the cabinet that are subject to the disinfection or sterilization cycle, and/or a combination thereof. In one example, the indicators 1845 can include three lights where each light can be configured to indicate a status of the objects within the cabinet 1800. The lights may be LED lights or another type of light-emitting source. For example, a red light can indicate that the objects within the cabinet 1800 have not been sterilized or disinfected, a yellow light can indicate that the objects within the cabinet are currently undergoing a disinfection or sterilization, and a green light can indicate that the objects within the cabinet 1800 have been successfully disinfected or sterilized (i.e., that the cycle is complete). The indicators 1845 may thus provide a clear and substantially unambiguous visual indication to an operator or attendant of the cabinet 1800.

The viewing window 1850 can be configured to allow an operator to view an interior of the cabinet 1800, according to an exemplary embodiment. Because UV light may be used within the cabinet to disinfect and/or sterilize, the viewing window 1850 may be coated or otherwise treated to prevent harm to the eyes of an individual viewing the interior of the cabinet during a disinfection or sterilization cycle.

The cabinet 1800 can also include two or more latches 1855 that are configured to prevent or substantially prevent an operator from accessing an interior chamber of the cabinet 1800 via doors 1815, 1820. In some embodiments, the latches 1855 can be manually operated latches that are actuated by an operator. In another example, the latches 1855 may be automatically locking locks. For example, the latches 1855 can be electro-magnetic or electromechanical latches that lock in response to a received electrical current, where the electrical current can be received when a disinfection and/or sterilization cycle is initiated. More specifically, an electromagnetic lock may energize mating magnetic surfaces on the side door 1820 or 1815 and the front portion member 1810. In another embodiment, the automatic lock may be a solenoid-actuated lock that is activated to cause the movement of the latch into a latch receptacle to lock the door to the cabinet 1800. Accordingly, the doors 1815 and 1820 may be locked when a disinfection or sterilization cycle is in process.

The bottom 1825 of the cabinet 1800 may include a plurality of slots 1860. The slots 1860 can be configured to receive tines of a hand-operated fork truck, a fork lift, a telehandler, or other equipment with fork tines, for example. According to one embodiment, the bottom 1825 can include slots 1860 instead of any wheels or rollers. In another embodiment, the bottom 1825 can also include wheels, rollers, casters, etc. that allow the cabinet 1800 to be pushed or rolled along a surface. The bottom member or portion 1825 can also include friction-adding elements (e.g., rubberized feet) that are configured to prevent the cabinet 1800 from sliding or moving on a surface. In another embodiment, the bottom member or portion 1825 may further include various fixtures or brackets configured to fixedly couple the cabinet 1800 to a surface via fasteners, an adhesive, welding, etc.

Figure 19:
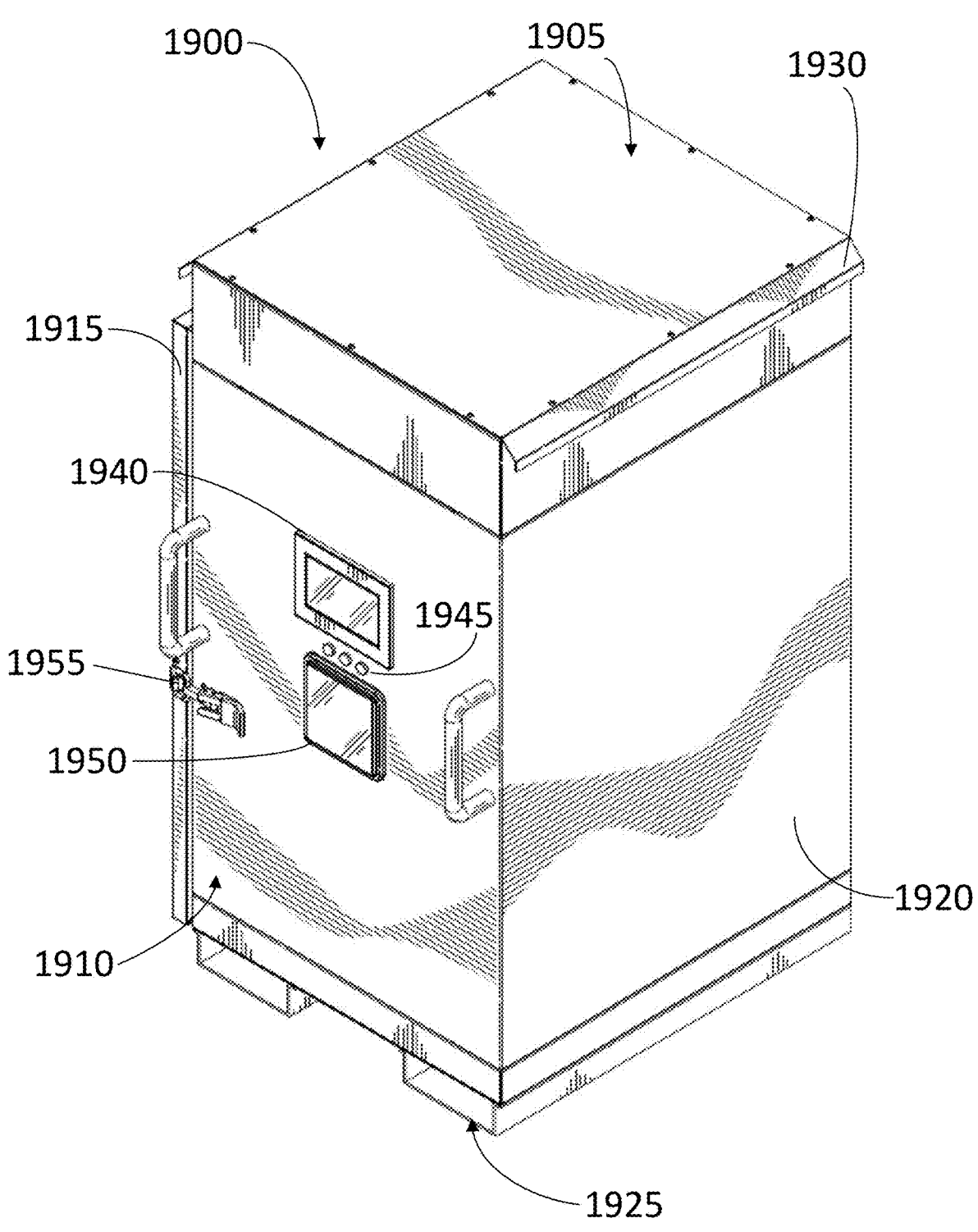
FIG. 19 is a perspective view of a disinfection and/or sterilization cabinet, according to another example embodiment.

Referring now to FIG. 19, a disinfection cabinet is shown, according to yet another embodiment. The cabinet 1900 is shown to include a top portion or member 1905, a front portion or member 1910, a first door 1915 coupled to a rear portion or member, a side panel 1920 coupled to the rear portion or member and the front portion or member 1910, and a bottom 1925. The top portion or member 1905 of the cabinet 1900 is also shown to include a guard or shield 1930 that may be coupled to the top portion 1905 (e.g., via one or more fasteners, such as rivets, screws, etc.) or be integral with the top portion 1905. The guard or shield 1930 is configured to prevent rain or other materials (e.g., debris, dust, etc.) from entering the top portion or member 1905 of the cabinet 1900 and potentially interfering with any electronics or mechanical devices housed within the top portion or member 1905 and associated with the operations of the cabinet 1900.

The front portion or member 1910 is shown to include a display device 1940, an indicator 1945, and defining a viewing window 1950. In some embodiments, the display device 1940 can be similar to the display device 1840 of the cabinet 1800 discussed above and shown in FIG. 18. For example, the display device 1940 can be or include a touch screen device that is configured to receive an input from a user related to the operation of the cabinet 1900 and provide one or more graphical user interfaces. In some embodiments, the indicators 1945 can be configured to provide a visual and/or audible indication of an operational status of the cabinet 1900, objects within the cabinet 1900 that are subject to the disinfection or sterilization cycle, and/or a combination thereof. The viewing window 1950 can be configured to allow an operator or an attendant to view an interior of the cabinet 1900, according to an exemplary embodiment. Because UV light may be used within the cabinet to disinfect and/or sterilize, the viewing window 1950 may be coated or otherwise treated to prevent harm to the eyes of an individual viewing the interior of the cabinet during a disinfection or sterilization cycle.

The first door 1915 of the cabinet 1900 is movably coupled to the cabinet 1900 (particularly, the rear portion or member) (e.g., via a hinge or other means that enables the door to move relative to the cabinet 1900). The first door 1915 is movable, and particularly rotatable, between a first or closed position that prevents access to an interior chamber or space of the cabinet 1900 and a second or open position where the door 1915 is spaced apart from the cabinet 1900 to provide access to an interior chamber of the cabinet 1900. The first door 1915 can include or be coupled to a latch 1955 that, when in a latched (i.e., locked or closed) state can prevent the first door 1915 from opening (i.e., retaining the door in the first position). Rather than having a second door positioned on an opposite side from the first door 1915 (like the cabinet 1800), the cabinet 1900 can include a side panel 1920. The side panel 1920 may be rigidly coupled with and/or integral with the front panel or portion 1910 and a back panel or portion of the cabinet 1900. The side panel 1920 therefore does not provide access to the interior of the cabinet 1900. The interior space of the cabinet 1900 can therefore only be accessed via actuation of the single door 1915, according to an exemplary embodiment. While the door 1915 is shown on a left side of the cabinet 1900 in FIG. 19, in various examples, the first door 1915 can instead be positioned on the right side (in place of panel 1920), on the rear portion or member (i.e., opposite side of the front portion or member 1910 shown in FIG. 19), or on the front side. With respect to the front side configuration, the viewing window 1950, indicator 1945, and/or display device 1940 may be coupled to the door 1915 such that they are movable fore and aft relative to the interior space of the cabinet 1900 based on movement of the door 1915.

Referring now to FIG. 20, a universal bracket base 2000 is shown, according to an example. As discussed above, the disinfection cabinet can be configured to couple with one or more brackets that support various objects within the cabinet. Each of the brackets can include a universal bracket base or support member 2000, according to an exemplary embodiment. The universal bracket base 2000 can be configured to couple with an interior framework of a cabinet, such as a carrousel similar to that shown in FIGS. 8, 9, 11, and 24, for example. The universal bracket base 2000 is configured to couple to one or more brackets or bracket attachments to support one or more objects within the cabinet to undergo or experience a disinfection and/or sterilization cycle. In some embodiments, the one or more bracket attachments (or "support members") can be detachably coupled with the universal 2000 base. Accordingly, the universal base may remain coupled to the interior framework (particularly, the carrousel) while one or more bracket attachments are coupled with or decoupled from the universal bracket base 2000. In other embodiments, the bracket attachments can be fixedly coupled with or integrally formed with the universal bracket base 2000 such that the bracket attachment is not removable from the universal bracket base 2000.

The universal bracket base 2000 can include one or more couplers or coupling structures 2005. The coupling structures 2005 are configured to facilitate the coupling of the universal bracket base 2000 to an interior framework or frame of a cabinet, namely a protrusion or aperture of the interior framework as described above with reference to FIGS. 7 and 8. For example, the coupling structures may be apertures or openings that are configured to receive a protrusion, protruding member, pin, shaft, fastener, peg, etc. of a rotating carrousel of a cabinet. More specifically, the carrousel can have a plurality of wings extending radially from a center point and columns, posts, or shafts coupled to a distal end of the wings and extending vertically in a downwards direction (i.e., perpendicular or substantially perpendicular to a horizontal plane), where each of the columns, posts, or shafts can have a plurality of protrusions, protruding members, pins, shafts, fasteners, etc. that are received by the coupling structures 2005 (i.e., an aperture). In another example, the coupling structure coupled be a protrusion, protruding member, pin, shaft, fastener, etc. that is configured to be received by one or more apertures defined by the aforementioned columns, posts, or shafts of a rotating carrousel. In the example shown, the coupling structures 2005 are structured as apertures or openings 2010. The opening 2010 is shown to include a first opening 2015 having a first diameter 2035 that flows into a second opening 2020 having a second diameter 2040. According to one embodiment, the first diameter 2035 is greater than the second diameter 2040. The first opening 2015 and the second opening 2020 collectively form the opening 2010. In various embodiments, the first opening 2015 and the second opening 2020 can have the same or a similar shape (e.g., a circular, semi-circular, or curved shape). In other embodiments, the first opening 2015 and the second opening 2020 can have a different shape (e.g., the first opening 2015 can be circular shaped while the second opening 2020 has a rectangular shape).

The coupling structures 2005 of the universal bracket base 2000 are also shown to include one or more protrusions 2025 (e.g., projections, notches, etc.) extending into the opening 2010 and, in the example shown, located between the first opening 2015 and the second opening 2020. In the example shown, the coupling structures 2005 include two protrusions 2025 positioned on opposing sides of the opening 2010 relative to each other. Ends of each of the two protrusions 2025 are separated by a protrusion distance 2045. According to an exemplary embodiment, the protrusion distance 2045 is less than the second diameter 2040 of the second opening 2020. As a result, the protrusions 2025 narrow the opening 2010. More specifically, the opening 2010 can be at its narrowest between the protrusions 2025.

The universal bracket base 2000 may further include one or more bracket attachment (or support member) coupling structures, also referred to as bracket couplers 2050. In the example shown, the bracket couplers 2050 are structured as openings or apertures 2050 defined by the base 2000. In other embodiments, different types of bracket couplers may be employed in addition to or in place of the apertures or openings 2050 (e.g., mechanical fasteners, such as screws or bolts may be employed, the brackets may be integral with the universal base 2000, a bonding agent may be used to couple the brackets to the base 2000, etc.). Each aperture is structured to receive a projection of a bracket attachment to support the bracket attachment and couple the bracket attachment to the base 2000. As noted above, the universal bracket base 2000 can be configured to couple with one or more bracket attachments. The bracket attachments can be configured to support one or more objects positioned within a disinfection and sterilization cabinet as herein described (e.g., cabinet 1800 and 1900). Example bracket attachments (also referred to as support members), bracket bases, and bracket couplers are shown and described with respect to FIGS. 25A-42B herein.

In some embodiments, the bracket attachment or support bracket may be a hook configured to support a lab coat or other hanging item. In another example, the support bracket can be a small basket configured to support miscellaneous small items (e.g., jewelry, fitness bands, ear buds, etc.). In yet another example, the support bracket may be a plurality of hooks configured to support a dumbbell. The support bracket may be specifically designed to support a particular object. For this reason, certain support brackets may not be compatible with certain objects. Therefore, it may be necessary for the support bracket to be changed as a certain object is placed within the cabinet. To facilitate convenient and rapid changing of bracket attachments, the universal bracket base 2000 may be configured to remain coupled with an interior framework of the cabinet (as discussed in further detail below with reference to FIGS. 21 and 22) while the bracket attachment or support bracket is changed.

In the example shown, the universal bracket base 2000 is primarily rectangular in shape, includes two coupling structures 2005 configured to enable coupling of the universal bracket base 2000 to an interior framework or frame of a cabinet, and includes four bracket couplers 2050 for coupling to one or more support brackets for supporting one or more objects within the cabinet. In one embodiment, one support bracket is coupled to one universal base 2000 (e.g., via at least one projection being received by at least one bracket coupler 2050). In another embodiment, more than one support bracket is coupled to one universal base 2000. For example and with reference to FIG. 20, a first support bracket may include two projections that are received by the left most bracket couplers 2050 while a second support bracket may include two projections that are received by the right most bracket couplers 2050. Alternatively, the two top most bracket couplers 2050 may couple to the first support bracket while the two bottom-most bracket couplers 2050 may couple to the second support bracket. Given this configurability, the bracket base 2000 may also be highly configurable: have a different shape than the depicted rectangular shape; include less than or more than four bracket couplers 2050; include less than or more than two coupling structures 2005; include different shapes, sizes, and/or types of bracket couplers 2050 and/or coupling structures 2005; and so on. Thus, the depicted configuration is exemplary only with other variations possible.

Referring now briefly to FIGS. 25A-42B, example bracket attachments or bracket assemblies are shown, are shown according to various example embodiments. In these embodiments, a bracket base is coupled to a support member to form a bracket attachment assembly. The assembly may be coupled to the frame or other internal framework of the cabinet. In other embodiments, the support member(s) and bracket base may be of integral construction (a unitary component).

Figure 25A:
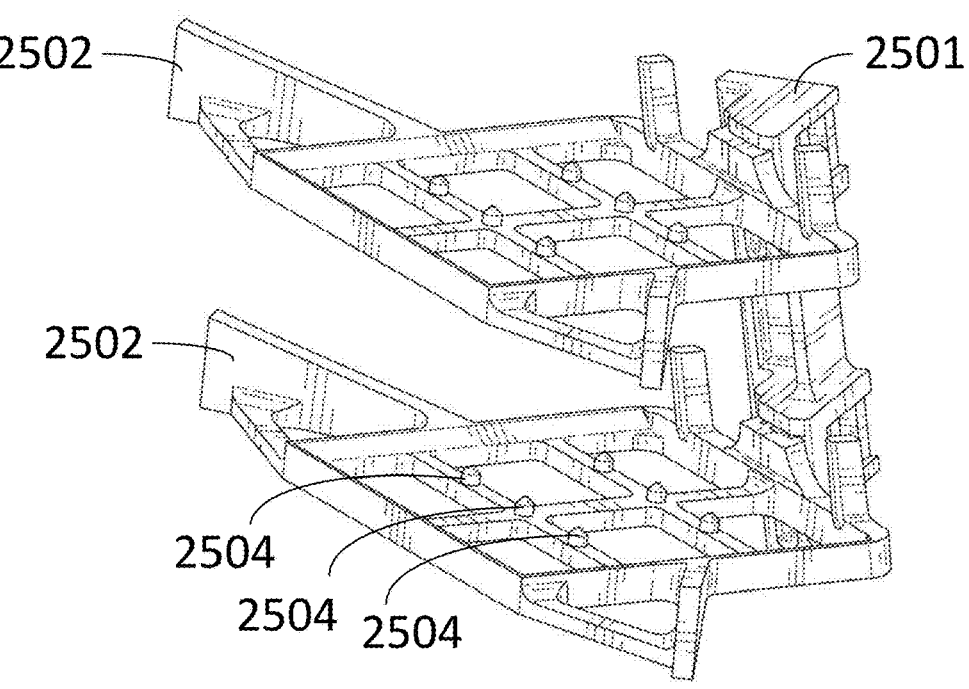
FIGS. 25A and 25B are a front (FIG. 25A) and rear (FIG. 25B) perspective views of a bracket, according to an example embodiment.
Figure 25B:
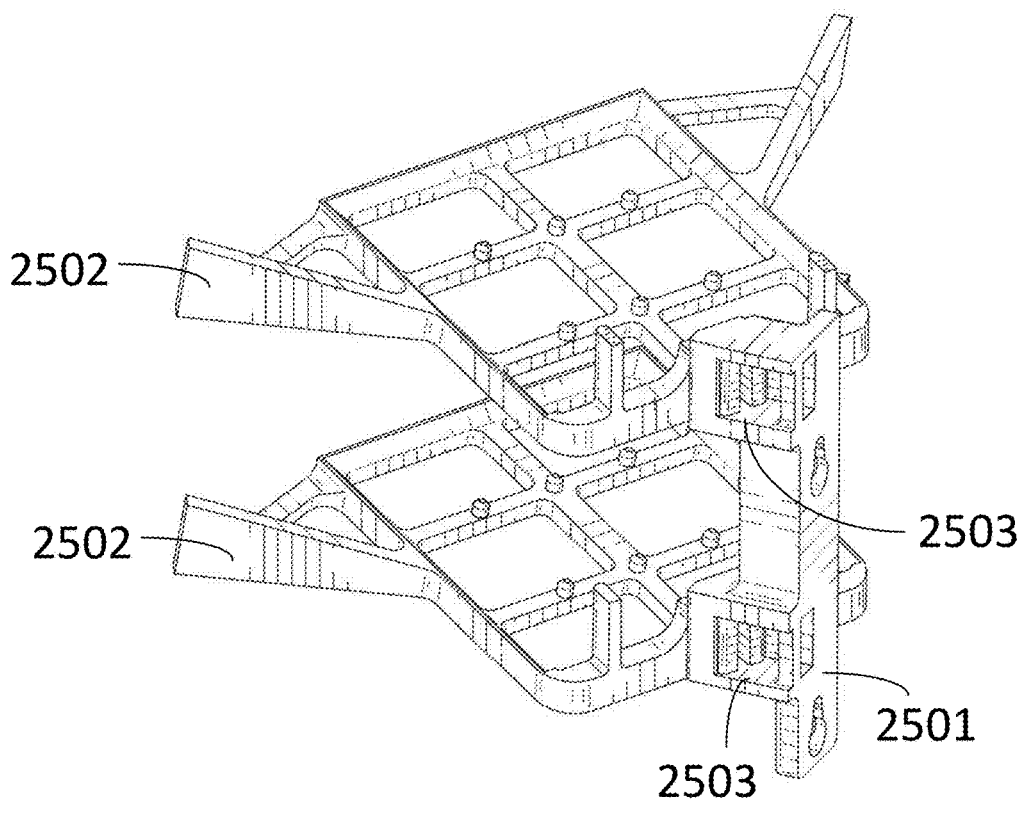

FIGS. 25A-25B show front and rear perspective views of an example bracket assembly that may be used to support a mobile phone (or other mobile electronic or other equipment), according to an example embodiment. FIGS. 25A-25B shows the bracket assembly including a bracket base 2501, support members 2502 coupled to and extending outward and away from the base 2501, and a plurality of bracket couplers 2503 of the bracket base 2501 configured to couple to the support members 2502 (e.g., apertures that receive projections of the support members 2502). The support members 2502 are configured to support one or more objects (in this case, a mobile device but other objects are conceivable). In the example shown, the support members 2502 include a plurality of low-contact touchpoints or objects 2504, which are shown in this example as projections with a pyramidal shape.

Figure 26A:
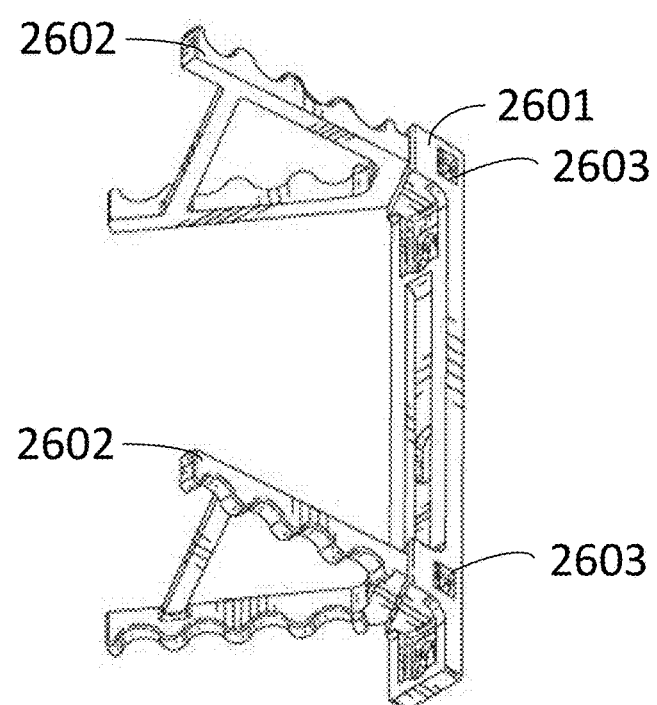
FIGS. 26A and 26B are front (FIG. 26A) and rear (FIG. 26B) perspective views of a bracket, according to another example embodiment.
Figure 26B:
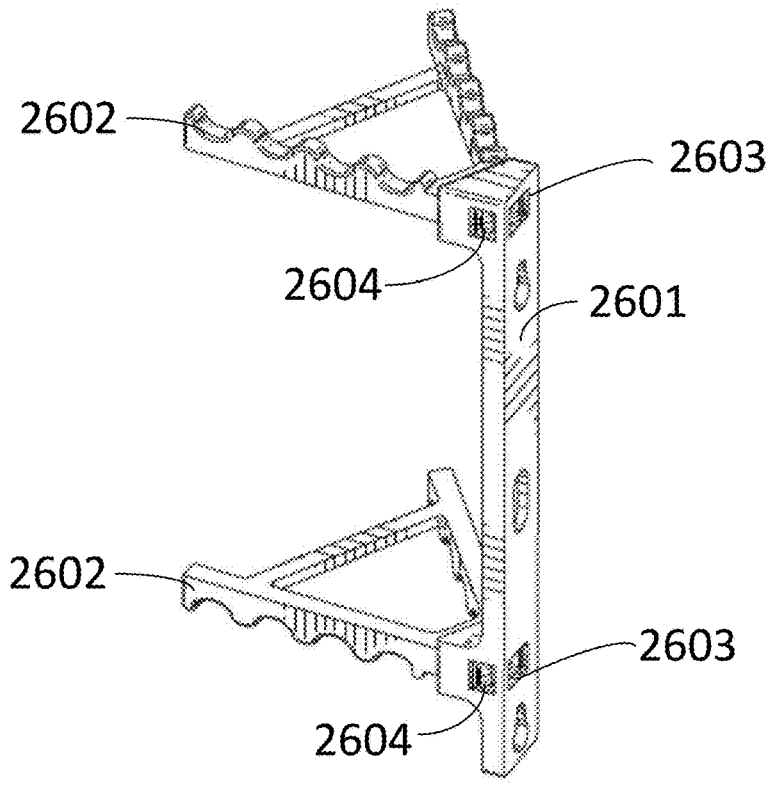

FIGS. 26A-26B show front and rear perspective views of an example bracket assembly that may be used to support a wire (or other type of flexible object), according to an example embodiment. FIGS. 26A-26B show the bracket assembly including a bracket base 2601, support members 2602 coupled to and extending outward and away from the base 2601, and a plurality of bracket couplers 2603 of the bracket base 2601 configured to couple to the support members 2602 (e.g., apertures that receive projections of the support members 2602). The support members 2602 define a plurality of ridges that may support multiple objects, such as multiple wires.

Figure 27A:
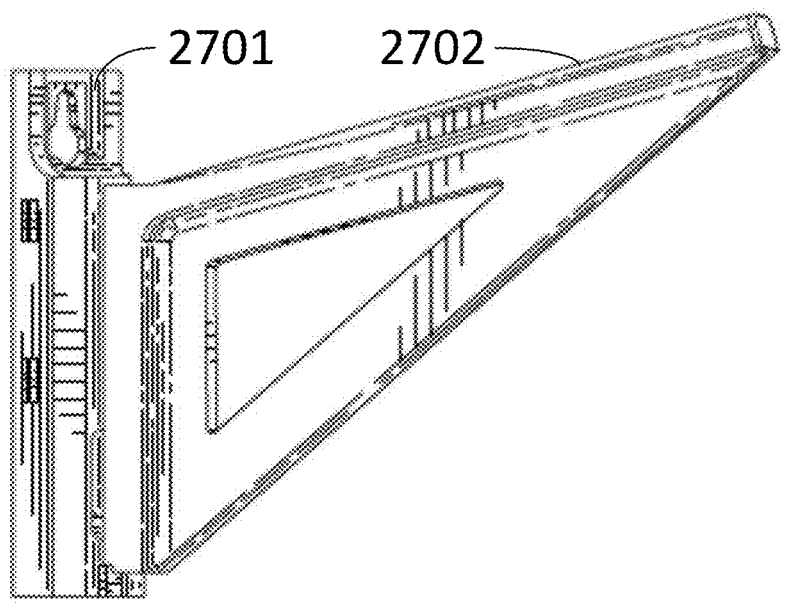
FIGS. 27A and 27B are front (FIG. 27A) and rear (FIG. 27B) perspective views of a bracket, according to still another example embodiment.
Figure 27B:
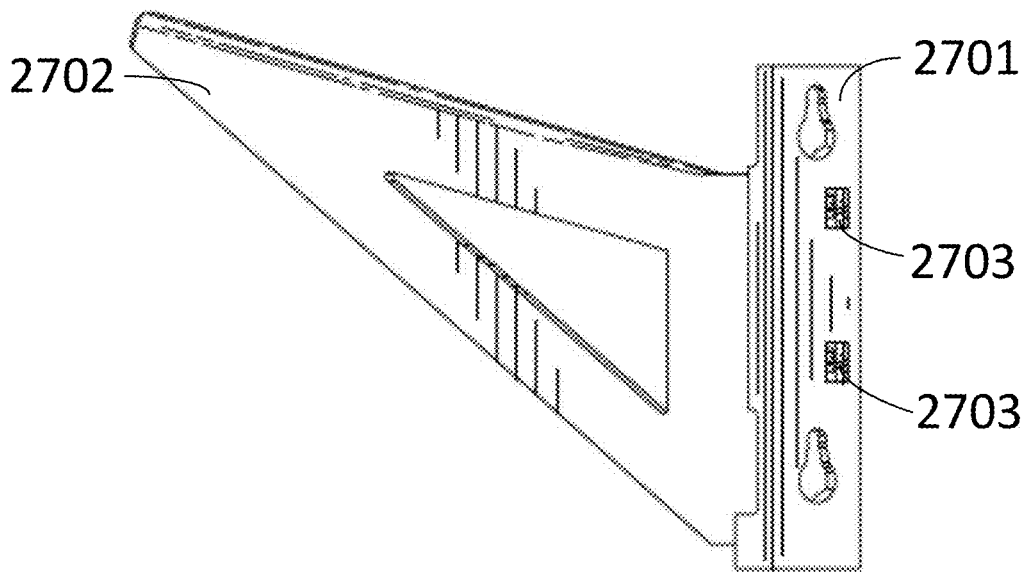

FIGS. 27A-27B show front and rear perspective views of an example bracket support member that may be used to support a garment, such as a lead vest, according to an example embodiment. FIGS. 27A-27B show the bracket assembly including a bracket base 2701, a support member 2702 coupled to and extending outward and away from the base 2701, and a plurality of bracket couplers 2703 that couple the support member 2702 to the base 2701 (e.g., apertures that receive projections of the support members 2702).

Figure 28A:
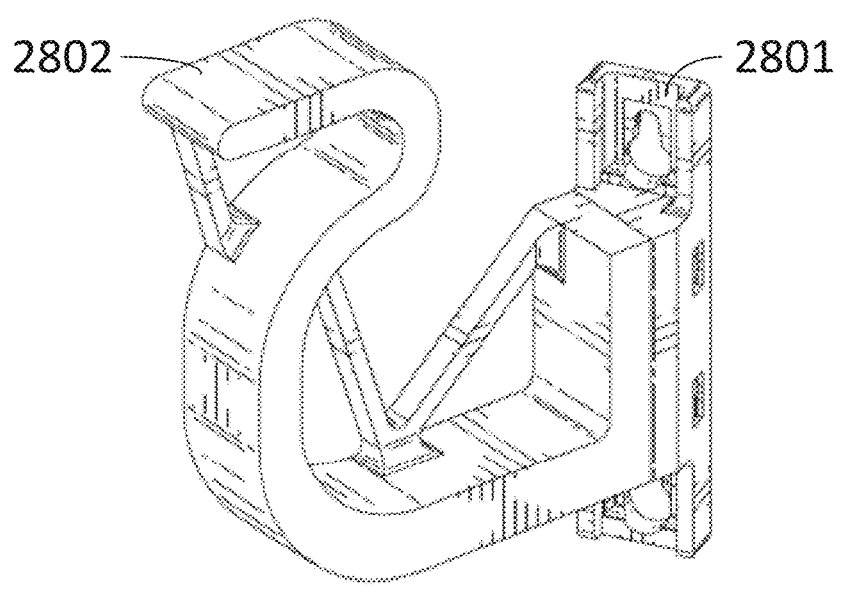
FIGS. 28A and 28B are front (FIG. 28A) and rear (FIG. 28B) perspective views of a bracket, according to yet another example embodiment.
Figure 28B:
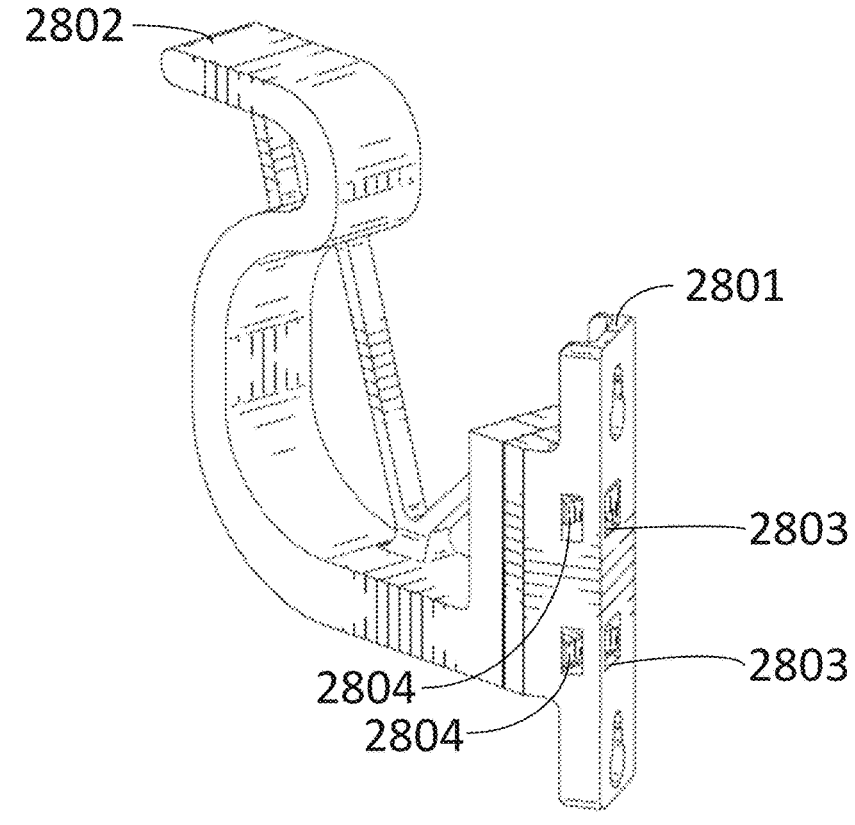

FIGS. 28A-28B show front and rear perspective views of an example bracket assembly that may be used to support a shoe, according to an example embodiment. FIGS. 28A-28B show the bracket assembly including a bracket base 2801, a support member 2802 defining a primarily S-shaped structure coupled to and extending away from the base 2801, and a plurality of bracket couplers 2803 that are used to couple the support member 2802 to the base 2801. In this regard, the support member 2802 can include a projection 2804 configured to be received by the bracket couplers 2803, which are shown as apertures or openings.

Figure 29A:
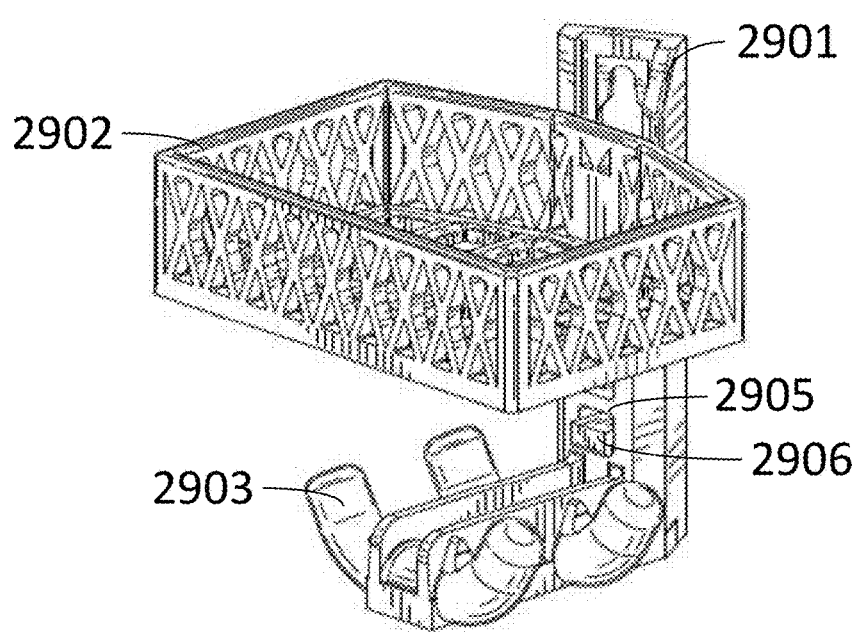
FIGS. 29A and 29B are front (FIG. 29A) and rear (FIG. 29B) perspective views of a bracket, according to yet another example embodiment.
Figure 29B:
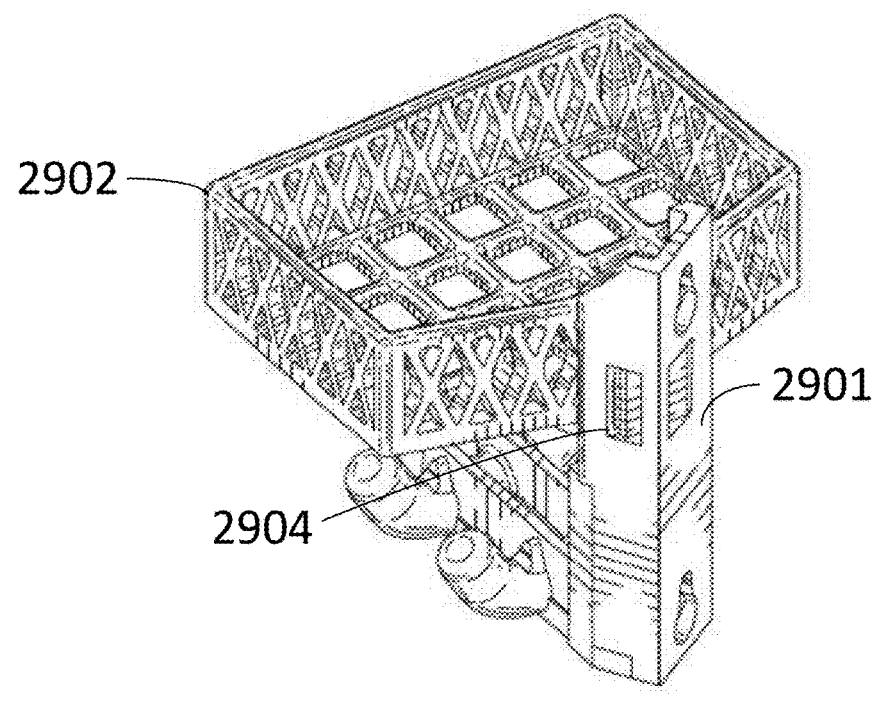

FIGS. 29A-29B show front and rear perspective views of an example bracket assembly that may be used to support rings and miscellaneous items (e.g., jewelry, keys, etc.), according to an example embodiment. FIGS. 29A-29B show the bracket assembly including a bracket base 2901, a first support member 2902 coupled to and extending away from the base 2901, a second support member 2903 coupled to and extending away from the base 2901 and positioned vertically beneath the first support member 2902, a first bracket coupler 2904 of the base 2901, and a projection 2906 of the base 2901. The second support member 2903 may define a second bracket coupler 2905 of that is configured to receive the projection 2906 of the base 2901. This assembly shows the usage of two different types of support members coupled to one base.

Figure 30A:
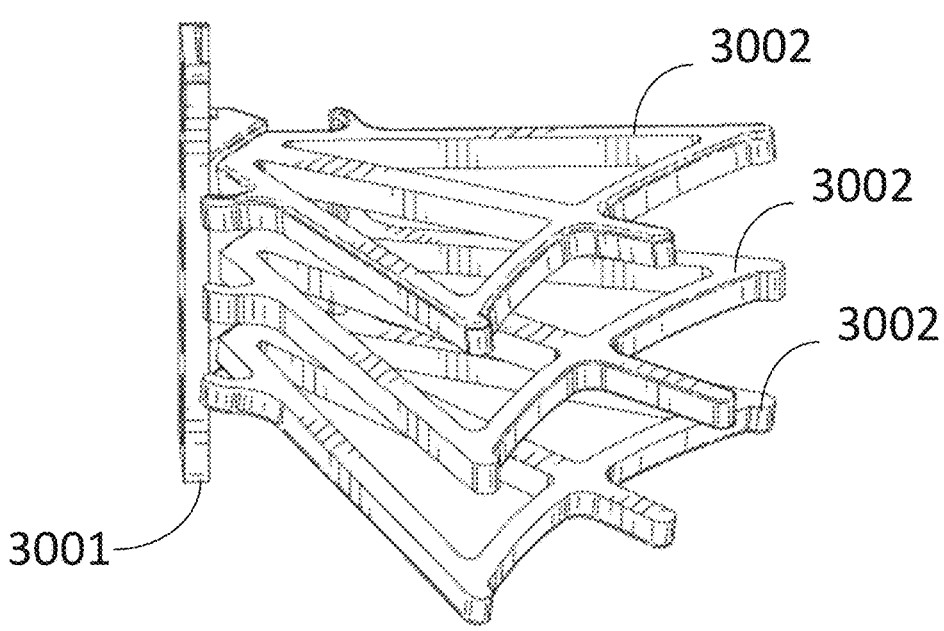
FIGS. 30A and 30B are front (FIG. 30A) and rear (FIG. 30B) perspective views of a bracket, according to yet another example embodiment.
Figure 30B:
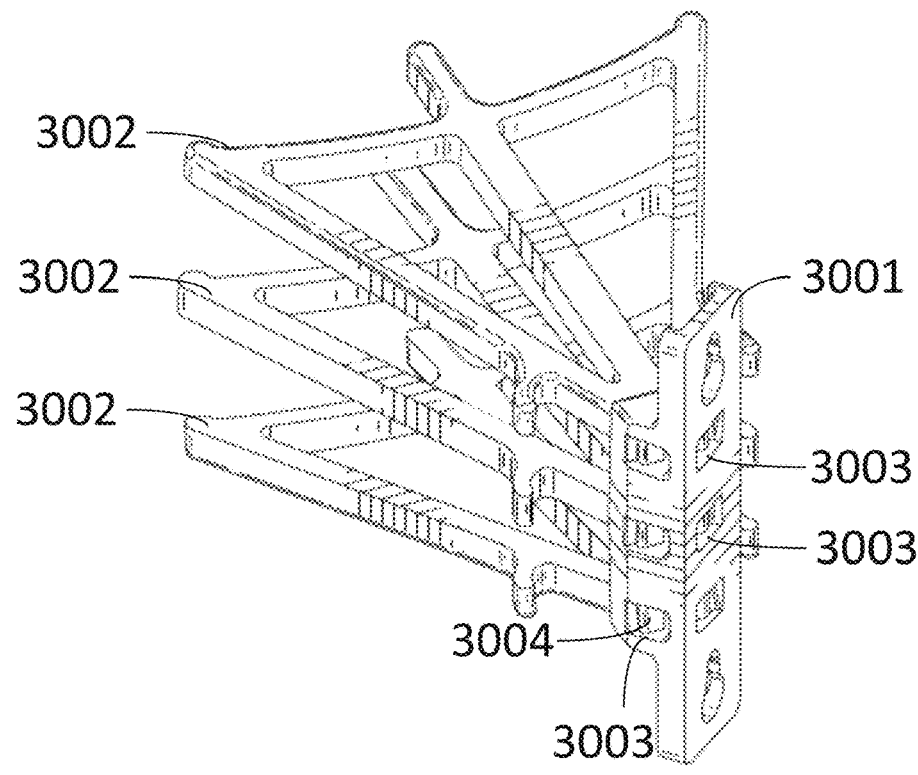

FIGS. 30A-30B show front and rear perspective views of another example bracket assembly that may be used to support a facemask or other personal protective equipment (PPE), according to an example embodiment. FIGS. 30A-30B show the bracket assembly including a bracket base 3001, a plurality of support members 3002, and a plurality of bracket couplers 3003. The plurality of support members 3002 includes at least one projection 3004 that is configured to be received by the bracket couplers 3003 of the base 3001, which are shown as apertures.

Figure 31:
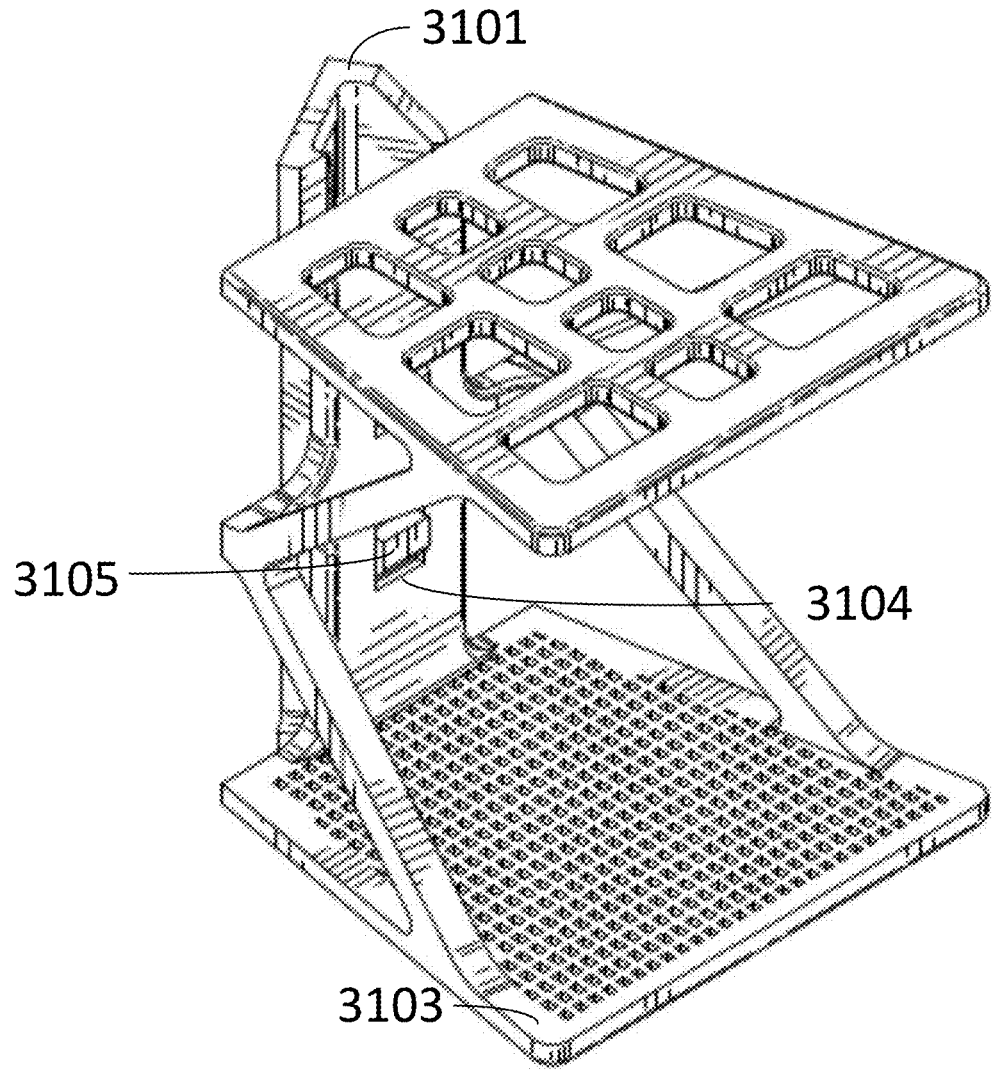
FIG. 31 is a front perspective view of a bracket, according to still another example embodiment.

FIG. 31 shows a front perspective view of another example bracket assembly that may be used to support various miscellaneous items, such as electronic devices, bottles, etc. according to an example embodiment. FIG. 31 shows the bracket assembly including a bracket base 3101, a first support members 3102, a second support member 3103, and at least one projection 3105 extending from the base 3101 in substantially a same direction as the first support member 3102 and the second support member 3103. The first support member 3102 and the second support member 3103 can define at least one coupler 3104, shown as an aperture. The coupler 3104 is configured to receive the projection 3105 of the base 3101, according to one embodiment. In the example shown, the first support member 3102 includes a plurality of openings and the second support member 3103 also includes a plurality of openings that are relatively smaller in cross-sectional size than the openings of the first support member 3102.

Figure 32A:
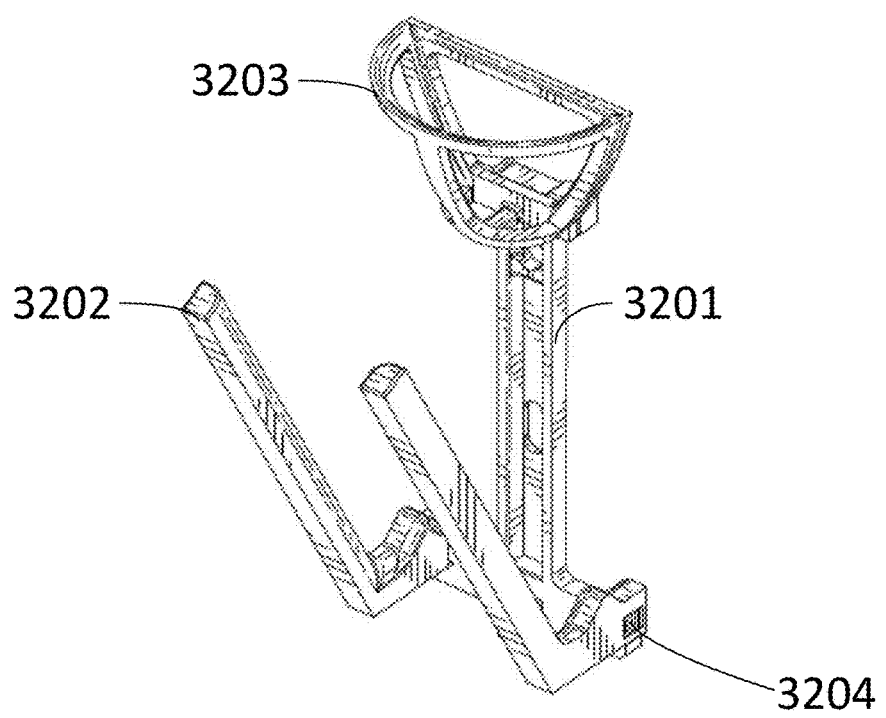
FIGS. 32A and 32B are front (FIG. 32A) and rear (FIG. 32B) perspective views of a bracket, according to a further example embodiment.
Figure 32B:
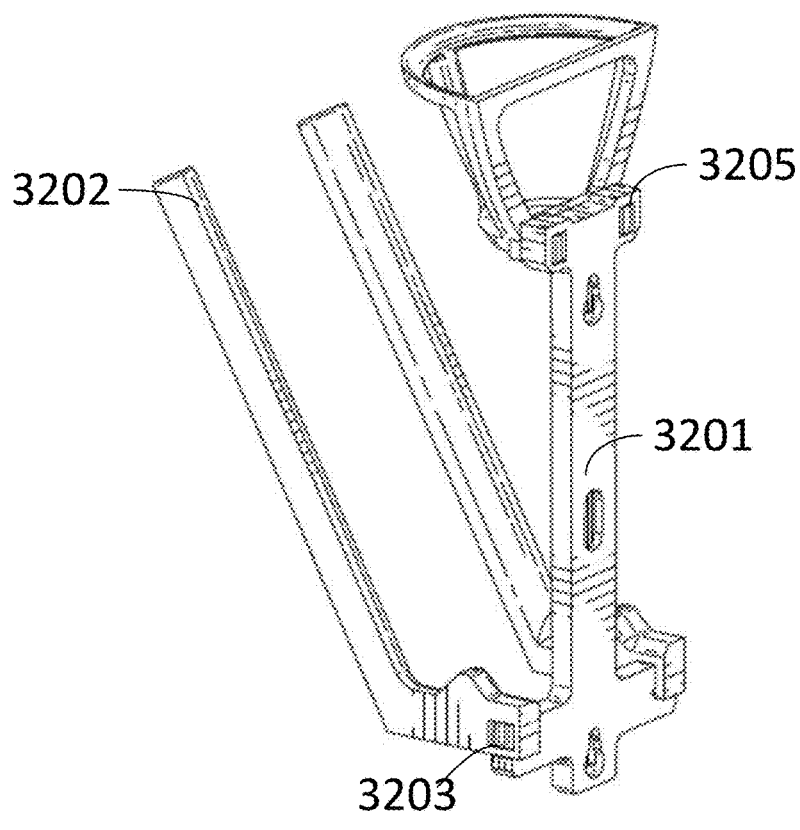

FIGS. 32A-32B show front and rear perspective views of another example bracket assembly member that may be used to support a keyboard (or other objects), according to an example embodiment. FIGS. 32A-32B show the bracket assembly including a bracket base 3201, a first support member 3202 coupled to the base 3201, a second support member 3203 coupled to the base 3201 and positioned vertically above the first support member 3202, a first bracket coupler 3204, and a second bracket coupler 3205. The first bracket coupler 3204 is an aperture defined by the first support member 3202 and configured to receive one or more projections extending from the base 3201 to couple the first support member 3202 to the base 3201. The second bracket coupler 3205 is an aperture defined by the base 3201 and configured to receive one or more projections extending from the second support member 3205 to couple the second support member 3205 to the base 3201.

Figure 33A:
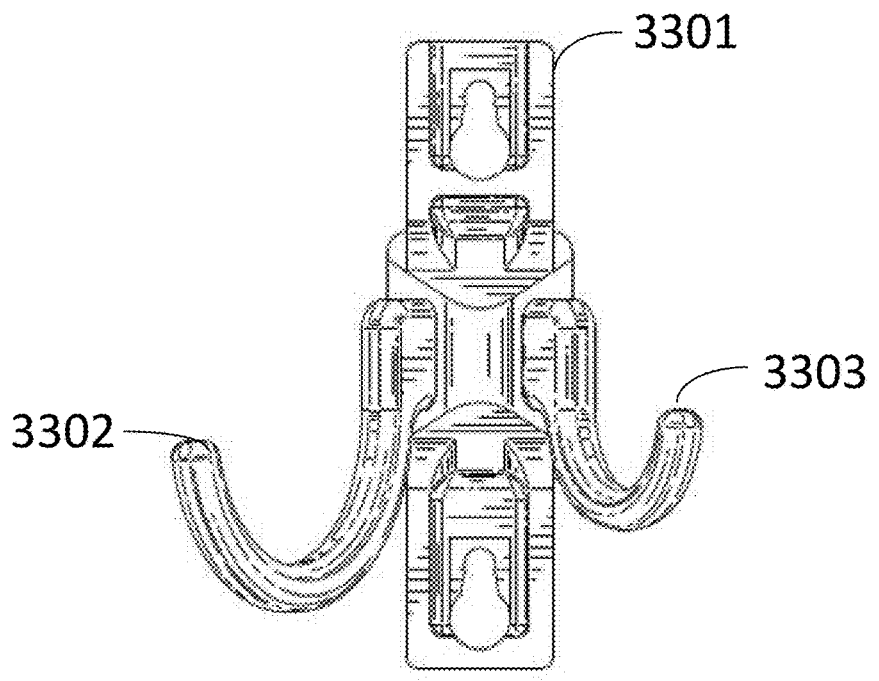
FIGS. 33A and 33B are a front (FIG. 33A) and rear (FIG. 33B) elevation view of a bracket, according to another example embodiment.
Figure 33B:
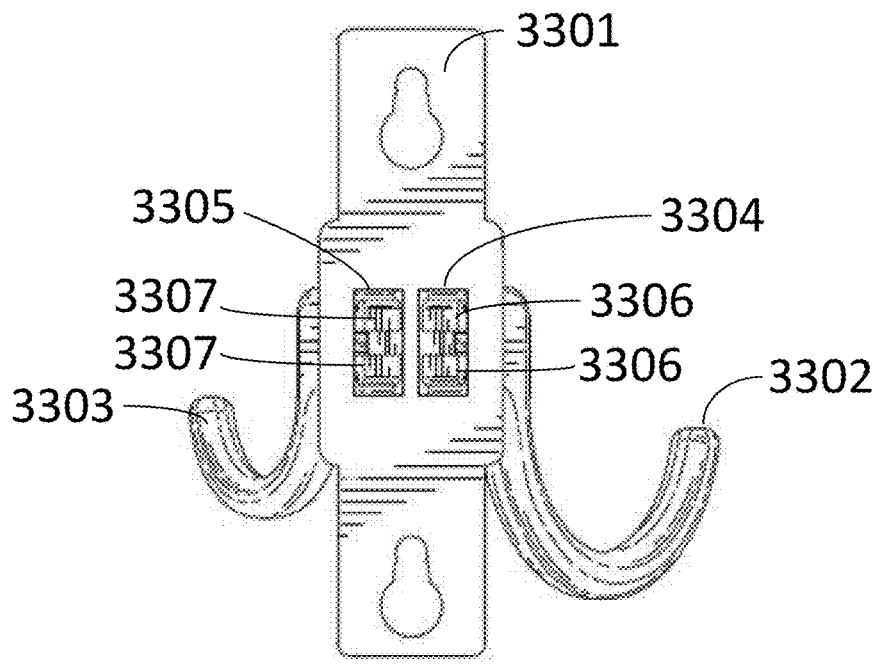

FIGS. 33A-33B show front and rear elevation views of an example bracket assembly that may be used to support hanging items (e.g., a purse, a coat, a ID badge, etc.), according to an example embodiment. FIGS. 33A-33B show the bracket assembly including a bracket base 3301, a first support member 3302 coupled to the base on a left side of the base, a second support member 3303 coupled to the base 3301 on a right side of the base (opposite the first support member), a first bracket coupler 3304 of the base 3301, and a second bracket coupler 3305 of the base 3301. The support members 3302, 3303 may further include projections 3306 and 3307 extending respectively from support members 3302 and 3303 that are received by the bracket couplers to couple the support members to the base 3301. In this example, the base 3301 is structured as the universal bracket base 2000 described herein.

Figure 34A:
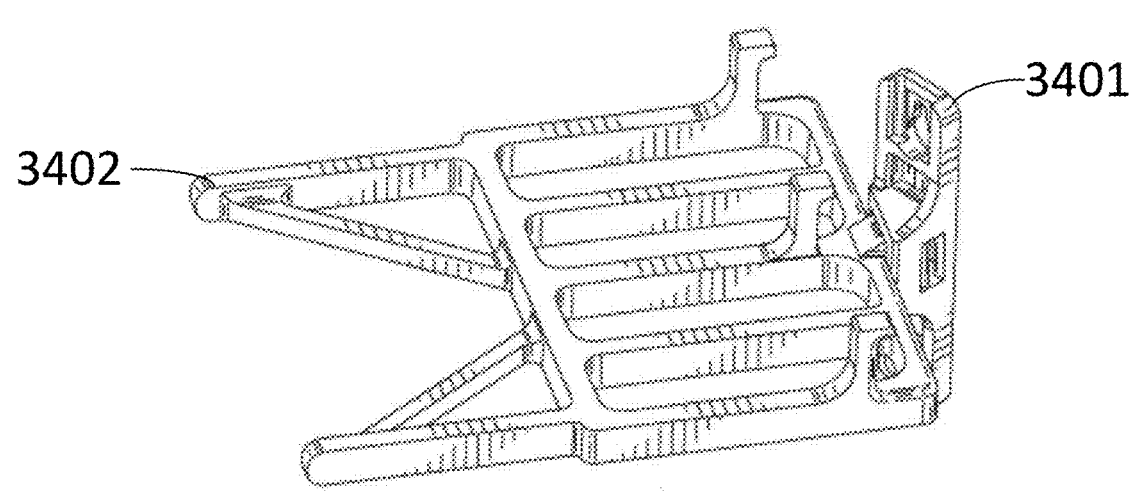
FIGS. 34A and 34B are front (FIG. 34A) and rear (FIG. 34B) perspective views of a bracket, according to still another example embodiment.
Figure 34B:
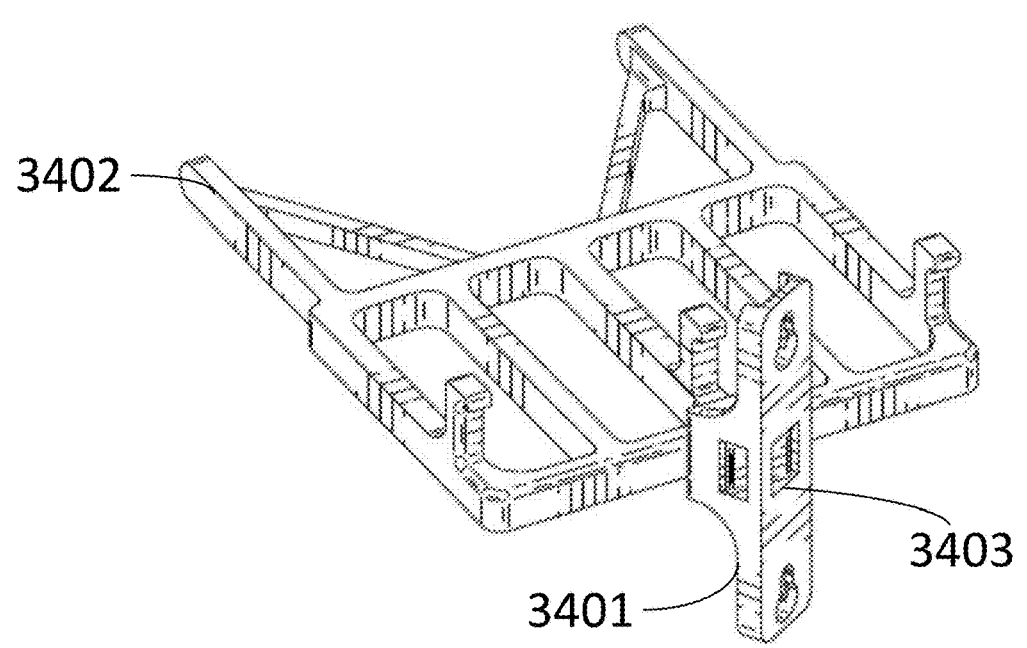

FIGS. 34A-34B show front and rear perspective views of an example bracket assembly that may be used to support goggles (i.e., laboratory or safety goggles) among a variety of other objects, according to an example embodiment. FIGS. 34A-34B show the bracket assembly including a bracket base 3401, a support member 3402 coupled to and extending away from the base 3401, and a bracket coupler 3403 configured as an aperture that receives a projection from the support member 3402 to couple the support member 3402 to the base 3401.

Figure 35A:
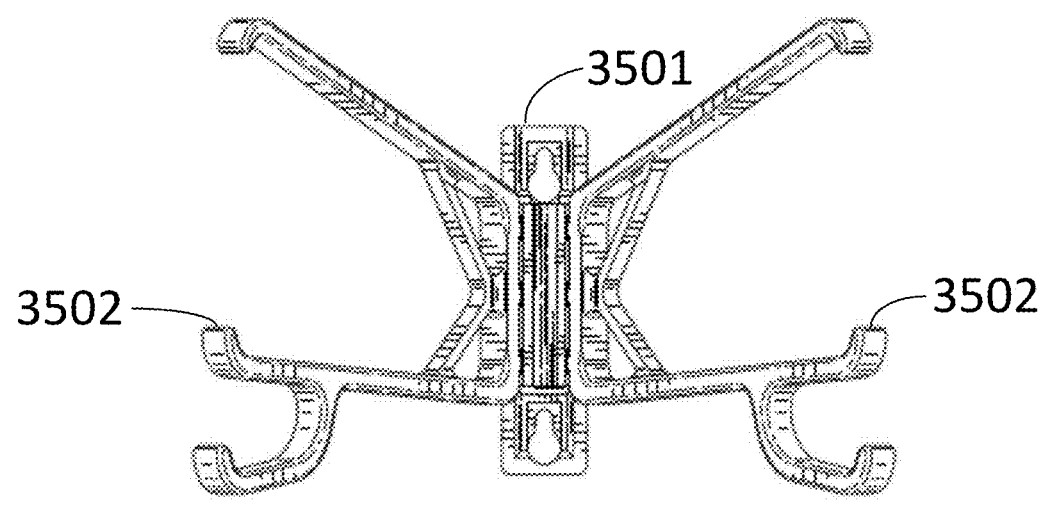
FIGS. 35A and 35B are front (FIG. 35A) and rear (FIG. 35B) elevation views of a bracket, according to another example embodiment.
Figure 35B:
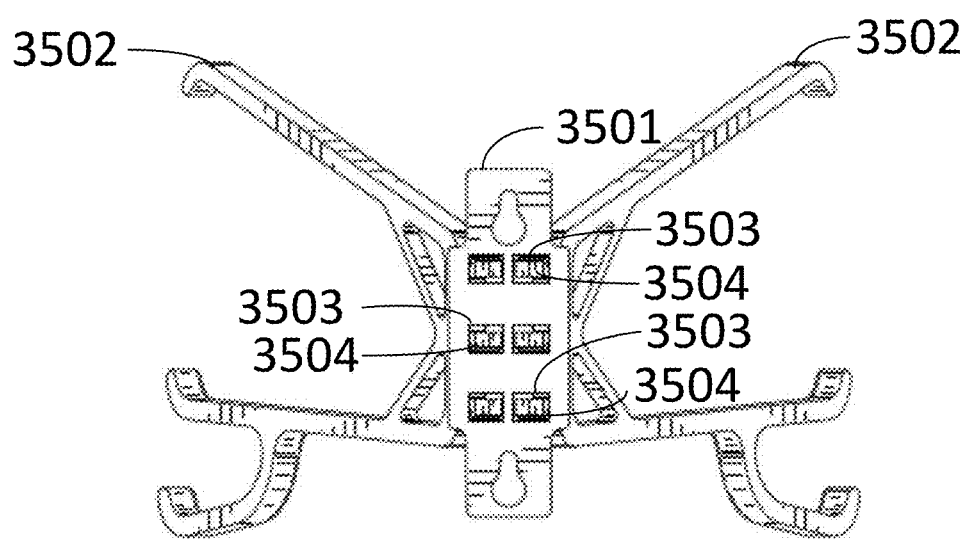

FIGS. 35A-35B show front and rear elevation views of an example bracket assembly that may be used to support one or more items or objects (e.g., gloves, scarves, etc.), according to an example embodiment. FIGS. 35A-35B show the bracket assembly including a bracket base 3501, a plurality of support members 3502 coupled to and extending away from the base 3501, and a plurality of bracket couplers 3503 of the base 3501. The support members 3502 can include one or more projections 3504 extending therefrom and configured to be received by the bracket couplers 3503 (i.e., one projection per coupler/aperture 3503).

Figure 36A:
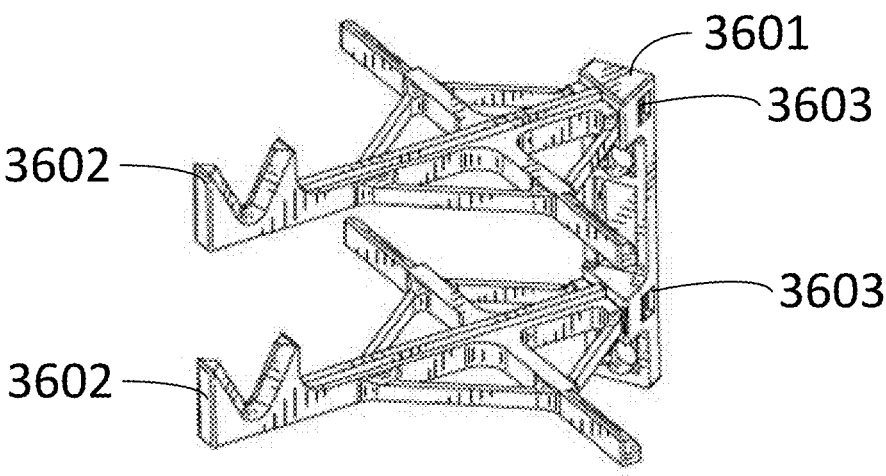
FIGS. 36A and 36B are front (FIG. 36A) and rear (FIG. 36B) perspective views of a bracket, according to still another example embodiment.
Figure 36B:
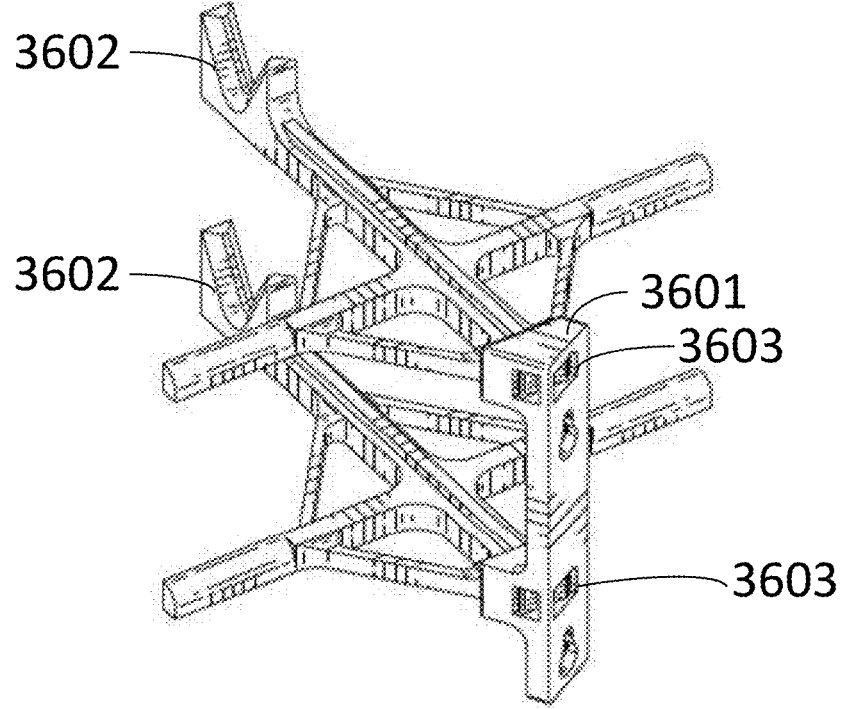

FIGS. 36A-36B show front and rear perspective views of an example bracket assembly that may be used to support eyeglasses, sunglasses, etc., according to an example embodiment. FIGS. 36A-36B show the bracket assembly including a bracket base 3601, a plurality of support members 3602 coupled to and extending away from the base 3601, and a plurality of bracket couplers 3603 of the base 3601 that are configured to receive a projection of the support member 3602 to couple the support member to the base 3601.

Figure 37A:
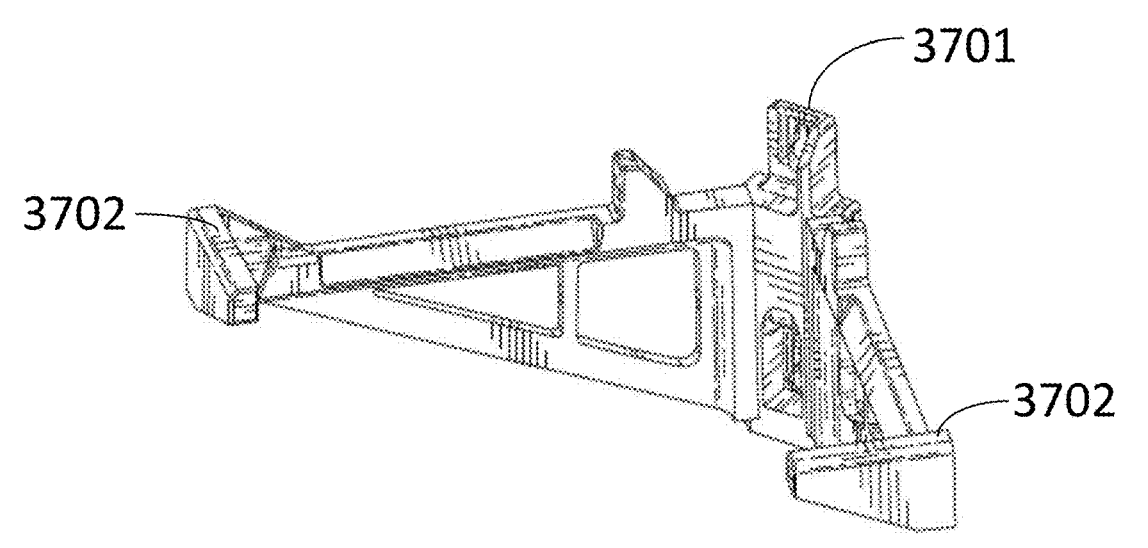
FIGS. 37A and 37B are front (FIG. 37A) and rear (FIG. 37B) perspective views of a bracket, according to yet another example embodiment.
Figure 37B:
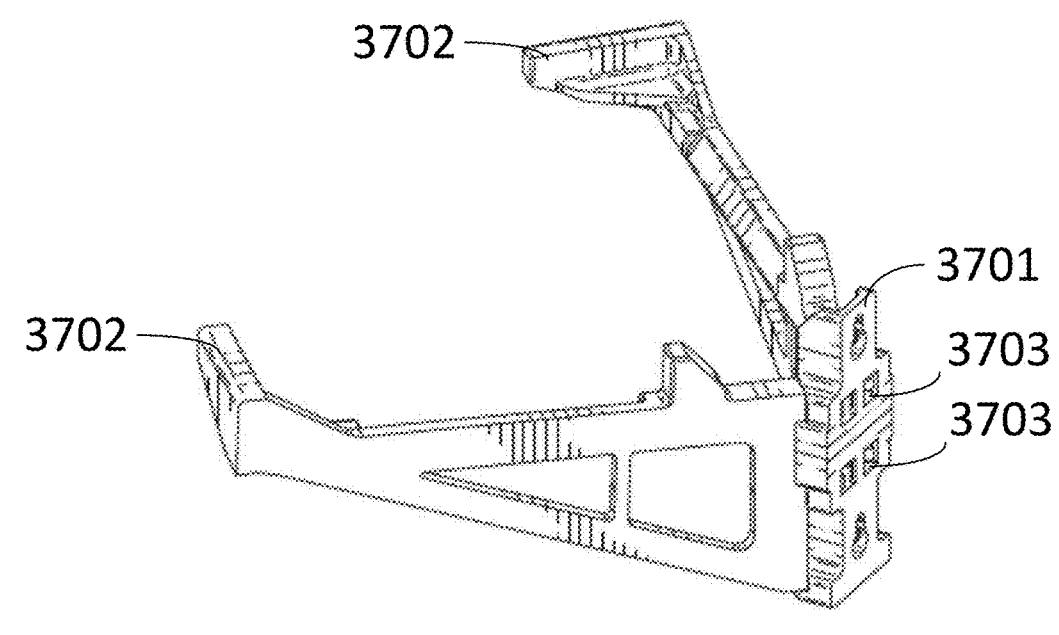

FIGS. 37A-37B show front and rear perspective views of an example bracket assembly that may be used to support sporting equipment (e.g., basketballs, volleyballs, etc.), according to an example embodiment. FIGS. 37A-37B show a bracket base 3701 (in this example, the base 3701 is structured as the universal base 2000), a plurality of support members 3702 coupled to and extending away from the base 3701, and a plurality of bracket couplers 3703 of the base 3701 that receive projections of the support members 3702 to couple the support members 3702 to the base 3701.

Figure 38:
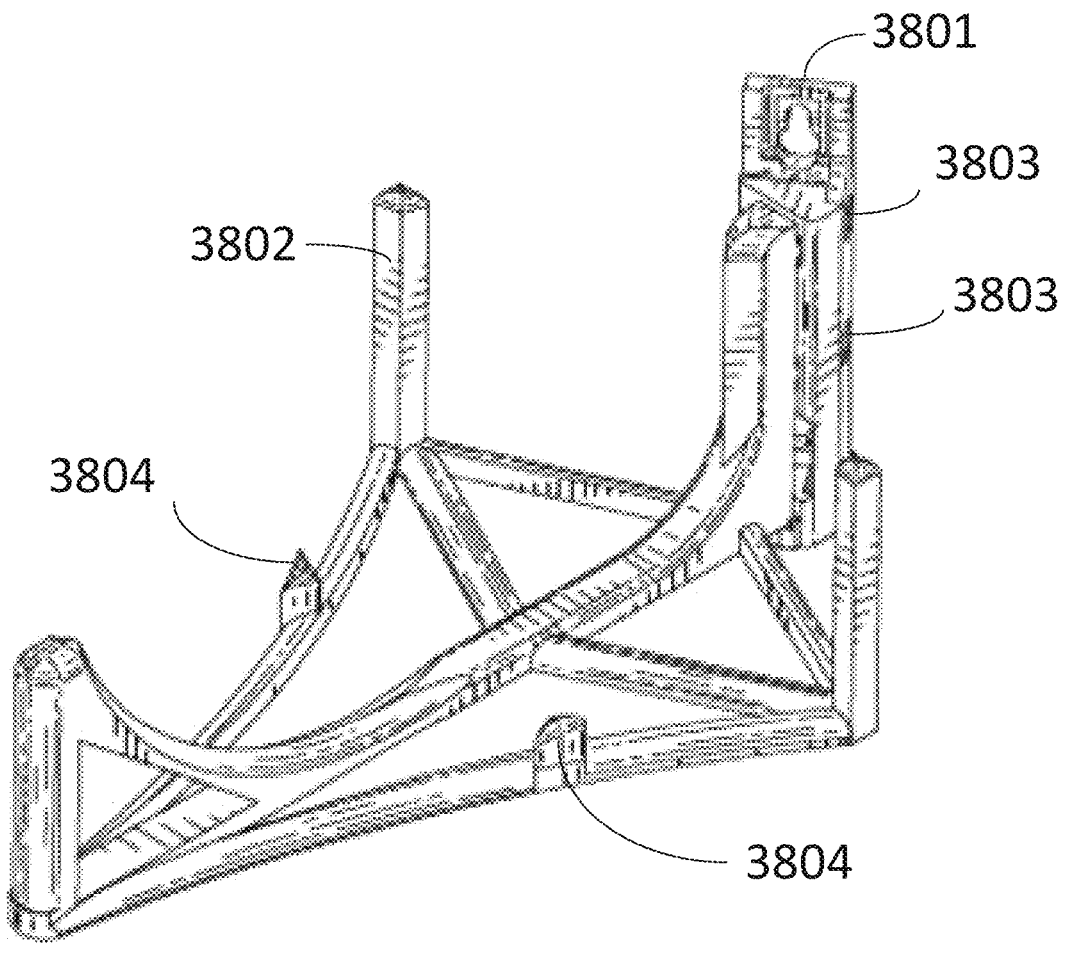
FIG. 38 is a front perspective view of a bracket, according to another example embodiment.

FIG. 38 shows a front perspective view of an example bracket assembly that may be used to support larger objects (e.g., circular objects such as foam ball, etc.), according to an example embodiment. FIG. 38 shows the bracket assembly including a bracket base 3801, a support member 3802 coupled to and extending away from the base 3801, and a plurality of bracket couplers 3803 (shown as apertures) that receive a projection of the support member 3802 to couple the support member 3802 to the base 3801. The support member 3802 is shown to include a plurality of low-contact touchpoints 3804 that reduce or minimize the contact area between the object and the bracket assembly (particularly, the support member 3802).

Figure 39A:
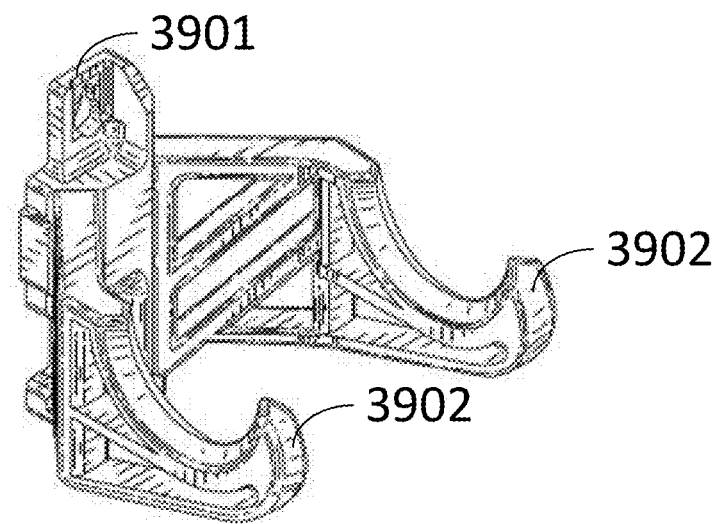
FIGS. 39A and 39B are front (FIG. 39A) and rear (FIG. 39B) perspective views of a bracket, according to still another example embodiment.
Figure 39B:
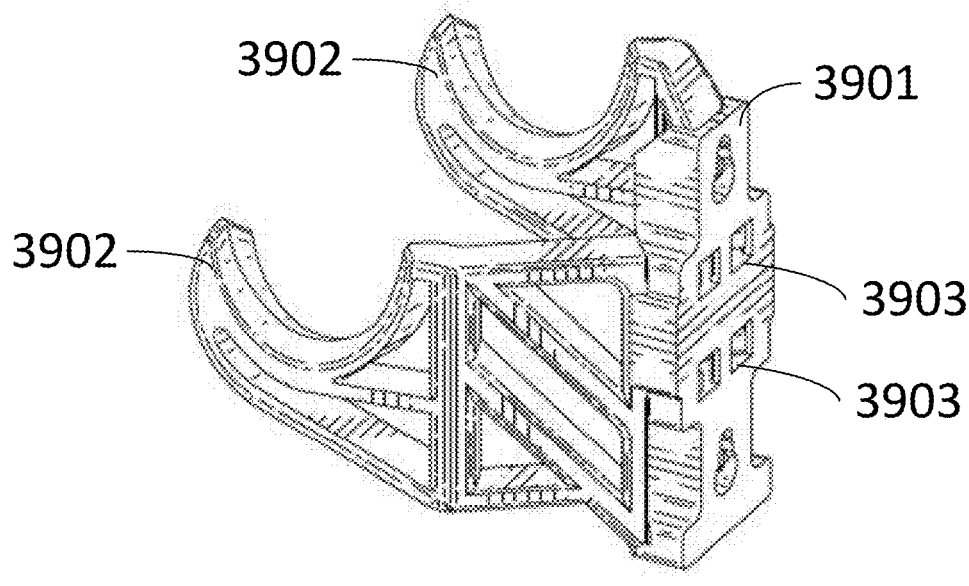

FIGS. 39A-39B show front and rear perspective views of an example bracket assembly that may be used to support various objects (e.g., an umbrella, a dumbbell, etc.), according to an example embodiment. FIGS. 39A-39B show the bracket assembly including a bracket base 3901 (which in this example is structured as the universal base 2000 described herein), a plurality of support members 3902 coupled to the base 3901, and a plurality of bracket couplers 3903 of the base 3901 that couple to the support members 3902 (as described herein with respect to the coupling structure of the universal base to various support members).

Figure 40:
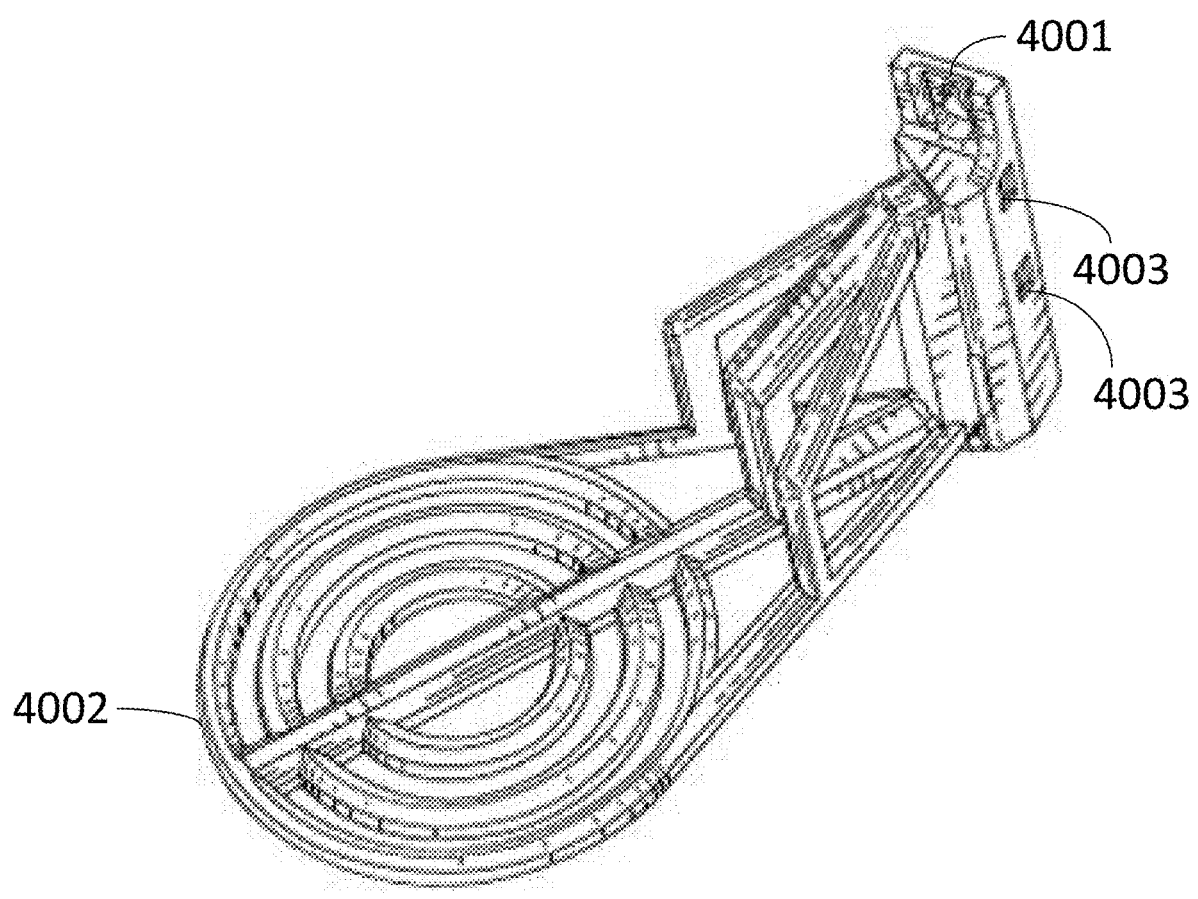
FIG. 40 is a front perspective view of a bracket, according to yet another example embodiment.

FIG. 40 shows a front perspective view of an example bracket assembly that may be used to support a various objects/items (e.g., foam roller, a pot, a pan, etc.), according to an example embodiment. In particular, the bracket assembly of FIG. 40 may be used to support a base of a foam roller used in physical therapy and fitness settings. FIG. 40 shows the bracket assembly including a bracket base 4001, a support member 4002 coupled to and extending away from the base 4001, and a plurality of bracket couplers 4003 of the base 4001 that receive a projection of the support member 4002 to couple to the base 4001.

Figure 41:
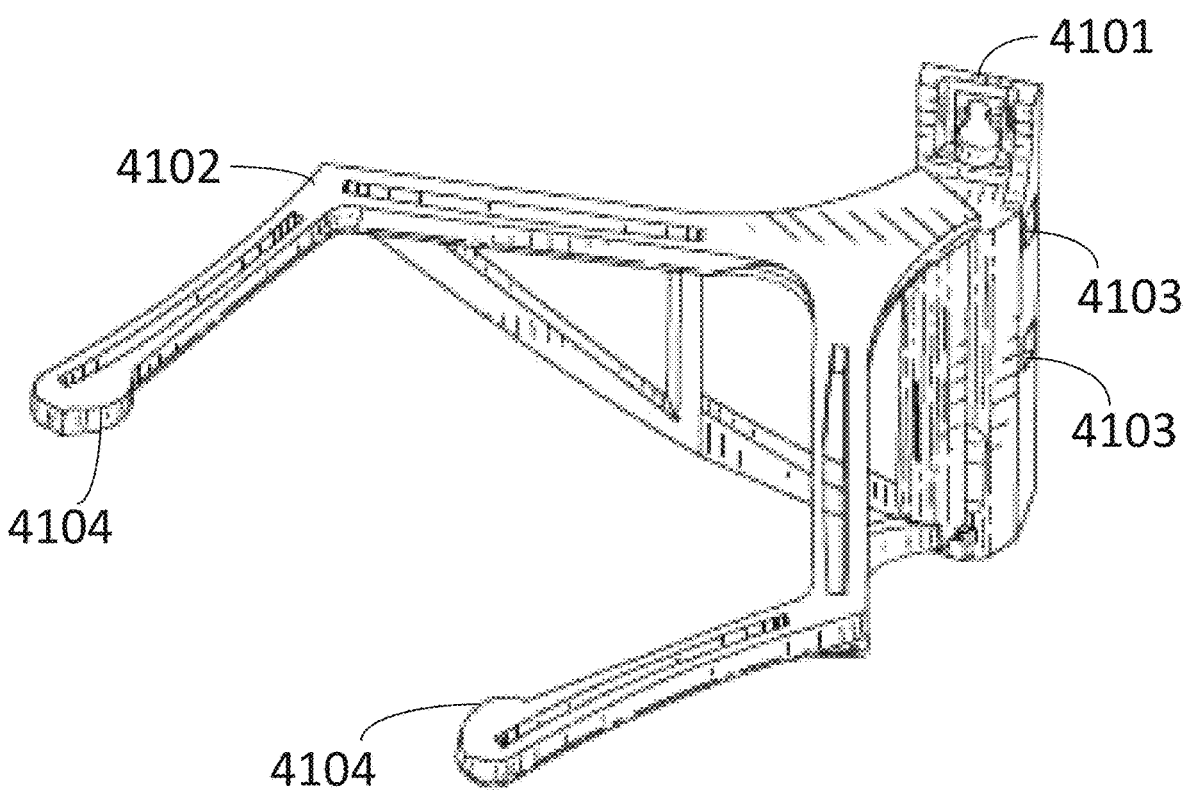
FIG. 41 is a front perspective view of a bracket, according to still yet another example embodiment.

FIG. 41 shows a front perspective view of an example bracket assembly that may be used to support various objects, such as a foam roller, according to an example embodiment. In one embodiment, the bracket assembly of FIG. 41 can be used in combination with the bracket assembly of FIG. 40 to support a foam roller used in physical therapy and fitness settings. More specifically, the bracket assembly of FIG. 41 can be configured to support a cylindrical body of a foam roller. FIG. 41 shows the bracket assembly including a bracket base 4101, a support member 4102 coupled to and extending away from the base 4101, and a plurality of bracket couplers 4103 of the base that receive a projection of the support member 4102 to couple the support member to the base 4101. The support member 4102 may include a plurality of low-contact features or objects 4104, according to an exemplary embodiment. In particular, the low-contact features 4104 can contact a cylindrical body of a foam roller at two points, thereby minimizing contact between the support member 4102 and the foam roller.

Figure 42A:
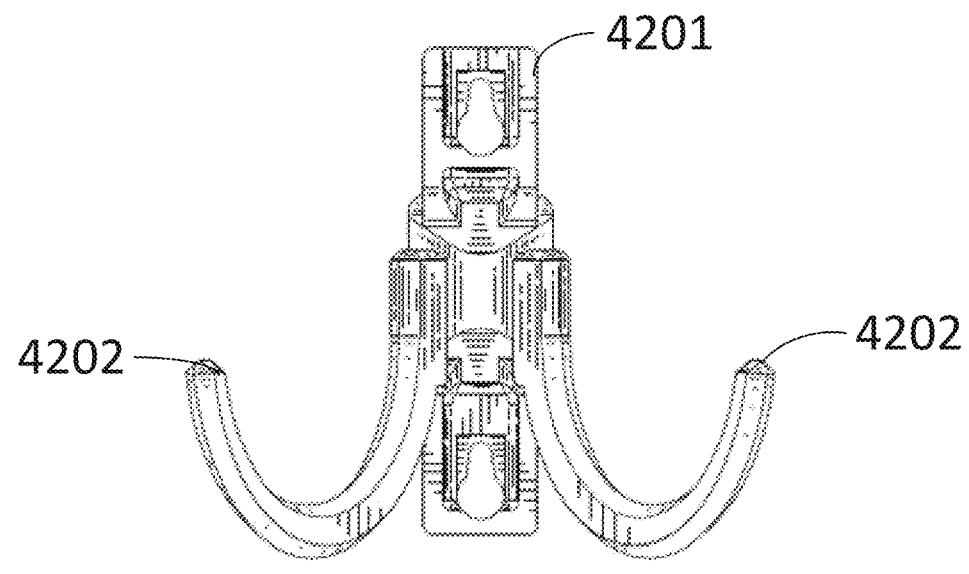
FIGS. 42A and 42B are front (FIG. 42A) and rear (FIG. 42B) elevation views of a bracket, according to yet another example embodiment.
Figure 42B:
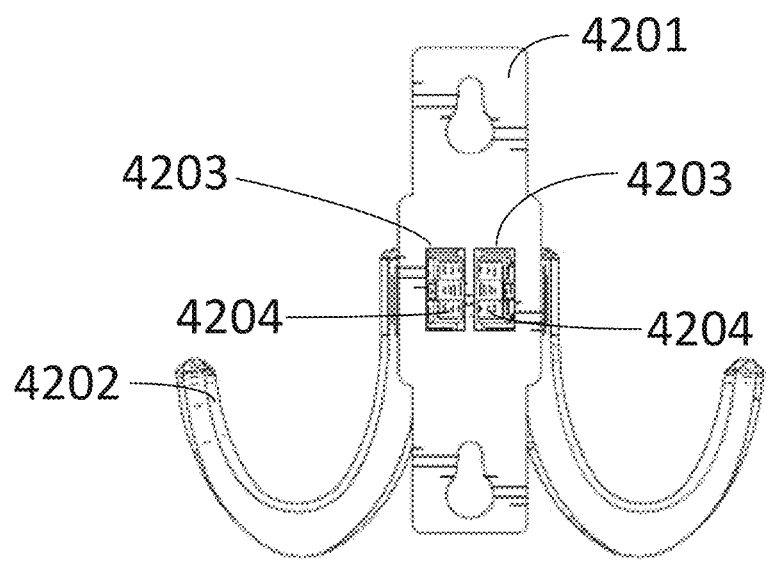

FIGS. 42A-42B show front and rear perspective views of an example bracket assembly that may be used to support various objects/items (e.g., hats, massage devices, etc.), according to an example embodiment. FIGS. 42A-42B show the bracket assembly including a bracket base 4201, a plurality of support members 4202 coupled to and extending away from the base 4201, and a plurality of bracket couplers 4203 of the base that couple the support members 4202 to the base 4201. The support members 4204 can include at least one projection 4204 extending therefrom and configured to be received by the bracket couplers 4203 in order to couple the support member to the base, as described herein.

As shown in each of the bracket couplers (e.g., 2503, 4203), the bracket couplers may be configured to receive at least one projection (e.g., 2804, 3306, 3307, 3505, 4204) of the support member (e.g., 2802, 3602, 3603, 3502, 4202). The at least one projection (e.g., extension, protruding member, extending member, extension etc.) may be coupled to and extend from an end of the support member (e.g., 2802, 3602, 3603, 3502, 4202) and/or be integral with the bracket attachment (i.e., a unitary or solitary component). The at least one projection may extend outward and away from an end of the support member. The at least one projection may include one or more raised portions that project outward and away from at least a portion of the projection. The projection is configured to couple to the bracket base 2000 (or bracket bases 2801, 3601, 3501, 4201, etc.) to couple the support member to the universal bracket base 2000, which is described herein below.

The support member (e.g., 2802, 3602, 3603, 3502, 4202) extends into an interior of the cabinet (e.g., cabinet 1800, 1900). The support member (e.g., 2502, 4202) is configured to support, suspend, or otherwise hold one or more objects within the cabinet. As shown in FIGS. 25A-42B, a variety of support member are depicted that have a variety of different shapes and sizes. The shapes and sizes are used to accommodate a variety of objects (e.g., dumbbells, wires, goggles/ eye ware, keyboards, mobile phones, laptop computers, gloves, stethoscopes, etc.). Those of ordinary skill in the art will appreciate the high configurability of the shapes and sizes that may be used to accommodate various objects, even the same type of object (i.e., multiple shapes and sizes may be used to accommodate wire objects).

Many support members (e.g., 2502, 4102) are shown to include low-contact features (e.g., 2504, 3804, 4104). For example, FIGS. 25, 38, and 41 show a support member 2502, 3802, 4102 including a plurality of points 2504, 3804, 4104 extending away from the support member 2502, 3802, 4102. The support members can also include a plurality of ridges. The low-contact features/objects are configured to reduce a surface area contact zone for the object and the respective bracket attachment/support member (and, bracket in general). That way and beneficially, the sterilization and/or disinfection cycle is more likely to impact most of the object/item. It should be understood that a variety of low-contact features may be utilized, such that the points and ridges depicted are not meant to be limiting with other structures having other shapes and sized envisioned.

Multiple base configurations/structures are shown in FIGS. 25A-42B with some embodiments showing the universal base 2000. While different base shapes and sizes are shown, the coupling mechanism of the support member to the base is substantially consistent throughout, which is described in more detail below with respect to the universal base 2000.

Based on the foregoing, coupling of the bracket/support member to the universal base 2000 may be described as follows. The apertures 2050 of the universal bracket base 2000 may be configured to receive projections (e.g., 2804, 3306, 3307, 3504, 4204) of a support member/bracket attachment (e.g., 2802, 3602, 3603, 3502, 4202). Each of the aforementioned projections of a bracket attachments may be inserted into a bracket coupler (e.g., 2050, 2803, 3604, 3605, 3503, 4203 that is shown as an aperture/opening) where, in doing so, causes the projection (and any raised portions associated therewith) to flex or move because the size of the aperture 2050 or bracket coupler (cross-sectional size) may be relatively smaller than the cross-sectional size of the projection (and any raised portions associated therewith). Once a substantial portion of the projection is pushed through the aperture 2050 or bracket coupler, the projection (and any raised portions associated therewith may spring, expand, flex, or otherwise move back to a non-flexed position. This causes the raised portions associated with the projection to engage with the universal bracket 2000 (e.g., contact, etc.) in a way that prevents the projection and bracket attachment from being removed from the universal bracket 2000 (i.e., clip into place). To remove the bracket and insert a new bracket to the bracket 2000, a user may move the projection inward to enable that portion to be slid or moved out of the apertures 2050 to disconnect the bracket from the base 2000.

Figures 21, 22:
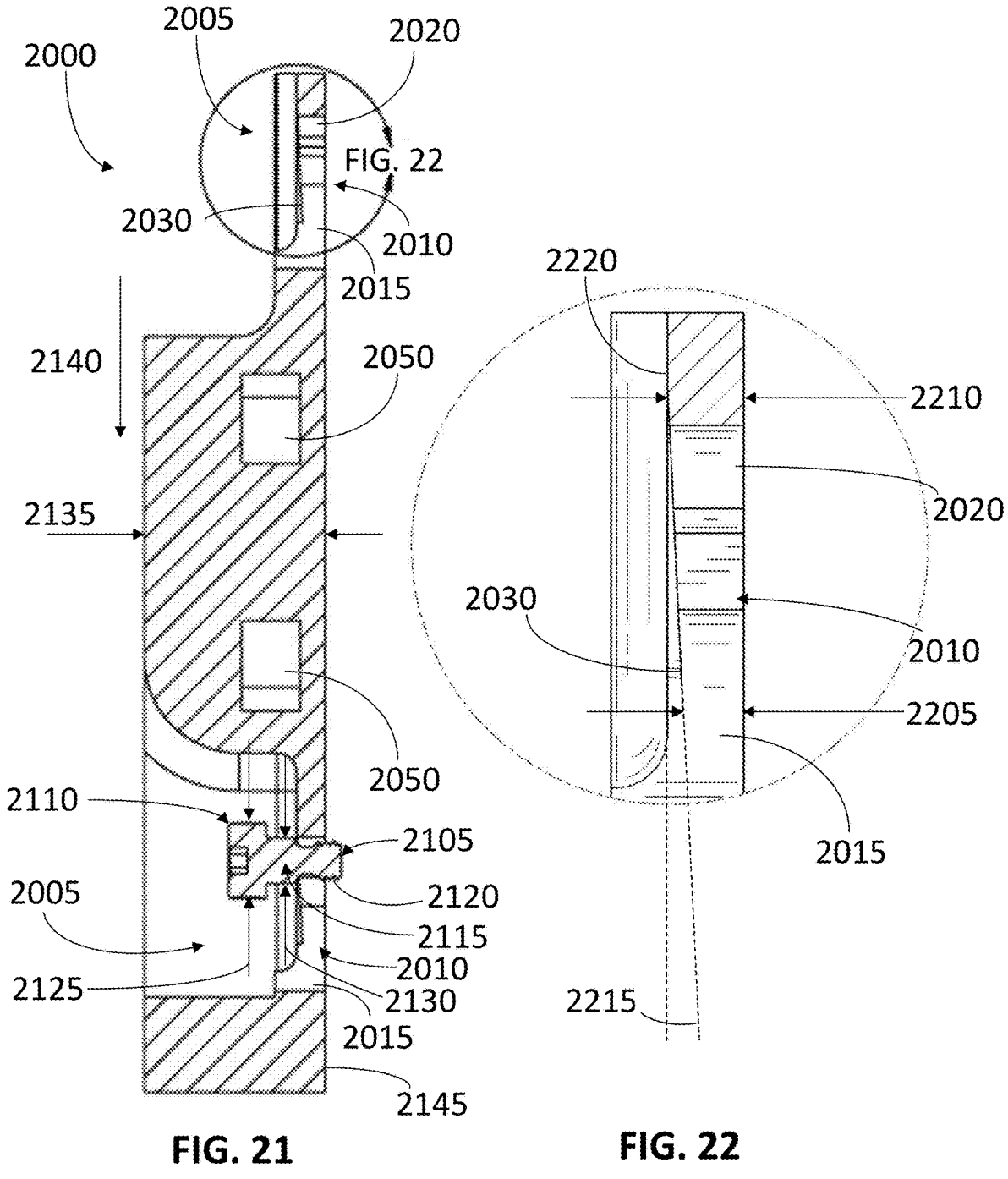
FIG. 21 is a cross-sectional view of the universal bracket base of FIG. 20, according to an example embodiment.
FIG. 22 is a detail view of the coupling structure of the universal bracket base of FIG. 21, according to an example embodiment.

Whether apertures, protrusions, or other coupling means are employed, in one embodiment, the bracket couplers of the base can be angled or offset with respect to a back surface of the universal bracket base 2000 (shown as back surface 2145 of FIG. 21). As a result, the support member can be angled (i.e., offset) with respect to the back surface 2145 of the universal bracket base 2000. As discussed above with reference to FIG. 9, the support members may desirably be offset with respect to the back surface 2145 and the interior framework of the cabinet in order to optimize exposure to vaporized/atomized chemicals, UV light, heated air, etc. during a disinfection and/or sterilization cycle within the cabinet. In some embodiments, both the bracket attachment coupling means and the bracket attachment itself will be oriented such that the object supported by the bracket within the cabinet is "offset" as herein described. In another embodiment, the base 2000 may not include the offset/angle yet the support member itself includes a body portion coupled to the projection to offset the support member (put at an angle) relative to the base 2000. The angling/offset may enable relatively more objects to be included in the cabinet.

In various embodiments, the universal bracket base 2000 and/or the support member can comprise a semi-malleable or ductile material. For example, each of the universal bracket base 2000 and the bracket attachment/support member can be or comprise plastic material. In another embodiment, a portion of the universal bracket base 2000 and/or the bracket attachment/support member can comprise a plastic material, while a remainder of the universal bracket base 2000 and the bracket attachment comprise another material (e.g., a metal material). For example, the coupling structure 2005 of the universal bracket base 2000 and the protruding member of the bracket attachment can comprise a plastic material while the remainder of the universal bracket base 2000 and the bracket attachment comprise some other material.

Referring now to FIG. 21, a cross-sectional view of the base 2000 is depicted, according to an example embodiment. A shown, the base 2000 includes a fastener 2105. The fastener 2105 (e.g., screw, bolt, etc.) can be inserted within the opening 2010 of one or more couplers 2005 of the universal bracket base 2000 described above with respect to FIG. 20. A plurality of fasteners 2105 are coupled to the carrousel structure to facilitate coupling to a plurality of bases 2000. The fastener 2105 can have a head 2110, a shaft 2115, and a threaded portion 2120. The head 2110 has a head diameter 2125. The shaft 2115 can a shaft diameter 2130. According to one embodiment, the head diameter 2125 is less than the first diameter 2035 of the universal bracket base 2000, but larger than the second diameter 2040 of the universal bracket base 2000. The shaft diameter 2130 can be less than both the first diameter 2035 and the second diameter 2040 of the universal bracket base 2000, according to various embodiments. In some embodiments, the shaft diameter 2130 can be greater than the protrusion distance 2045. The threaded portion 2120 can be configured to thread into an aperture of the interior framework of a cabinet, according to one embodiment. In other embodiments, the fastener may be coupled to the interior framework of the cabinet by some other means (e.g., welding, press-fitting, adhesive,) or may be integrally formed with the interior framework of the cabinet.

The universal bracket base 2000 can be installed to the internal cabinet framework by securing the universal bracket base 2000 over one or more fasteners 2105 (e.g., pegs, etc.). With one or more fasteners 2105 coupled with the interior framework (e.g., a rotating carrousel having a plurality of wings extending radially from an axis of rotation, the wings coupled to one or more vertically-oriented shafts, columns, or posts, where the shafts, columns, or posts are configured to couple with a universal bracket base) of the cabinet, the head 2110 of each fastener 2105 may be inserted through the first opening 2015 such that the head 2110 extends beyond surface 2030. In one embodiment, the universal bracket base 2000 can be translated in direction 2140 relative to the fasteners 2105 while the fasteners 2105 remain coupled with the interior framework of the cabinet. As the universal bracket base 2000 is translated, the shaft 2115 of each fastener 2105 passes or extends through the two protrusions 2025 of each coupler 2005. As noted above, the protrusion distance 2045 is less than the shaft diameter 2130. According to an exemplary embodiment, the protrusions 2025 can be configured to deform slightly in order to allow the shaft 2115 of a fastener 2105 to pass between the protrusions 2025. As noted above, each protrusion 2025 may comprise a malleable or ductile material that can deform slightly to allow the shaft 2115 to pass between the protrusions 2025 before substantially returning to its original shape. After the shaft 2115 of each fastener 2105 passes though the protrusions 2025, the shaft 2115 of each fastener 2105 can extend through the second opening 2020 of each respective coupling means 2005. Furthermore, with the shaft 2115 extending through the second opening 2020, the protrusions 2025 of the coupler 2005 are beneath the shaft 2115 and can retain the shaft 2115 within the second opening 2020, according to an exemplary embodiment. In this way, the universal bracket base 2000 is substantially kept from moving relative to the shaft 2115 because the shaft 2115 (and the fastener 2015 more generally) are bounded by the protrusions 2025 and the second opening 2020. When the shaft 2115 is bounded by the protrusions 2025 and the second opening 2020, the universal bracket base 2000 is in an installed position.

As indicated above, the surface 2030 can be a pitched or angled surface, as shown in detail in FIG. 22. According to an exemplary embodiment, the surface 2030 can be pitched or angled such that a wall thickness 2205 of the coupler 2005 at the first opening 2015 is smaller than a wall thickness 2210 of the coupler 2005 at the second opening 2020. The surface 2030 can be pitched at an angle 2215 relative to a flat surface 2220, according to an exemplary embodiment. Moreover, the wall thickness 2215 of the coupler 2005 proximate to the second opening 2020 can be substantially similar to a distance from the head 2110 of a fastener to the interior framework of the cabinet. In this way, as the universal bracket base 2000 is translated in direction 2140 relative to the fasteners 2105 towards the aforementioned installed position, the coupler 2005 tightens against the head 2110 of the fastener 2105. Specifically, when the universal bracket base 2000 is in the installed position (i.e., when the fastener shaft 2115 is within the second opening and has passed between the protrusions 2025), the surface 2030 contacts (e.g., engages) a back surface of the head 2110, further securing the universal bracket base 2000 to the fastener 2105 and interior framework of the cabinet.

Figure 23:
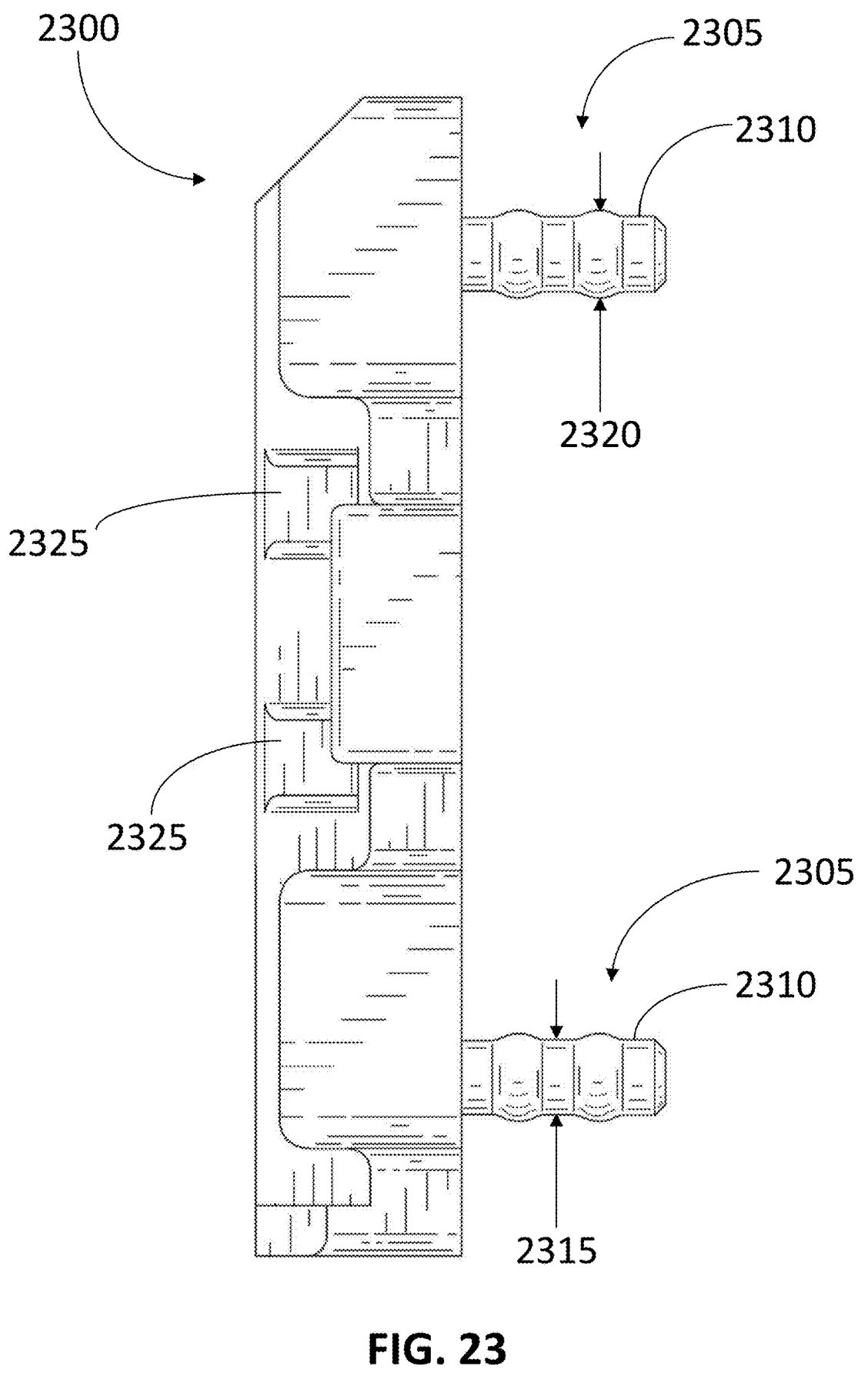

Referring now to FIG. 23, a universal bracket base 2300 is shown, according to another example embodiment. The universal bracket base 2300 can be configured to couple with an interior framework (e.g., rotating carrousel) of a disinfection and sterilization cabinet, as herein described. The universal bracket base 2300 can include one or more coupling structures, couplers, coupling elements, etc. 2305. In contrast to the opening 2010 of the universal bracket base 2000 shown in FIG. 20-22 and discussed above, the coupling structures 2305 of the universal bracket base 2300 are configured as protruding members 2310. In this example, two protruding members 2310 are included with the base 2300. In other example embodiments, fewer or more than two protruding members 2310 are included with the base 2000. The protruding member 2310 can be configured to be received by one or more apertures of the interior framework of the cabinet, such as an aperture defined by a post or beam of the internal cabinet framework (e.g., the wing frame 1105 as shown in FIG. 11). Each protruding member 2310 can include a minor diameter 2315 that is smaller than a diameter of the aperture of the interior framework. Furthermore, each protruding member 2310 can include a major diameter 2320 that is greater than the diameter of the interior framework. According to an exemplary embodiment, portions of the protruding member 2310 including the major diameter 2320 may slightly deform as the protruding member 2310 is inserted into the aperture of the interior framework. Once inserted into the aperture of the interior framework, the portion of the protruding member 2310 including the major diameter 2320 may substantially return to its original shape (i.e., expand), thereby preventing the protruding member 2310 from being removed from the aperture of the interior framework. According to an exemplary embodiment, a resistance force must be overcome before the portions of the protruding member 2310 having the major diameter 2320 can be deformed to insert the protruding member 2310 into or remove the protruding member 2310 from the aperture of the interior framework.

The universal bracket base 2300 can also include bracket attachment coupling means, shown as apertures 2325. According to an exemplary embodiment the apertures 2325 can be similar to the apertures 2050 shown in FIGS. 20 and 21 and described above. In various embodiments, the protruding members 2310 can be integrally formed with the universal bracket base 2300 such that the universal bracket base 2300 and the protruding members 2310 comprise a single part, according to one embodiment. In another embodiment, the protruding members 2310 can be fastened to or coupled with the universal bracket base 2300.

Figure 24:
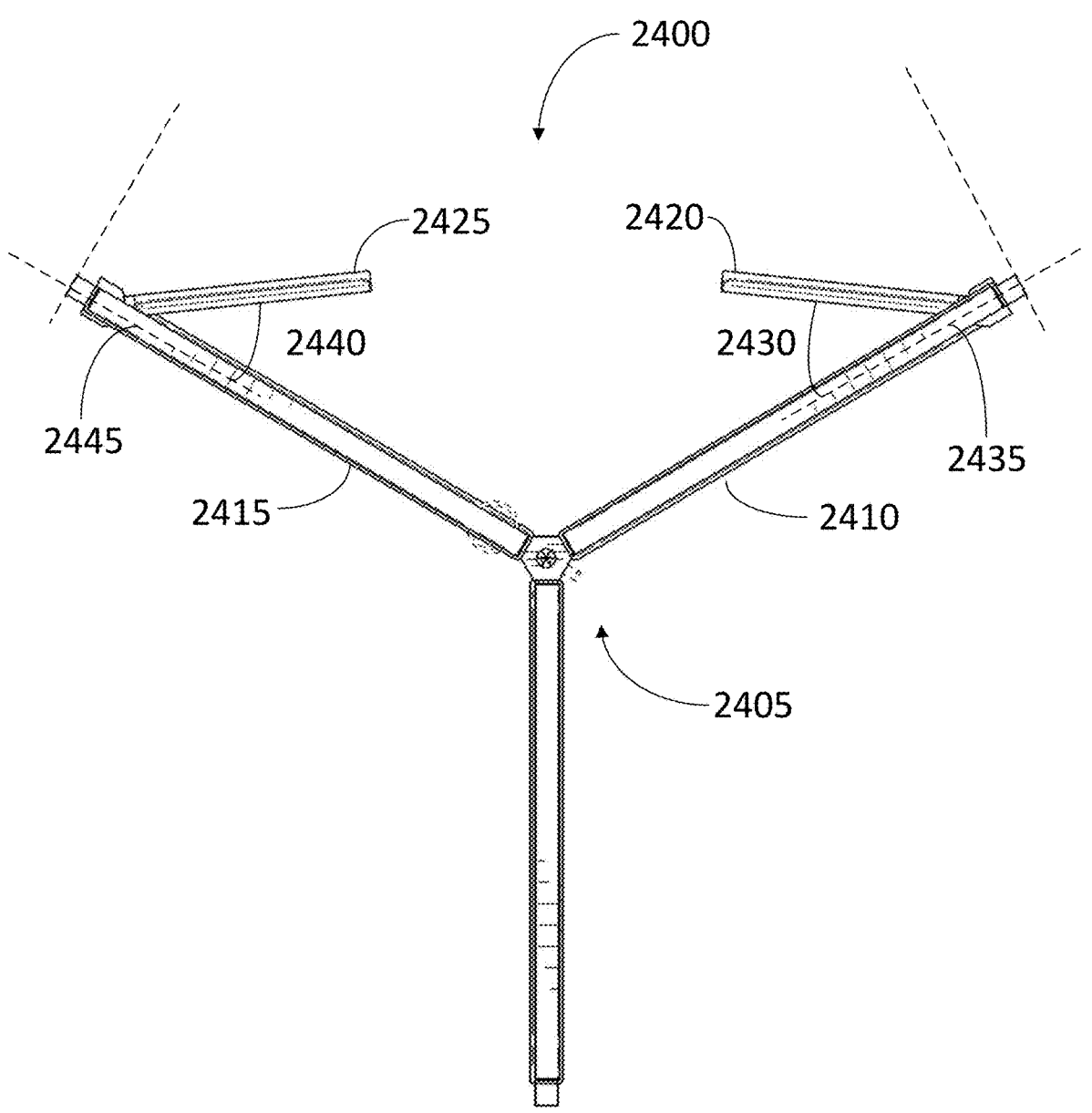
FIG. 24 is a top view of an interior framework of a cabinet, according to an example embodiment.

Referring now to FIG. 24, an interior framework 2400 of a disinfection or sterilization cabinet is shown, according to an exemplary embodiment. The interior framework 2400 can include a carrousel 2405 that can be configured to rotate about a central axis, according to an exemplary embodiment. As described above with reference to FIG. 11 and others, the carrousel may be driven via a drive-clutch that allows the carrousel to rotate in one direction with and allows for appropriate safety slippage in the event the carrousel 2405 crashes into an object within the cabinet. The drive-clutch may be communicably coupled to the display device (e.g., display device 1840 or 1940) such that a user may control the rotation of the carrousel 2405 via the display device. The rotating carrousel 2405 can include a plurality of wings, such as wings 2410 and 2415. In an exemplary embodiment, the rotating carrousel 2405 can include three wings. As described above, a bracket may be coupled the interior framework, namely to posts or beams positioned proximate to a distal end of each wing (e.g., to wing frames 1105 as shown in FIG. 11). More specifically, the one or more brackets may be coupled to the interior framework of the cabinet such that the bracket is "offset" from the frame, as discussed in detail above with reference to FIGS. 9 and 20. In some embodiments, the object to be disinfected or sterilized is too large, heavy, or bulky to be supported by a single bracket or by multiple brackets coupled along a single wing of the carrousel. Accordingly, circumstances may arise where it may be desirable to support an object (e.g., a lead vest) using a plurality of brackets coupled with the interior framework of the cabinet via multiple wings.

More specifically, and as shown in FIG. 24, a first bracket or bracket assembly 2420 can be coupled to the first wing 2410 of the carrousel 2405, while a second bracket or bracket assembly 2425 can be coupled to the second wing 2415 of the carrousel 2405. Rather than each bracket or bracket assembly 2420, 2425 being offset in the same direction (i.e., clockwise or counterclockwise) relative to wings 2410, 2415, respectively, bracket assemblies 2420 and 2425 are offset in opposite directions. In particular, the first bracket or bracket assembly 2420 is offset relative to wing 2410 in a first direction, while the second bracket or bracket assembly 2425 is offset from wing 2415 in a second direction. According to one embodiment, the two bracket assemblies 2420, 2425 can be offset in a direction facing the other bracket assembly 2425, 2520. The first bracket 2420 can be offset at a first angle 2430 from a wing centerline 2445. The second bracket 2425 can be offset from at a second angle 2440 from a second wing centerline 2445. According to an exemplary embodiment, the first angle 2430 and the second angle 2440 may be substantially similar (albeit in different directions).

Although substantially similar offset angles of multiple brackets can be used prevent one supported object from obscuring or occluding another supported object from exposure to vaporized/atomized chemicals, UV light, heated air, etc. during a sterilization or disinfection cycle as noted above with reference to FIG. 9, the example of FIG. 24 represents an instance where differing offset angles of various brackets may be necessary. When large, heavy, or bulky objects are supported within the cabinets as shown in FIG. 24, it may also be necessary to remove the center shaft (e.g., center shaft 1103 shown in FIG. 11) of the carrousel 2405 to bolster exposure to vaporized/atomized chemicals, UV light, heated air, etc.

Figure 43:
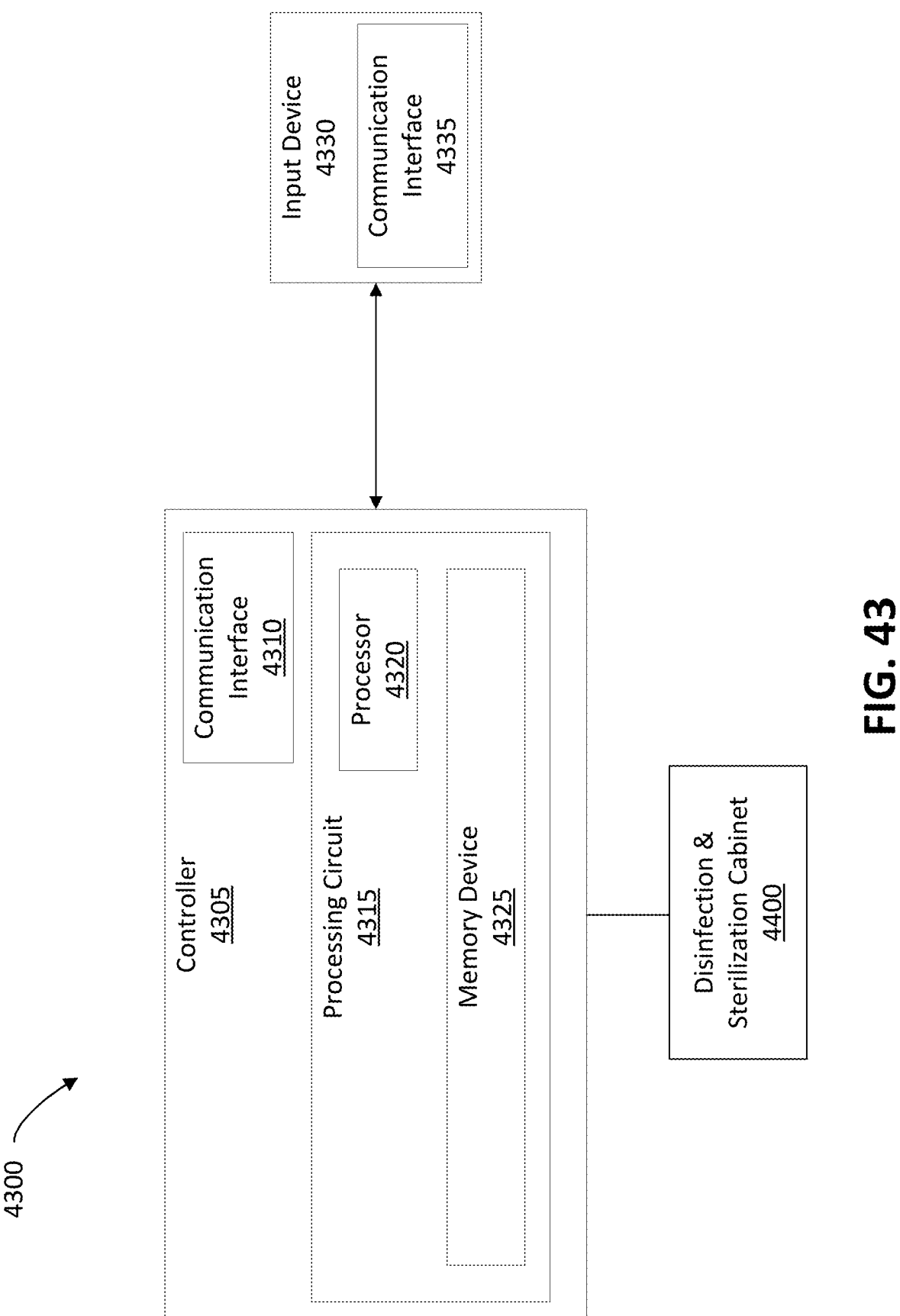
FIG. 43 is a block diagram of a control system for controlling a cabinet, according to an embodiment.
Figure 44:
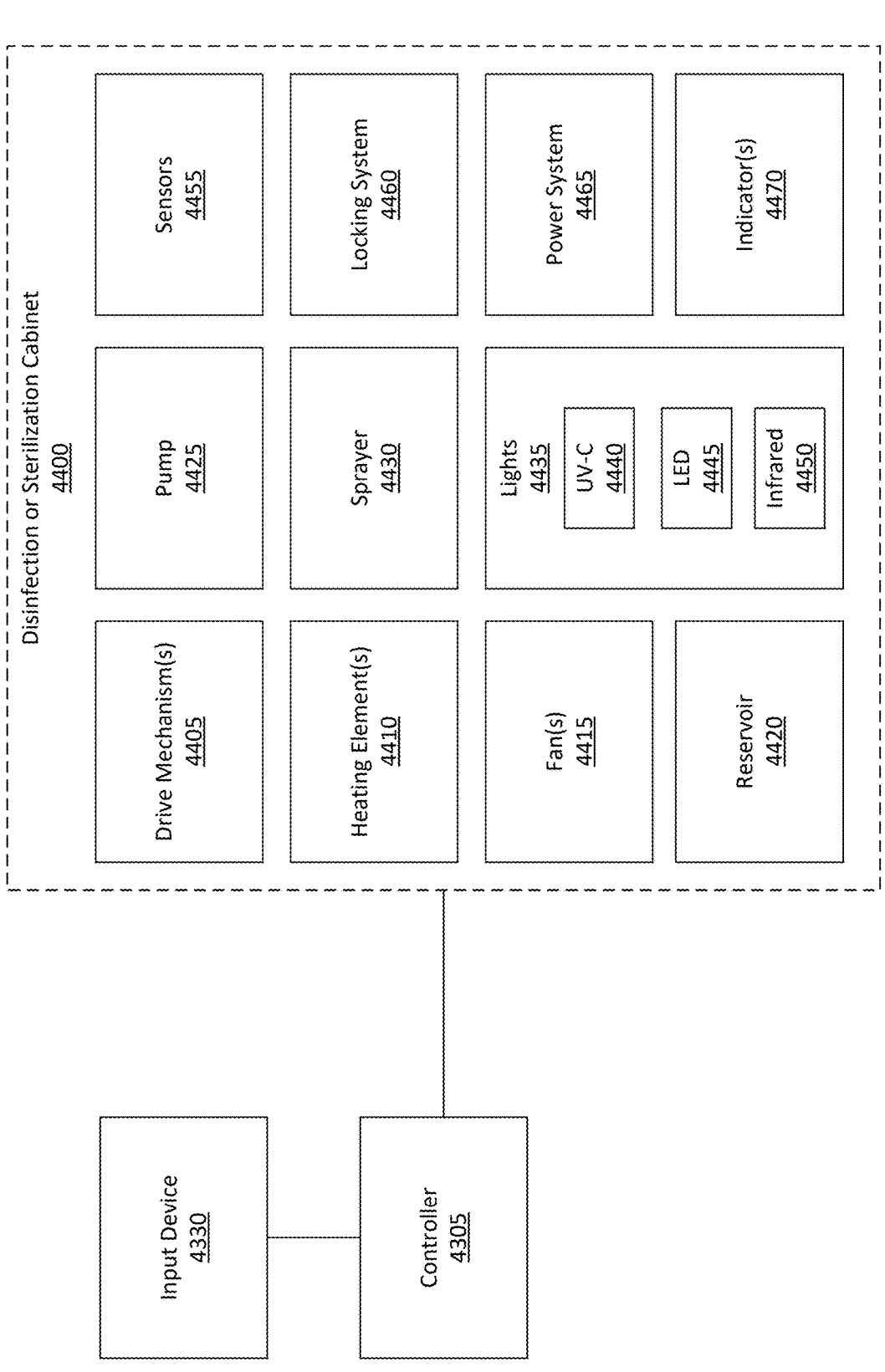
FIG. 44 is a block diagram of a disinfection or sterilization cabinet, according to an embodiment.

Referring now to FIGS. 43 and 44, a control system 4300 for a disinfection and sterilization cabinet 4400 is shown. The control system 4300 can be used to control disinfection and sterilization cabinet 4400 in addition to any of the above-described disinfection or sterilization cabinets or other disinfection cabinets. More specifically, the control system 4300 can be configured to control, monitor, or influence the operation of a disinfection or sterilization operation performed within the cabinet 4400, as well as any related operations. For example, the control system 4300 can be configured to initiate a disinfection and sterilization operation and provide a visual indication to an operator as to the current state of the cabinet 4400. In another example, the control system 4300 can be configured to lock or unlock one or more doors of the cabinet 4400.

The control system 4300 can include a controller 4305. The controller 4305 can include a communication interface 4310 and a processing circuit 4315. The processing circuit 4315 can include at least one processor 4320 and a memory device 4325. As noted above, the controller 4305 can be configured to control, monitor, or otherwise influence one or more operations of the cabinet 4300. Accordingly, the controller 4305 can be communicably coupled with the cabinet 4300 and all related components of the cabinet 4400 as shown in FIG. 44 and discussed in detail below.

The communication interface 4310 of the controller 4305 can be configured to exchange information over a network. The communication interface 4310 can include program logic that facilitates connection of the controller 4305 to the network (e.g., a cellular network, Wi-Fi, Bluetooth, radio, etc.). The communication interface 4310 can support communications between the controller 4305 and other systems, such as a remote monitoring computing system. For example, the communication interface 4310 can include a cellular modem, a Bluetooth transceiver, a radio-frequency identification (RFID) transceiver, and a near-field communication (NFC) transmitter. In some embodiments, the communication interface 4310 includes the hardware and machine-readable media sufficient to support communication over multiple channels of data communication.

The communication interface 4310 may also facilitate the transmission of data and commands between the controller 4305 and various other systems or devices, such as a remote control module, hospital computing system, military dispatch center, trauma center dispatch center, etc. In such embodiments, the communication interface 4310 may communicate with other systems or devices associated with the cabinet 4400 via an internal communications network, such as a controller area network (CAN bus) or another electronic communications protocol. Put another way, the cabinet 4400 can be communicably coupled with the controller 4305 via the communication interface 4310 using a wired or wireless communication protocol as is well understood in the art.

As mentioned above, the controller 4305 includes a processing circuit 4315, which further includes a processor 4320 and a memory 4325. The processor 4320 may be coupled to the memory 4325. The processor 4320 may be one or more specialized or other suitable processors, one or more application specific integrated circuits (ASIC), one or more field programmable gate arrays (FPGAs), a group of processing components, or other suitable processing components. The processor 4320 is configured to execute computer code or instructions stored in the memory 4325 or received from other computer readable media (e.g., CDROM, network storage, a remote server, etc.).

The memory 4325 may include one or more devices (e.g., memory units, memory devices, storage devices, etc.) for storing data and/or computer code for completing and/or facilitating at least some of the various processes described in the present disclosure. The memory 4325 may include random access memory (RAM), read-only memory (ROM), hard drive storage, temporary storage, non-volatile memory, flash memory, optical memory, or any other suitable memory for storing software objects and/or computer instructions. The memory 4325 may include database components, object code components, script components, or any other type of information structure for supporting the various activities and information structures described in the present disclosure. The memory 4325 may be communicably connected to the processor 4320 via processing circuit 4315 and may include computer code for executing (e.g., by the processor 4320) one or more of the processes described herein.

In some embodiments, the memory 4325 may further include one or more circuits configured to control, monitor, or otherwise influence the operation of the cabinet 4400. For example, the memory 4325 can include a disinfection and sterilization circuit storing instructions that, when executed, cause the cabinet 4400 to perform a disinfection and sterilization operation. In another embodiment, the memory 4325 can include one or more other circuits, such as a user management circuit, a notification circuit, configured to provide information to an operator of the cabinet 4400. In yet other embodiments, the memory 4325 can include other circuits configured to cause the cabinet 4400 and related devices to perform or not perform various other functions or operations. In these embodiments, the one or more circuits can comprise instructions (e.g., code, modules of programmatic instructions or code, etc.) stored in the memory 4325 that is executable by the processor 4320. Accordingly and in these embodiment, each of the one or more circuits can comprise executable computer code stored in the memory 4325 that, when executed by the processor 4320, may cause the controller 4305 and/or any such communicably coupled component or system to perform some operation or otherwise respond. According to an exemplary embodiment having multiple circuits, each of the circuits can be communicably coupled to the other circuits via the processor 4320 such that one or more circuits may prompt or cause the execution of code associated with another of the one or more circuits, for example.

In other embodiments, the memory 4325 may not include one or more circuits. Rather, one or more circuits may be embodied as hardware units, such as electronic control units. Accordingly, each of the circuits may include one or more processors that are communicably coupled to one or more memory devices such that the one or more processors may execute instructions stored in the memory or memory device. In another embodiment, the aforementioned circuits can include one or more processors configured to execute instructions that are otherwise accessible to the circuit (e.g., remotely located). Any circuits may thus include components that are distributed across one or more locations. In yet another embodiment, one or more circuits may comprise one or more analog circuits, electronic circuits (e.g., integrated circuits (IC), discrete circuits, system on a chip (SOC)

circuits, microcontrollers, etc.), telecommunication circuits, hybrid circuits, and any other type of component for accomplishing or facilitating achievement of the operations described herein. For example, one or more circuits may include one or more transistors, logic gates (e.g., NAND, AND, NOR, OR, XOR, NOT, XNOR, etc.), resistors, multiplexers, registers, capacitors, inductors, diodes, wiring, and so on. Furthermore, one or more circuits can include programmable hardware devices such as field programmable gate arrays, programmable array logic, programmable logic devices or the like. In another embodiment, one or more circuits may also include one or more memory devices for storing instructions that are executable by a processor of the said one or more circuits. The memory and processor for the one or more circuits can have the same definition as provided above with respect to the processor 4320 and memory 4325. In yet another embodiment, at least one circuit may be embodied as computer-readable code stored in the memory 4325 and executable by the processor while another circuit is configured as a separate hardware or processing unit as described above. All such variations are intended to fall within the scope of the present disclosure.

The controller 4305 can be communicably coupled with an input device 4330. The input device 4330 can be a user interface (e.g., touch screen device) coupled with or mounted on the cabinet 4400, according to one embodiment. The input device 4330 can also be a cellular or mobile device of an operator configured to present one or more graphical user interfaces whereby an operator may control, monitor, or influence the operation of the cabinet 4400. In yet another example, one or more input devices 4330 (e.g., a user's mobile device, a remotely-located computer, and a cabinet-mounted control module, etc.) can collectively be used to communicate commands, data, or information to the controller 4305 for the purpose of controlling, monitoring, or otherwise influencing the operation of the cabinet 4400.

The input device 4330 can also be configured to receive information from the controller 4305 regarding the cabinet 4400, operations of the cabinet 4400, or otherwise. For example, the input device 4330 can display information pertaining to a current state of the cabinet (e.g., an amount of time remaining of a disinfection and sterilization cycle, a message to fill a disinfectant reservoir, etc.). In embodiments where the input device 4330 is a wireless device (e.g., mobile phone, etc.), an operator may receive notifications related to the cabinet 4400 and the operations thereof. For example, a medical professional may receive an indication via mobile device that a disinfection and sterilization operation is complete, whereupon the medical professional can promptly retrieve any disinfected or sterilized equipment from within the cabinet 4400. Accordingly, an operator may both control the cabinet 4400 as well as monitor the operations of the cabinet 4400 via the input device 4330.

The cabinet 4400 can include a top member or portion, a bottom member or portion, a front member or portion, a rear member or portion, and at least one door coupled to the front portion or the rear portion and configured to move between a closed position and an open position. According to an exemplary embodiment, the cabinet 4400 may include four side walls, including the front portion, the rear portion, and two side portions, where each of the side portions are doors. The cabinet 4400 may define a cabinet interior. In one example, objects to be disinfected can be placed within the cabinet interior to be disinfected. The doors can be configured to provide access to the cabinet interior when in the open position. When the doors are in the closed position, the doors substantially prevent access to the cabinet interior.

The cabinet 4400 can include one or more drive mechanisms 4405, one or more heating elements 4410, one or more fans 4415, a reservoir 4420, a pump 4425, a sprayer 4430, lights 4435, sensors 4455, a locking system 4460, a power system 4465, and one or more indicators 4470. The lights 4435 can further include one or more UVC lights 4440, one or more LED lights 4445, and one or more infrared lights 4450. According to an exemplary embodiment, each of these components can be positioned on, in, or around the cabinet 4400. For example, various of these components could be installed within a top member or portion of the cabinet 4400 that is separate from an interior of the cabinet 4400. Likewise, various of these components could be positioned within the interior of the cabinet 4400 (i.e., a treatment area where objects to be disinfected a placed). Moreover, various components could be could be coupled to a bottom member or portion of the cabinet 4400, an exterior surface of the cabinet 4400, or remotely coupled to the cabinet (e.g., not directly coupled to the cabinet 4400 itself).

In addition to the above-introduced components, the cabinet 4400 can also include an internal framework (e.g., rotating carrousel like that shown in FIGS. 11 and 24 and described above) that is configured to couple with a plurality of brackets, where the brackets are configured to support one or more objects (e.g., electronic devices, personal protective equipment, medical devices, therapy devices, etc.).

The drive mechanism 4405 can be an electrical motor coupled to a drive-clutch that is configured to, when powered, rotate an internal framework (i.e., rotating carrousel) within the cabinet interior. The drive mechanism, 4405 may be couple to a central shaft, a top member (e.g., wings 1101 shown in FIG. 11), or a bottom member of the interior framework. In one embodiment, two drive mechanism 4405 may be configured to rotate the interior framework, one drive mechanism 4405 coupled to the top member of the framework and one drive mechanism 4405 coupled to the bottom member. In some embodiments, the drive mechanism 4405 may have a gear box or power transmission device to alter the speed of the rotating internal framework. In another embodiment, the drive mechanism 4405 may be a variable speed electric motor.

The heating element 4410 may be a resistive heating element configured to generate heating energy when powered. The heating element 4410 can be positioned within the cabinet interior or positioned elsewhere on, in, or around the cabinet 4400 as to provide heating energy into the cabinet interior. In one embodiment, the heating element 4410 may be positioned proximate the fans 4415 so that air that is circulated in the cabinet interior may heated, thereby distributing heat throughout the cabinet interior. In various embodiments, multiple heating elements 4410 may be included to expedite the heating of the interior and/or provide heating energy evenly to the cabinet interior. The heating element 4410 could also be a ceramic heater, infrared heater, or some other heater configured to generate heating energy when powered via electricity. In another embodiment, the heating element 4410 could be a gas-powered heater (e.g., boiler system providing radiant heat to the cabinet interior via hot water), a furnace generating hot air, a heater core, a heat pump, etc.

The one or more fans 4415 can be configured to circulate air throughout the cabinet interior. The one or more fans 4415 can include a motor including an output shaft that is coupled to a plurality of angled blades that, when rotated, push or pull air, creating airflow. In another embodiment, the one or more fans 4415 could be a blower motor, an air mover, or a similar device configured to circulate air. The one or more fans 4415 can be fluidly coupled to the cabinet interior via one or more ducts that direct air to specific locations within the cabinet interior, in specific directions, at a particular speed, etc. For example, the one or more fans 4415 can be configured to provide air to the cabinet interior via a duct located in a corner of the cabinet, the corner defined by the front or rear portion or member and one of the doors, according to one embodiment. Similar to the embodiment shown in FIG. 13 and described above, air may flow through a corner duct into the cabinet interior. In one embodiment, the one or more fans 4415 can be positioned proximate a base of a corner duct and can be configured to force air up through the corner duct towards the top portion or member of the cabinet 4400.

The reservoir 4420 can be a container configured to store chemical disinfectant fluid, such as a hydrogen peroxide solution. According to one embodiment, the reservoir may have a removable cap that, when removed, provides access to an interior of the reservoir. An operator may fill interior of the reservoir with chemical disinfectant solution for use during a disinfection or sterilization cycle. In another embodiment, multiple reservoirs 4420 may be used, where each reservoir is configured to store the same or different liquids, including various chemical disinfectants, water, etc.

The pump 4425 can be configure to draw a fluid out of the reservoir 4420. Accordingly, the pump 4425 is fluidly coupled to the reservoir via a fluid conduit (e.g., a pipe, hose, etc.). When powered, the pump 4425 is configured to draw fluid (e.g., chemical disinfectant, namely a hydrogen peroxide solution) out of the reservoir and move it to another location (i.e., the atomizing nozzle 4430) via the fluid conduit. The pump 4425 may be electrically powered, according to one embodiment.

The atomizing nozzle 4430 can be configured to atomize the fluid drawn from reservoir 4420 by the pump 4425 and provide the atomized fluid to the cabinet interior.

According to one embodiment, the atomizing nozzle 4430 may be an atomizing nozzle arm that is positioned within the cabinet interior and is configured to distribute atomized droplets of fluid (e.g., hydrogen peroxide solution) having a size of 10-100 μm (i.e. 50-60 μm, 70 μm, etc.) In one embodiment, the atomizing nozzle 4430 can include one or more nozzles configured to pressurize the fluid exiting the atomizing nozzle 4430 and precisely direct the fluid. The atomizing nozzle 4430 may be positioned proximate the top portion or member of the cabinet 4400 and may disperse atomized liquid disinfectant downwards, according to one embodiment.

As noted above, the lights 4435 can include one or more UVC lights 4440, one or more LED lights 4445, and one or more infrared lights 4450. The lights 4440, 4445, and 4450 can be configured to emit light of a variety of different wavelengths in order to create multi-wavelength light arrangements. More specifically, each of the lights 4440, 4445, 4450 can be configured to emit light having a range of different wavelengths. Moreover, each of the lights 4440, 4445, and 4450 can be configured to emit light of multiple wavelengths simultaneously (i.e., emit both 400 nm light and 600 nm light at the same time). Accordingly, each of the lights 4440, 4445, 4450 can include one or more bulbs, lamps, diodes, etc. to simultaneously emit light of various wavelengths simultaneously.

The UV-C lights 4440 can be configured to emit UV-C light within UV-C range, namely light the having wavelengths of 100-280 nm. In one embodiment, the UV-C lights 4440 are configured to emit light at approximately 254 nm. The LED lights 4445 can be configured to emit light at wavelengths from 400-700 nm (e.g., at 400, 500, 600, 700 nm). Furthermore, the LED lights 4445 can be configure to emit colored lights (i.e., red, white, green, blue, etc.) or lights with a varying hue. The infrared lights 4450 can be configured to emit light on the infrared spectrum, namely 700 nm-1 mm (e.g., at 940 nm). In some embodiments, each of the lights 4440, 4445, and 4450 operate independently and can operate simultaneously with the other lights 4440, 4445, 4450.

The sensors 4455 can include a plurality of sensor devices configured to detect, measure, or monitor certain parameters within the cabinet interior, parameters related to the cabinet components (e.g., drive mechanism 4405), or parameters outside of the cabinet (e.g., ambient temperature and humidity). Each of the sensors 4455 may be communicably coupled to the controller 4405 such that the controller 4405 can control or otherwise influence the operations of the cabinet 4400 based on data recorded by the sensors 4455. In some embodiments, the sensors 4455 may transmit recorded data to the controller 4405 via the communication interface 4410 at regular intervals, upon a command or poll from the controller 4405, substantially continuously, or continuously.

The sensors 4455 can include a temperature sensor configured to measure a temperature within the cabinet interior, a hygrometer configured to measure the humidity within the cabinet interior, a fluid sensor (e.g., flow meter) configured to measure a volume of fluid flowing through a conduit (i.e., measure an amount of fluid pumped from the reservoir 4420 and dispersed into the cabinet interior via the atomizing nozzle 4430), an air flow meter configured to determine a volumetric air flow rate, a speed sensor configured to determine the rotational speed of a motor (e.g., the drive mechanism 4405 or the one or more fans 4415), an optical sensor configured to detect the presence of an object or obstruction within the cabinet interior (e.g., to determine if an object on the internal framework of the cabinet 4400 will crash into a wall of the cabinet), a pressure sensor, etc. In various embodiments, one or more of each of the aforementioned sensors may be deployed in various positions within the cabinet interior in order to accurately and effectively measure various properties pertaining to a disinfection or sterilization operation of the cabinet 4400

The locking system 4460 can include a manual door lock and an automated door lock. The manual door lock can include a latch and latch receptacle as described above with respect to FIGS. 18 and 19. The automatic lock can be an electromagnetic door lock positioned between a door of the cabinet 4400 and the front portion or member, according to one embodiment. The automatic lock can be configured to lock the side door in response to an indication that a disinfection or sterilization cycle is occurring or is scheduled to occur within a predetermined amount of time. When the door is locked, the automatic lock can substantially prevent access to an interior of the cabinet until the disinfection or sterilization cycle is complete, according to one embodiment. In another embodiment, the automatic door lock can be unlocked in response to an operator command (e.g., manual override command). The automatic locks can therefore bolster the efficacy of the device by substantially ensuring that access to the cabinet interior is not allowed in certain circumstances.

The power system 4465 can be configure to receive power from a conventional wall outlet (i.e., a 120V or 220V outlet), convert the power as necessary, and distribute the power to each of the components of the cabinet 4400 that may require power (e.g., the drive mechanism 4405, the heating elements 4410, the fans 4415, the pump 4425, the atomizing nozzle 4430, the lights 4435, the sensors 4455, and the locking system 4460. According to an exemplary embodiment, the power system 4465 can include a battery or other energy storage device configured to allow the cabinet 4400 to operate as herein described even in absence of a conventional wall outlet or power source. For example, the power system 4465 can include a plurality of battery cells configured to remotely power the cabinet 4400 so that the cabinet 4400 can be operated outdoors (e.g., at a remotely-located military base, etc.). Furthermore, the power system 4465 can include a power input device configured to receive, via an electrical cord, power from a wall outlet. According to one embodiment, the power input device may be positioned on a rear member or portion of the cabinet and proximate the bottom member or portion.

The indicators 4470 can be configured to provide a visual and/or audible indication of a current status of the cabinet 4400 or the objects within the cabinet that are subject to the disinfection or sterilization cycle. In one example, the indicators 4470 can include three lights where each light can be configured to indicate a status of the objects within the cabinet 4400. For example, a red light can indicate that the objects within the cabinet 4400 have not been sterilized or disinfected. A yellow light can indicate that the objects within the cabinet 4400 are currently undergoing a disinfection or sterilization. A green light can indicate that the objects within the cabinet 4400 have been successfully disinfected or sterilized. The indicators 4470 may thus provide a clear, substantially unambiguous visual indication to an operator of the cabinet 4400.

As noted above, the controller 4305 can be configured to control the cabinet 4400. In particular, the controller can be configured to cause the cabinet 4400 to perform various operations related to disinfection or sterilization or objects within the cabinet. The cabinet can be configured to perform UV-C light disinfection operations, chemical disinfection operations involving atomized hydrogen peroxide, rapid surface airflow and air circulation operations, heating operations, multi-wavelength light operations (e.g., UV-C, LED, and infrared light at various wave lengths), and motion operations involving a rotating carrousel within the cabinet 4400.

UV-C light disinfection operations can involve ultraviolet light emitted from UV-C lights 4440, where the light is emitted in the "C" range having wavelengths of 100-280 nm. According to an exemplary embodiment, the UV-C disinfection operations can include emitting UV-C light having a wavelength of 254 nm. UV-C light at 254 nm can inactivate microorganisms located within the cabinet 4400 (i.e., on or proximate to objects supported by brackets within the cabinet 4400) by destruction of nucleic acid of the microorganism through induction of thymine dimers, according to an exemplary embodiment. UV-C light may be emitted from non-ozone emitting UV-C lamps, according to one embodiment. In some embodiments, a plurality of UV-C lamps, Chemical disinfection operations involving atomized liquid disinfectant. As one illustrative example, the atomized liquid disinfectant may be atomized hydrogen peroxide (AHP). The operation/method may include providing AHP to an interior of cabinet 4400. In one example, the pump 4425 of the cabinet 4400 may pump a hydrogen peroxide solution from the reservoir 4420 and distribute it into the interior of the cabinet 4400 using one or more atomizing nozzles 4430. In another example, one or more atomizing nozzles 4430 will create, under pressure, 10-100 μm fluid droplets until an internal fog of AHP fills the interior of the cabinet 4400 such that all objects within the interior are enveloped by the AHP fog. To evenly distribute the AHP throughout the cabinet and to ensure all surface of objects within the interior are enveloped by AHP, air is constantly circulated throughout the cabinet interior using one or more fans 4415 while the carrousel supporting the objects within the interior is rotated by the drive mechanism 4405, according to one embodiment.

Hydrogen peroxide is used to perform two different forms of chemical disinfection. First, hydrogen peroxide is used liquid disinfectant having germicidal qualities. More specifically, at a low concentration within water, hydrogen peroxide droplets can come into contact with microbes with cabinet and kill the microbes according to the germicidal properties of hydrogen peroxide. In addition, the hydrogen peroxide can be used as a sensitizer that, when activated via photodynamic therapy, produce Reactive Oxidative Species (ROS), also known as destructive hydroxyl free radicals, that can attack membrane lipids, DNA, and other essential cell components to further destroy microbes within the interior of the cabinet 4400. In ordinary circumstances, catalase, which is produced by aerobic organisms and facultative anaerobes that possess cytochrome systems, can protect cells from metabolically produced hydrogen peroxide by degrading hydrogen peroxide to water and oxygen. However, the aforementioned ROS created by photodynamically activating the hydrogen peroxide will overwhelm the catalase cell defense.

Photodynamic therapy can be used to produce ROS from the hydrogen peroxide. Specifically, photodynamic effects to produce ROS can include light emitted at different wavelengths, according to an exemplary embodiment. The amount of ROS produced and the rate at which the ROS is produced is controlled by the volume of AHP created via the atomizing nozzles 4430 and the amount of photodynamic therapy applied to the AHP within the interior of the cabinet. Further photodynamic therapy can further neutralize remaining ROS and render all resulting compounds inert and safe.

To adapt to different starting points for relative humidity (Rh), such as a summer Rh that may be higher than a winter Rh, the chemical disinfection operation can operate according to two thresholds that must be met. For example, a minimum volume of AHP disinfectant liquid must be dispersed within the treatment area and a minimum Rh percentage must be reached. By requiring that both a minimum volume of AHP is dispersed in the cabinet and a minimum Rh percentage is achieved, the chemical disinfection procedure ensures that enough AHP is employed in higher humidity conditions when the minimum Rh percentage threshold may be quickly achieved, and sufficient AHP is employed in low humidity conditions even as the dry air absorbs AHP rather than allowing the AHP to be applied directly to treatment area surfaces. According to an exemplary embodiment, the chemical disinfection operation process just short of an AHP saturation point.

The rapid surface airflow operations can be configured to effectively distribute and circulate air throughout the interior of the cabinet 4400, according to an exemplary embodiment. Rather than achieve a vacuum for disinfecting operations, the fans 4415 or other air circulation elements (e.g., blower motors) are configured to circulate air throughout the interior of the cabinet 4400 in order to enhance positive item surface airflow effects. Air can be directed throughout the interior of the cabinet 4400 using one or more ducts (e.g., corner ducts 1203 and 1303, as shown in FIGS. 12 and 13, respectively). Air circulation can cause microbes or microorganisms on a surface of an object to become airborne (i.e., be removed from the surface of the object) by the circulating air, thereby making them more vulnerable to chemical and physical disinfection processes. Furthermore, evenly distributed airflow moves AHP droplets around all sides of objects within the interior of the cabinet 4400 and thus allows all object surfaces to be exposed to AHP. In addition, the circulating air bolsters the penetration of AHP sensitizer (i.e., ROS) into fibers and crevices of porous items. When a chemical disinfection process is complete, the circulating air can accelerate a drying process, according to one embodiment.

Heating operations can include operating a heating element 4410 to heat the interior of the cabinet 4400 or to heat the air circulated by the fans 4415 described above. In various embodiments, the air circulated by the fans 4415 during the rapid surface airflow operations can be heated such that the heating operations and the rapids surface airflow operations occur substantially simultaneously. In various embodiments, heat can precondition microbes or microorganism by expanding, drying, and agitating an outer protective surface of the microbes or microorganism. Heat can also increase a speed of chemical reactions associated with disinfection or sterilization. Furthermore, heat can facilitate drying and removal of humidity from the interior of the cabinet 4400, particularly at the end of a disinfection or sterilization cycle.

In addition to the UV-C light disinfection operations discussed above, the cabinet 4400 can be configured to perform multi-wavelength light operations. According to an exemplary embodiment, multi-wavelength light can facilitate degradation of sensitizer (e.g., hydrogen peroxide or other chemicals) by using are photons of light, both visible and invisible. Specifically, any sensitizer remaining after the chemical disinfection operation described above is broken up and/or degraded by multi-wavelength light when impacted with photons of light emanating from the UV-C lights 4440 (e.g., at 254 nm), the LED lights 4445 at (e.g., at 400, 500, 600, 700 nm), and the infrared lights 4450 (e.g., at 940 nm). The variety of different wavelengths of light emitted from lights 4440, 4445, and 4450 serve to stimulate and break apart the sensitizer molecule. Furthermore, byproducts of the broken-apart sensitizer molecules are rendered inert and safe.

According to an exemplary embodiment, the cabinet 4400 can be configured to perform a high-level disinfection (HLD) of objects placed within the cabinet. More specifically, the disinfection and sterilization operations performed by the cabinet 4400 and herein described may cause the destruction of all viruses, vegetative bacteria, fungi, mycobacterium, and some, but not all, bacterial spores present on or around the objects within the cabinet 4400. In some examples, the high-level disinfection operation may kill 106 mycobacteria (a six-log reduction). According to one embodiment, the cabinet 4400 can be configured to perform a high-level disinfection operation on properly prepared (cleaned, rinsed, and dried) non-critical medical devices in healthcare facilities. Moreover, the chemical disinfection and light treatment cycles operate at low pressure and temperature, which are suitable for processing medical devices without leaving residues. In addition, the disinfected devices are ready for use at the completion of the cycle, no cool down or aeration period is required after the cycle is complete. The disinfection or sterilization operations herein described can also be used to perform a high-level disinfection operation on medical devices and supplies with diffusion-restricted spaces and/or irregular surfaces like stethoscopes, blood pressure cuffs, and the like.

The various treatments and operations performed by the cabinet 4400 and its components vis-à-vis the controller 4305 have numerous advantages. For example, an outer layer of microbes within the cabinet 4400 are weakened more by exposure to dry air than moist air. Put another way, a drying out effect will creates imperfect exterior of the microbe that is beneficially susceptible to attack by light treatments and chemical disinfectants. Accordingly, a disinfection or sterilization cycle may begin with very dry air and finish treatments with very dry air. Relatedly, the impact of dry air upon a microbe's outer layer is significantly enhanced by a high volume of air moving across the microbe's surface. For this reason, a large volume (i.e., hundreds of cubic feet of air per minute) may be circulated within an interior of the cabinet 4400.

The surface area of a microbe's outer layer expands with temperature, causing the outer layer to stretch. This creates a maximum treatment surface area for chemical disinfectant and light treatment methods to attack the microbe. Furthermore, the expanding outer layer causes the outer layer to stress, potentially creating surface fissures that can be exploited by chemical disinfectant or light treatment. Accordingly, a disinfection or sterilization cycle may begin our treatments with cool air and subsequently introduce and circulate hot air to the interior of the cabinet 4400 to expose all microbes to heat.

Many species of microbe will clump together as a result of disinfection methods, which may cause the outer microbes of a group of microbes to be destroyed while the outer microbes protect living microbes beneath. In some cases, this occurs when the microbes are also in the process of drying out due to air and heat exposure. To remedy this, moisture is introduced to the interior of the cabinet and distributed (via air circulation and motion of the internal framework of the cabinet) to all or substantially all surfaces where microbes may be present. The introduction of moisture further occur within structured timing intervals. This moisture can re-hydrate the surfaces of microbes, causing them to expand via a wicking effect whereby outer microbes are removed previously-protected microbes are exposed. The process may then repeat to remove the next layer of microbes in a group of microbes. Beneficially, the repeated expansion and retraction of microbe surfaces creates fissures and weaknesses on the microbe surfaces, making the microbes more vulnerable to chemical disinfectant or light treatment.

Some objects requiring disinfection can carry organic matter (e.g. blood, sputum, feces) among the microbes intended for disinfection. The organic matter may be dried or at a thickness to obscure any surface access for treatment. This is known as "soiled" status and disinfection treatments are more difficult to achieve in these soiled areas. Accordingly, objects placed within the cabinet 4400 may preferably be manually cleaned and visibly inspected to ensure no soiled areas remain before the objects are placed in the cabinet 4400. This further prevents solid waste from entering the treatment area.

Microbes can have a curved surface. Moreover, surfaces of objects that may be placed in the cabinet 4400 for disinfection or sterilization may have porous surface areas, smooth surface areas, and crevices. Microbes can be located in or around these various surface characteristics. These microbes may thus be positioned as to partially occluded such that they cannot be targeted for disinfection via a direct line-of-sight. To remedy this, the combination of light treatment and moisture (i.e., water, chemical disinfectant, AHP) facilitates the bending of the light used via the water molecules or chemical disinfectant droplets positioned across or atop the surface of the object. The water molecules or chemical disinfectant droplets can catch and guide the light from the light treatment around curves and corners to reach otherwise occluded microbes. Moreover, by introducing moisture to the surfaces within structured timing to re-hydrate surfaces, the wicking effect can draw out microbes or other bioburden within material layers, across surfaces, and make microbes more treatable.

As discussed above, all objects within the cabinet 4400 and which will undergo a disinfection or sterilization operation are supported within the cabinet 4400 via a mounting bracket (e.g., one of the brackets shown and described with reference to FIGS. 25A-42B). According to an exemplary embodiment, all mounting brackets are secured to the cabinet's internal framework. In various embodiments, the internal framework is moveable, such as the rotatable carrousel shown and described with reference to FIGS. 11 and 24. The internal framework can be driven by a drive mechanism 4405 and can rotate within the cabinet 4400 about a central axis, according to one embodiment. The movement of the internal framework—and thus the objects supported by brackets coupled with the internal framework—allows the chemical disinfectant, UV-C light, multi-wavelength LED light, infrared light, heat, and circulated air to reach all sides and surfaces of the item and avoid "shadowing effects" that may occur to prevent incomplete coverage when portions of an object are occluded, inaccessible in one position within the cabinet 4400. In one embodiment, a circular carrousel with wings that extend from center, such as that shown in FIGS. 11 and 24 allow for movable brackets to be attached to a center post (e.g., center shaft 1103) and extend center-outward (i.e., radially from the center post) or be attached to an outside post (e.g., wing frame 1105) and extend outside-inward (e.g., towards the center post) to achieve a desirable spacing between items in order to further increase coverage of treatments on objects while the internal framework is in motion.

While a variety of processes or treatments can be employed individually to sterilize or disinfect objects placed within the cabinet 4400, the variety of processes or treatments may be employed in a particular sequence and with particular specifications in order to achieve a desired sterilization or disinfection result (i.e., a desired efficacy level, a desired cycle time, etc.). According to one embodiment, the controller 4305 may be programmed to perform a series of disinfection or sterilization operations in a particular order and with particular specifications. Furthermore, a user may be able to select a predefined disinfection or sterilization cycle from the input device, whereupon the controller 4305 will control the operations of the cabinet 4400 to perform the predefined disinfection or sterilization cycle, for example. In one example, the controller 4305 may store a plurality of predefined disinfection or sterilization cycles in the memory 4325, where at least some include instructions for performing a disinfection or sterilization cycle involving a combination of the treatment operations and processes described above.

Figure 45:
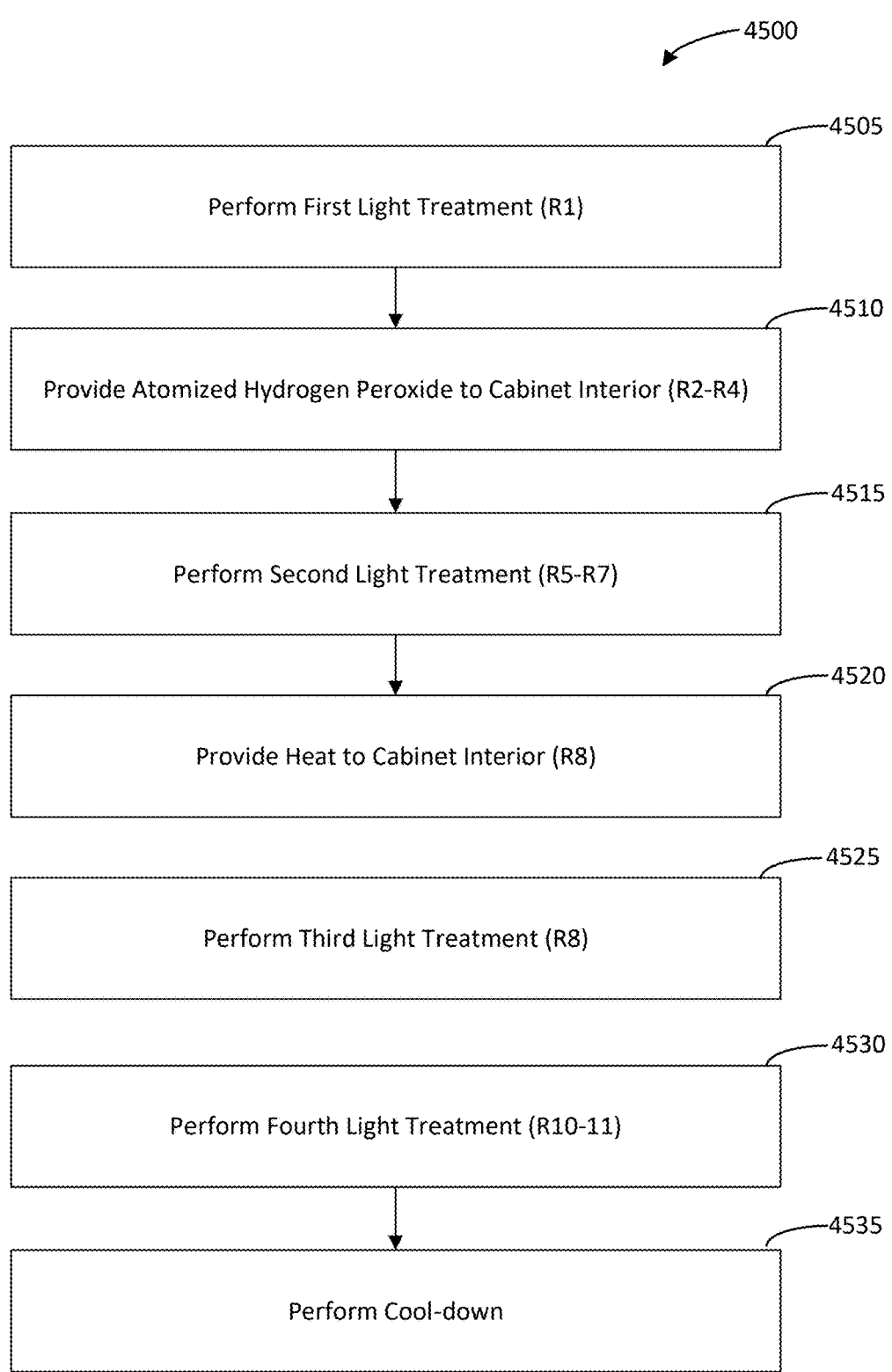
FIG. 45 is a flow chart of a method of operating a disinfection or sterilization cabinet, according to an embodiment.

Referring now to FIG. 45, a disinfection or sterilization method 4500 is shown. According to an exemplary embodiment, the method 4500 can be performed by the control system 4300 and the cabinet 4400. More specifically, the controller 4305 may control, monitor, and otherwise influence the operation of the cabinet and its various components in order to perform the method 4500 as herein described.

At process 4505, the controller 4305 may cause the cabinet 4400 to perform a first light treatment operation.

More specifically, the first light treatment operation can include emitting light from UV-C lights 4440 at a wavelength of, for example, 254 nm. The light may be emitted from a plurality of UV-C lights 4440 positioned throughout the interior of the cabinet 4400 to maximize light exposure to objects positioned therein. While the UV-C lights are emitting UV-C light, the interior framework of the cabinet 4400 may be rotated to further increase the amount of UV-C light that is exposed to objects within the cabinet 4400. In addition, air may be circulated via fans 4415 to blow microbes off of the surfaces of said objects while the interior framework is in motion. The air circulated via fans 4415 may be approximately 78 degrees Fahrenheit, according to one embodiment. In another embodiment, the circulated air is at an ambient temperature or cooler. According to an exemplary embodiment, UV-C may be emitted from the UV-C lights 4440 create exposure of 21,224 fluence mW/mJ per $cm^2$.

In process 4510, the controller 4305 may cause the cabinet 4400 to provide atomized liquid disinfectant (AHP) to an interior of the cabinet 4400. According to one embodiment, a hydrogen peroxide solution may be pumped from the reservoir 4420 by the pump 4425 and introduced to the interior of the cabinet via the atomizing nozzle 4430. The atomizing nozzle 4430 may be configured to provide AHP droplets having a size of 50-60 µm. In another embodiment, the atomizing nozzle 4430 may be pressurized and may create droplets having a size of 7 µm. The hydrogen peroxide solution used to create the AHP droplets can be a 6% hydrogen peroxide solution. The amount of AHP introduced to the interior of the cabinet 4400 may depend on the chosen cycle (e.g., a "heavy" cycle may introduce more AHP, while a "normal" cycle may introduce less). In various embodiments, AHP is projected into the cabinet 4400 until a predefined criteria is met (e.g., a threshold relative humidity, a minimum volume of AHP, etc.).

Process 4510 can occur while the internal framework of the cabinet 4400 is in motion, as described above with reference to process 4505. Moreover, air may be circulated throughout the interior of the cabinet 4400 while AHP is dispersed. The circulating air can move the AHP droplets within the cabinet interior such that all objects within the cabinet are exposed to AHP. Furthermore, air may be circulated within the cabinet 4400 at a sufficient force to cause the AHP to penetrate multiple layers of multi-layered objects (e.g., a facemask).

At process 4515, the controller 4305 may cause the cabinet 4400 to perform a second light treatment operation. The second light treatment operation can include the intermittent flashing of UV-C lights 4440 and LED lights 4445. The UV-C lights 4440 may emit light at a wavelength of approximately 254 nm. The LED lights 4445 may emit light at a wavelength of approximately 400 nm (visible blue light), a wavelength of approximately 550 nm (visible green light), and at a wavelength of approximately 400-700 nm (visible white light). In some embodiments, infrared lights 4450 may also emit infrared light during process 4515.

When light is emitted from UV-C lights 4440 and LED lights 4445 as noted above, Reactive Oxidative Species (ROS, AHP sensitizer) is created from the AHP. Because the light is only flashed intermittently, AHP can travel to the surfaces of objects within the cabinet interior before ROS is created such that the ROS may be positioned to attack and destroy microbes on the surface of the objects, which is of particular importance given the limited lifespan of ROS and the limited distance over which it can travel. Put another way, the intermittent flashing of lights 4440 and 4445 allows raw AHP to travel near to treatment surfaces before that raw AHP is activated to create ROS so that the ROS can be effectively used at the treatment surfaces before being deactivated.

During process 4515, UV-C lights 4440 can emit a total of 200-450 mJ/cm$^2$ of UV-C light within the cabinet interior. Light of a shorter wavelength is more powerful than light of a longer wavelength because shorter wavelength light has an increased photon photoactivation power.

While the third light treatment is occurring at process 4515, the microbes killed during the first light treatment at process 4505 may be re-hydrated by the AHP dispersed within the cabinet. When re-hydrated, the re-introduced moisture in these microbes can create a wicking effect that causes the previously-killed and re-hydrated microbes to wick off of a group or clump of microbes, thereby exposing additional previously-shielded microbes of the group. The wicking effect can draw microbe bodies out from an object surface and expand the outer layer of the microbe. Furthermore, a water droplet lens can be created around these microbe bodies that bends the UV-C light from lights 4440 around obstructions and/or into pores or crevices to enhance the destruction of microbes via the intermittent UV-C light at process 4515.

Moreover, AHP can be degraded during the third light treatment. More specifically, the photoactivation of the atomized hydrogen peroxide (or other sensitizers) may cause the hydrogen peroxide to degrade and break down into inert components, namely water and oxygen. The degradation of AHP is important to ensure that when the disinfection or sterilization cycle is complete, any chemicals that are potentially harmful to users or bystanders is eliminated.

At process 4520, the controller 4305 may cause the cabinet 4400 to provide heat to the interior of the cabinet 4400. More specifically, the heating element 4410 may generate heating energy within the interior of the cabinet 4400 in order to raise the temperature of the interior. According to one embodiment, the interior of the cabinet 4400 may reach a temperature of approximately 90 degrees Fahrenheit. In other embodiments, the interior of the cabinet 4400 may achieve a temperature of 110-150 degrees Fahrenheit. In yet other embodiments, the interior of the cabinet 4400 may achieve a higher temperature still. The heating element 4410 and sensors 4455 (i.e., temperature sensor) may be configured to achieve a desired temperature within the interior of the cabinet 4400 and then maintain that temperature for a predetermined amount of time, according to one embodiment.

The heat within the interior of the cabinet 4400 can be configured to dry the items within the cabinet 4400 (i.e., remove moisture from the cabinet interior). Moreover, the heating energy supplied by the heating element 4410 can cause any remaining AHP (i.e., that AHP not converted into ROS at process 4515) to activate ROS. As described above, the ROS may be configured to kill remaining microbes. Furthermore, heating the interior of the cabinet 4400 can also degrade or break down the AHP within the cabinet 4400.

At process 4525, the controller 4305 may cause the cabinet 4400 to perform a third light treatment operation. The third light treatment may include light emitted from LED lights 4445. In other embodiments, the third light treatment may include light emitted from UV-C lights 4440 and/or infrared lights 4450. Light may be emitted from the LED lights 4445 at a wavelength of 700 nm (visible red light) and at a wavelength of 400-700 nm (visible white light). This light may be configured to activate ROS and/or degrade AHP, according to one embodiment.

At process 4530, the controller 4305 may cause the cabinet 4400 to perform a fourth light treatment operation. More specifically, the fourth light treatment operation can include emitting light from UV-C lights 4440 at a wavelength of, for example, 254 nm. As with process 4505, the interior framework of the cabinet 4400 may be rotated while the UV-C lights 4440 are emitting UV-C light to further increase the amount of UV-C light that is exposed to objects within the cabinet 4400. Likewise, air may be circulated via fans 4415 to blow microbes off of the surfaces of said objects while the interior framework is in motion. The UV-C light emitted at process 4530 can be configured to kill any remaining microbes within the interior of the cabinet 4400. Because process 4530 can occur after moisture and heat are introduced to the interior of the cabinet 4400, any remaining microbes may have outer layers that are expanded in size and spread such that they are already considerably weakened from processes 4505-4525, according to one example. Moreover, the UV-C light of the fourth light treatment can photoactivate any remaining sensitizer or hydrogen peroxide within the interior of the cabinet 4400, which further serves to degrade the chemicals within the cabinet into inert components.

At process 4535, the controller 4305 may cause the cabinet to perform a cool-down operation. During process 4535, air is circulated throughout the cabinet to further dry out the objects within the interior of the cabinet 4400. The circulating air will cool the surfaces of the objects within the cabinet and can also degrade any remaining hydrogen peroxide. According to one embodiment, the cool-down operation can be configured to cool the objects within the cabinet 4400 until said objects are sufficiently dry (e.g., dry to the touch) and cool (e.g., cool to the touch). When the cool-down cycle completes and a door of the cabinet 4400 is opened to retrieve the objects from within, a cool rush of ambient air fills the interior of the cabinet 4400, which can further degrade any remaining hydrogen peroxide, according to one embodiment.

In various other embodiments, various steps of the method 4500 may be optionally excluded (i.e., not performed). In other embodiments, various steps of method 4500 may be performed in a different order. In yet other embodiments, various steps of the method 4500 may be performed at least partially simultaneously (i.e., occurring at the same time for at least part of the duration of each operation), may begin simultaneously, and/or may end simultaneously. For example, process 4520 and process 4525 may, according to some embodiments, be performed simultaneously. Relatedly, the performance of one operation according to one step of method 4500 does not require that other previously-initiated method steps will cease or end. Rather, certain steps of method 4500 may begin after a preceding step is initiated, but may continue operation for a duration of time irrespective of the performance of any subsequent steps of the method 4500.

In some embodiments, various operations of the processes 4505-4535 of the method 4500 may continue to subsequent processes while other operations do not. For example, at process 4505, UV-C light can be emitted while the interior framework of the cabinet rotates and while air is circulated. When the method 4500 proceeds to process 4510, the UV-C lights 4440 may stop emitting UV-C light, but the interior framework of the cabinet 4400 may continue to rotate and air may continue to be circulated. In another example, the interior framework of the cabinet 4400 remains in motion during substantially the entire method 4500.

The various operations of the processes 4505-4535 of method 4500 can be configured to last for a predetermined amount of time. In other embodiments, various operations may start or stop based on data or information provided by sensors 4455 within or around the cabinet 4400. For example, the atomizing nozzle 4430 may stop atomizing and dispersing AHP within the interior of the cabinet 4400 based on data received from a hygrometer, for example. In another example, a light sensor may detect the cumulative light energy emitted from lights 4435 and may stop a light therapy operation when the cumulative light energy emitted surpasses a threshold. In yet other embodiments, other operations may start, stop, or be modified by the controller 4305 based on information received from the sensors 4455.

According to one embodiment, method 4500 may last approximately 15-20 minutes in duration. In other embodiments, the method 4500 or other disinfection or sterilization methods can last 20 or more minutes or less than 15 minutes. The various objects within the cabinet 4500 may be ready for use immediately upon completion of the method 4500, according to one embodiment. Furthermore, all chemicals, moisture, etc. within the cabinet interior (i.e., excluding the reservoir 4420) may be inert and safe.

One embodiment provides a new and improved item disinfection system and method that provides the operator with an operator viewing window that is safety glass and UV-C resistant thereby allowing the operator to observe the interior of the cabinet at all times.

One embodiment provides a new and improved item disinfection system and method that provides the operator with an operator screen that allows the selection of cycle modes, settings, timings, as well as system status communication methods whereby the operator can see the current status, error messages, instructions and more.

One embodiment provides a new and improved item disinfection system and method that has lights and indicators on both operating sides of the cabinet whereby the lights and screens communicate the machine status (e.g. "Dirty/Ready for Loading", "In-Use", "Clean/Ready for Unloading", etc.) using colors and words to easily convey to the operator a status.

One embodiment provides a new and improved item disinfection system and method that features a full system test cycle upon powering up the cabinet. A test cycle tests all disinfection subsystems and sensors for proper working order and asks the operator to confirm a success. This test cycle provides confidence that all subsequent activity is being performed properly.

One embodiment provides a new and improved item disinfection system and method that includes dynamic control software that contains actions and decisions using sensor inputs to perform the selected disinfection treatment cycle.

One embodiment provides a new and improved item disinfection system and method that has a smooth exterior surface on all sides with no exposed wires or cords or protruding parts that could be caught during operation or transportation of the cabinet.

One embodiment provides a new and improved item disinfection system and method that requires only a single 120v 15 a power connection to accomplish all operations and is easily powered by external power generators or a battery pack.

One embodiment provides a new and improved item disinfection system and method that enables matching the disinfection treatment plan to the items (and their materials)

requiring disinfection. A disinfection treatment plan is based upon [contaminant X materials X disinfection method X duration]. The ability to include (or exclude) a disinfection method based upon a material match (or conflict) is part of this embodiment.

One embodiment provides a new and improved item disinfection system and method that provides operating software controls that assure a disciplined/metered treatment efficacy for the varied items and materials and contaminants requiring disinfection, operate and communicate system and cycle status.

One embodiment provides a new and improved item disinfection system and method that can be self-operated by the institution, requiring no 3rd party expense or dependency.

One embodiment provides a new and improved item disinfection system and method that is a "closed system" whereby no air or atomized liquid may be evacuated outside the enclosure for any purpose during or following the operation of the cabinet. The system is self-contained and inert at the end of any cycle whereby the enclosure, items, contaminants, and disinfection materials used in the treatment cycle do not affect the cabinet's operator or item's user or the cabinet's operating environment whereby additional precautions may be taken post-treatment or post-cycle.

One embodiment provides a new and improved item disinfection system and method that provides multiple disinfection methods and item manipulation whereby the cabinet maintains a sound level of 85 decibels or less and cannot be detected from outside a sealed operating area.

One embodiment provides a new and improved item disinfection system and method that allows the operator to place and remove items within the cabinet without having to step into the enclosure or reach or bend or stoop in a manner that causes physical strain or long-term fatigue or injury. A further object is to allow 100% access to the entire enclosure from any door whereby there are no physical panels or barriers between any portion of the interior workspace and the outside when the door is opened (this means the doors can be 100% of the side of the enclosure).

One embodiment provides a new and improved item disinfection system and method that allows an item to fall from its original mounted position inside the enclosure to the bottom of the enclosure whereby the system can continue to operate without damaging the item else the system will stop operating. A further object is to have no moving parts, technology, or any component at the bottom of the enclosure whereby items or fluids could interfere with a disinfection cycle or damage the enclosure or its components.

One embodiment provides a new and improved item disinfection system and method that is susceptible to a low cost of manufacture with regard to both materials and labor, and which accordingly is then susceptible to low prices of sale to the consuming industry, thereby making such cabinet economically available to those in the industry.

One embodiment provides a new and improved item disinfection system and method that provides all of the advantages of the prior art, while simultaneously overcoming some of the disadvantages normally associated therewith.

EXAMPLES

Example 1. Illustrative disinfection cycle. A disinfection cycle begins by placing a object (i.e. substrate) that may be infected with a microbe, spore, fungus, bacteria, etc. into a disinfection chamber onto a moveable rack. After closing the object in the chamber, the object may be subjected to air and UVC illumination in an attempt to dislodge some microbes from the surface of the object and get them airborne within the chamber such that they are more readily subject to the UVC illumination. In this initial stage of the disinfection, it is believed that greater than 99% of the bioburden is killed.

In a second stage, atomized hydrogen peroxide is introduced to the cabinet as a fog from one or more atomizing nozzles. The amount of hydrogen peroxide introduced during any given cycle is determined by the cycle setting for the chamber from "regular" to "heavy." At the regular setting, approximately 23 ml of a 6 vol % $H_2O_2$ in water is atomized into a fog, while at the heavy setting it is approximately 30 ml for cabinet interior volume of approximately 33 ft$^3$. During introduction of the atomized hydrogen peroxide to the chamber, the UVC, and other lighting, is flashed intermittently to take advantage of the additional moisture landing upon the surfaces to be disinfected whereby a wicking effect can be achieved by the rapidly moving air and the new water molecules on the surface and UVC light can extend through the moisture, around curves/corners, and further penetrate surfaces and soils to be disinfected. The pulsing of photons also prepare the atomized hydrogen peroxide to be unstable and active upon landing near a microbe whereby it can deliver its disinfecting capability, including possible photodynamic therapy effects, to prevent immediate degradation of the hydrogen peroxide due to photolysis. The atomized hydrogen peroxide is allowed to disperse throughout the cabinet and onto any object within the cabinet to have a first disinfection by the action of the disinfectant alone, followed by UVC illumination. It is also noteworthy that the exposed microbes in the initial UVC illumination may be subject to drying or clumping, while during the introduction of the atomized hydrogen peroxide they are re-hydrated with the hydrogen peroxide to physically alter the microbial clumping body and more effectively kill those microbes.

The temperature of the chamber is then raised to a minimum temperature of about 32° C., under high airflow. This is maintained for a predetermined period of time that may be from seconds to several or tens of minutes. During this part of the cycle the chamber may be under intermittent or continuous UV, infrared light, and visible light illumination. The warming assists in microbe body expansion for maximum surface area, microbe killing, drying of the cabinet post-fogging with the atomized liquid disinfectant, and in further degrading any remaining dispersed disinfectant. The temperature inside the cabinet may reach about 40° C. to about 60° C. during this portion of the cycle.

During the disinfection cycle, the chamber may be exposed to higher humidity under UVC illumination. As the cycle nears completion, the humidity within the chamber may be reduced. Such cycles are controlled by computer settings based upon the "regular" or "heavy" designation set by the operator. The cabinet is then allowed to cool to room temperature under airflow (cooler and drier compared to the airflow earlier in the cycle) prior to opening of the cabinet and retrieval of now disinfected objects. The cool down period allows for further degradation of any disinfectant material to protect against, contact of a user with the disinfectant material. The total time start to finish of the cycle is adjustable but may range from 1 minute to 2 hours, from 5 minutes to an hour, from 15 minutes to 1 hour, from 20 minutes to 50 minutes, or from about 30 minutes to 40 minutes.

CONCLUSION

Although the subject matter has been described in terms of certain embodiments, other embodiments that may or may not provide various features and aspects set forth herein shall be understood to be contemplated by this disclosure. The specific embodiments described above are disclosed as examples only, and the scope of the patented subject matter is defined by the claims that follow. In the claims, the terms "based upon" and "based on" shall include situations in which a factor is taken into account directly and/or indirectly, and possibly in conjunction with other factors, in producing a result or effect. In the claims, a portion shall include greater than none and up to the whole of a thing.

Although this description may discuss a specific order of method steps, the order of the steps may differ from what is outlined. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps, and decision steps.

As utilized herein, the terms "approximately", "about", "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent, etc.) or moveable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," "between," etc.) are merely used to describe the orientation of various elements in the figures. It should be noted that the orientation of various elements may differ according to other exemplary embodiments, and that such variations are intended to be encompassed by the present disclosure.

It is important to note that the construction and arrangement of the electromechanical variable transmission as shown in the exemplary embodiments is illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the components described herein may be constructed from any of a wide variety of materials that provide sufficient strength or durability, in any of a wide variety of colors, textures, and combinations. Accordingly, all such modifications are intended to be included within the scope of the present inventions. Other substitutions, modifications, changes, and omissions may be made in the design, operating conditions, and arrangement of the preferred and other exemplary embodiments without departing from scope of the present disclosure or from the spirit of the appended claims.

What is claimed is:

1. A method of disinfection of an object, the method comprising:

securing an infected object within a chamber;

exposing the infected object to a disinfection cycle, the disinfection cycle comprising:

directing, via a conduit, an atomized liquid disinfectant into the chamber to expose the infected object to the atomized liquid disinfectant, the atomized liquid disinfectant comprising a disinfectant, the atomized liquid disinfectant to travel a distance from the conduit toward the infected object;

exposing the chamber to non-UV illumination from a first non-UV illumination source before, during, after, or any thereof exposing the object to the atomized liquid disinfectant to disinfect the object, wherein during the disinfection cycle, the first non-UV illumination source is pulsed on and off;

intermittently exposing the atomized liquid disinfectant to ultraviolet illumination from a second illumination source after the atomized liquid disinfectant travels a majority of a distance toward the infected object, the atomized liquid disinfectant to generate reactive oxidative species in response to the ultraviolet illumination from the second illumination source;

during the disinfection cycle changing an orientation of the infected object with respect to the atomized liquid disinfectant; and removing the object from the chamber.

2. The method of claim 1, wherein the atomized liquid disinfectant is formed by a pressurized spraying of a water-based liquid disinfectant solution into the chamber.

3. The method of claim 1, wherein the atomized liquid disinfectant comprises droplets that are about 10 μm to about 100 μm in diameter.

4. The method of claim 1, wherein at removal of the disinfected object from the chamber, no disinfectant remains within the chamber.

5. The method of claim 1, wherein the disinfectant comprises hydrogen peroxide, methylene blue, riboflavin, or a mixture of any two or more thereof.

6. The method of claim 5, wherein the disinfectant comprises hydrogen peroxide.

7. The method of claim 1 further comprising heating the chamber to a temperature from about 25° C. to about 70° C.

8. The method of claim 1, wherein a duration of the disinfection cycle is from about 1 minute to about 2 hours.

9. The method of claim 1, further comprising a third light source configured to emit visible light, infrared light, or a plurality of light wavelengths other than ultraviolet light.

10. The method of claim 9, the third light source including a visible light source and an infrared light source, wherein during the disinfection cycle, the visible light source and the infrared light source are pulsed on and off.

11. The method of claim 1, wherein the disinfection cycle, prior to exposing the infected object to the atomized liquid disinfectant, comprises exposing the infected object and the chamber to a first airflow of 10 ft$^3$/min or more.

12. The method of claim 11, wherein the first airflow is from 10 ft$^3$/min to 1,000 ft$^3$/min.

13. The method of claim 11, wherein the disinfection cycle further comprises as a final step, exposing the object and the chamber to a second airflow of 50 ft$^3$/min or more, wherein the second airflow is drier and cooler compared to the first airflow.

14. The method of claim 13, wherein the second airflow is from 50 ft$^3$/min to 1,000 ft$^3$/min.

15. The method of claim 1, wherein the disinfectant, prior to atomizing, is present in a reservoir as an aqueous solution of from 1 to 30 vol % hydrogen peroxide.

16. The method of claim 15, wherein the aqueous solution is from 3 to 10 vol % hydrogen peroxide.

17. The method of claim 15, wherein the aqueous solution is about 6 vol % hydrogen peroxide.

18. The method of claim 15, wherein the chamber has a volume of about 10 ft$^3$ to about 40 ft$^3$, and a ratio of a volume of an equivalent disinfectant at 100% concentration to the volume of the chamber is from 0 to 0.15 mL/ft$^3$.

19. A method of disinfection of an object, the method comprising:

securing an infected object within a chamber;

exposing the infected object to a disinfection cycle, the disinfection cycle comprising:

directing, via a conduit, an atomized liquid disinfectant into the chamber to expose the infected object to the atomized liquid disinfectant, the atomized liquid disinfectant comprising a disinfectant, the atomized liquid disinfectant to travel a distance from the conduit toward the infected object;

exposing the chamber to illumination from a visible illumination source and an infrared illumination source before, during, after, or any thereof exposing the object to the atomized liquid disinfectant to disinfect the object, wherein during the disinfection cycle, the visible illumination source and the infrared illumination source are pulsed on and off;

intermittently exposing the atomized liquid disinfectant to ultraviolet illumination from a second illumination source after the atomized liquid disinfectant travels a majority of the distance toward the infected object, the atomized liquid disinfectant to generate reactive oxidative species in response to the ultraviolet illumination from the second illumination source;

during the disinfection cycle changing an orientation of the infected object with respect to the atomized liquid disinfectant; and removing the object from the chamber.

* * * * *